(12) United States Patent
Costello et al.

(10) Patent No.: US 9,271,897 B2
(45) Date of Patent: Mar. 1, 2016

(54) TECHNIQUES FOR MANUFACTURING INGESTIBLE EVENT MARKERS COMPRISING AN INGESTIBLE COMPONENT

(71) Applicant: Proteus Digital Health, Inc., Redwood City, CA (US)

(72) Inventors: Benedict Costello, Piedmont, CA (US); Timothy Robertson, Belmont, CA (US); Patricia Johnson, San Carlos, CA (US); Robert Duck, San Francisco, CA (US); Richard Huang, Union City, CA (US); Rod Nicholas, San Leandro, CA (US); Brad Cozad, Newark, CA (US); Hooman Hafezi, Redwood City, CA (US); Kurt Scheinpflug, Fremont, CA (US); Zahedeh Hatamkhany, San Mateo, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 14/415,937

(22) PCT Filed: Jul. 22, 2013

(86) PCT No.: PCT/US2013/051511
§ 371 (c)(1),
(2) Date: Jan. 20, 2015

(87) PCT Pub. No.: WO2014/018454
PCT Pub. Date: Jan. 30, 2014

(65) Prior Publication Data
US 2015/0164746 A1    Jun. 18, 2015

Related U.S. Application Data

(60) Provisional application No. 61/674,851, filed on Jul. 23, 2012.

(51) Int. Cl.
*A61B 5/07*     (2006.01)
*A61J 3/10*     (2006.01)
(Continued)

(52) U.S. Cl.
CPC ... *A61J 3/10* (2013.01); *A61B 5/07* (2013.01); *B30B 11/34* (2013.01); *B32B 37/15* (2013.01); *B32B 38/0012* (2013.01); *B32B 38/10* (2013.01); *B65B 69/00* (2013.01); *A61B 5/14539* (2013.01); *A61J 2200/70* (2013.01); *B32B 2457/00* (2013.01)

(58) Field of Classification Search
None
See application file for complete search history.

(56) References Cited

U.S. PATENT DOCUMENTS 1,548,459 A   8/1925   Hammer
3,589,943 A   6/1971   Grubb et al.
(Continued)

FOREIGN PATENT DOCUMENTS

DE   10313005   10/2004
EP   0344939    12/1989
(Continued)

OTHER PUBLICATIONS

Arshak et al., A Review and Adaptation of Methods of Object Tracking to Telemetry Capsules IC-Med (2007) vol. 1, No. 1, Issue 1, 12pp.
(Continued)

*Primary Examiner* — Mary F Theisen
(74) *Attorney, Agent, or Firm* — K&L Gates LLP

(57) ABSTRACT

Method and systems for manufacturing a tablet comprising an electronic device are disclosed. In one method, a powdered material is provided into a die cavity of a tablet press and an electronic device is dispensed from a tape-and-reel carrier tape operatively coupled to the tablet press into the die cavity. The powdered material and the electronic device are compressing to form a tablet. A system comprises a tablet press comprising a die cavity for receiving a powdered material and an electronic device therein, an upper punch, and a lower punch. The upper and lower punches are operative to form the powdered material and the electronic device into a tablet. A tape-and-reel carrier tape is operatively coupled to the tablet press, where the carrier tape is configured for holding the electronic device. A transfer mechanism is used to transfer the electronic device from the tape carrier to the die cavity.

21 Claims, 37 Drawing Sheets

(51) Int. Cl.
  *B65B 69/00*    (2006.01)
  *B32B 37/15*    (2006.01)
  *B32B 38/00*    (2006.01)
  *B32B 38/10*    (2006.01)
  *B30B 11/34*    (2006.01)
  *A61B 5/145*    (2006.01)

(56) References Cited

U.S. PATENT DOCUMENTS

| | | |
|---|---|---|
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A * | 11/1974 | Knapp ............................ 425/110 |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenberg |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,844,076 A | 7/1989 | Lesho |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urquhart |
| 5,110,441 A | 5/1992 | Kinlen et al. |
| 5,160,885 A | 11/1992 | Hannam et al. |
| 5,167,626 A | 12/1992 | Casper et al. |
| 5,176,626 A | 1/1993 | Soehendra |
| 5,261,402 A | 11/1993 | DiSabito |
| 5,263,481 A | 11/1993 | Axelgaard et al. |
| 5,279,607 A | 1/1994 | Schentag et al. |
| 5,281,287 A | 1/1994 | Lloyd |
| 5,283,136 A | 2/1994 | Peled et al. |
| 5,305,745 A | 4/1994 | Zacouto |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil |
| 5,458,994 A | 10/1995 | Nesselbeck et al. |
| 5,485,841 A | 1/1996 | Watkin et al. |
| 5,506,248 A | 4/1996 | Nikfar et al. |
| 5,551,020 A | 8/1996 | Flax et al. |
| 5,567,210 A | 10/1996 | Bates et al. |
| 5,596,302 A | 1/1997 | Mastrocola et al. |
| 5,600,548 A | 2/1997 | Nguyen et al. |
| 5,634,468 A | 6/1997 | Platt |
| 5,645,063 A | 7/1997 | Straka et al. |
| 5,659,247 A | 8/1997 | Clements |
| 5,705,189 A | 1/1998 | Lehmann et al. |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar et al. |
| 5,833,716 A | 11/1998 | Bar-Or |
| 5,842,324 A | 12/1998 | Grosskopf et al. |
| 5,845,265 A | 12/1998 | Woolston |
| 5,862,803 A | 1/1999 | Besson |
| 5,868,136 A | 2/1999 | Fox |
| 5,925,030 A | 7/1999 | Gross et al. |
| 5,957,854 A | 9/1999 | Besson et al. |
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,038,464 A | 3/2000 | Axelgaard et al. |
| 6,042,710 A | 3/2000 | Dubrow |
| 6,047,203 A | 4/2000 | Sackner |
| 6,068,589 A | 5/2000 | Neukermans |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Nohl et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |

(56) References Cited

U.S. PATENT DOCUMENTS

| | | |
|---|---|---|
| 6,544,174 B2 | 4/2003 | West |
| 6,564,079 B1 | 5/2003 | Cory |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,951,536 B2 | 10/2005 | Yokoi |
| 6,957,107 B2 | 10/2005 | Rogers et al. |
| 6,960,617 B2 | 11/2005 | Omidian et al. |
| 6,968,153 B1 | 11/2005 | Heinonen |
| 6,977,511 B2 | 12/2005 | Patel et al. |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,083,578 B2 | 8/2006 | Lewkowicz |
| 7,116,252 B2 | 10/2006 | Teraguchi |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |

(56) References Cited

U.S. PATENT DOCUMENTS

| | | |
|---|---|---|
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo et al. |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,055,334 B2 | 11/2011 | Savage et al. |
| 8,082,919 B2 | 12/2011 | Brunnberg et al. |
| 8,131,376 B1 | 3/2012 | Faraji et al. |
| 8,207,731 B2 | 6/2012 | Moskalenko |
| 8,224,596 B2 | 7/2012 | Agrawal et al. |
| 8,271,146 B2 | 9/2012 | Heber et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,532,776 B2 | 9/2013 | Greenberg et al. |
| 8,564,432 B2 | 10/2013 | Covannon et al. |
| 8,597,186 B2 | 12/2013 | Hafezi et al. |
| 8,698,006 B2 | 4/2014 | Bealka et al. |
| 8,758,237 B2 | 6/2014 | Sherman et al. |
| 8,784,308 B2 | 7/2014 | Duck et al. |
| 8,836,513 B2 | 9/2014 | Hafezi et al. |
| 8,858,432 B2 | 10/2014 | Robertson |
| 8,932,221 B2 | 1/2015 | Colliou et al. |
| 8,945,005 B2 | 2/2015 | Hafezi et al. |
| 9,107,806 B2 | 8/2015 | Hafezi et al. |
| 9,119,918 B2 | 9/2015 | Robertson et al. |
| 9,161,707 B2 | 10/2015 | Hafezi et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | vrijens et al. |
| 2003/0023150 A1 | 1/2003 | Yokoi et al. |
| 2003/0028226 A1 | 2/2003 | Thompson |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukuda et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |

(56) References Cited

U.S. PATENT DOCUMENTS

| | | |
|---|---|---|
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura et al. |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Boric-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |

(56) References Cited

U.S. PATENT DOCUMENTS

| | | |
|---|---|---|
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boyden et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1* | 10/2009 | Schmett et al. ............... 29/428 |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers et al. |
| 2010/0033324 A1 | 2/2010 | Shimizu et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |

(56) References Cited

U.S. PATENT DOCUMENTS

| | | | |
|---|---|---|---|
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0105864 A1 | 5/2011 | Robertson et al. |
| 2011/0124983 A1 | 5/2011 | Kroll et al. |
| 2011/0224912 A1 | 9/2011 | Bhavaraju et al. |
| 2011/0230732 A1 | 9/2011 | Edman et al. |
| 2012/0016231 A1 | 1/2012 | Westmoreland |
| 2012/0059257 A1 | 3/2012 | Duck et al. |
| 2012/0062371 A1 | 3/2012 | Radivojevic et al. |
| 2012/0116359 A1 | 5/2012 | Hafezi et al. |
| 2012/0245043 A1 | 9/2012 | England |
| 2012/0299723 A1 | 11/2012 | Hafezi et al. |
| 2013/0030366 A1 | 1/2013 | Robertson et al. |
| 2013/0129869 A1 | 5/2013 | Hafezi et al. |
| 2013/0144132 A1 | 6/2013 | Hafezi et al. |
| 2015/0059922 A1 | 3/2015 | Thompson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0150480 A1 | 6/2015 | Zdeblick et al. |
| 2015/0173646 A1 | 6/2015 | Berkman et al. |
| 2015/0223751 A1 | 8/2015 | Zdeblick et al. |
| 2015/0230729 A1 | 8/2015 | Zdeblick et al. |
| 2015/0248833 A1 | 9/2015 | Arne et al. |

FOREIGN PATENT DOCUMENTS

| | | |
|---|---|---|
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| JP | 61072712 | 4/1986 |
| JP | 05-228128 | 9/1993 |
| JP | 2000-506410 | 5/2000 |
| JP | 2002263185 | 9/2002 |
| JP | 2002282219 | 10/2002 |
| JP | 2003050867 | 2/2003 |
| JP | 2004-313242 | 11/2004 |
| JP | 2005-073886 | 3/2005 |
| JP | 2005-087552 | 4/2005 |
| JP | 2005-304880 | 4/2005 |
| JP | 2005124708 | 5/2005 |
| JP | 2005514966 | 5/2005 |
| JP | 2005343515 | 12/2005 |
| JP | 2006006377 | 1/2006 |
| JP | 2006509574 | 3/2006 |
| JP | 2007-313340 | 12/2007 |
| JP | 2009514870 | 4/2009 |
| JP | 2009528909 | 8/2009 |
| KR | 2006077523 | 7/2006 |
| TW | 200406192 | 5/2004 |
| TW | 200916136 | 4/2009 |
| WO | WO8802237 | 4/1988 |
| WO | WO9221307 | 12/1992 |
| WO | WO9308734 | 5/1993 |
| WO | WO9319667 | 10/1993 |
| WO | WO9401165 | 1/1994 |
| WO | WO9739963 | 10/1997 |
| WO | WO9843537 | 10/1998 |
| WO | WO9937290 | 7/1999 |
| WO | WO9959465 | 11/1999 |
| WO | WO0033246 | 6/2000 |
| WO | WO0147466 | 7/2001 |
| WO | WO0174011 | 10/2001 |
| WO | WO0180731 | 11/2001 |
| WO | WO0245489 | 6/2002 |
| WO | WO02058330 | 7/2002 |
| WO | WO02062276 | 8/2002 |
| WO | WO02087681 | 11/2002 |
| WO | WO02095351 | 11/2002 |
| WO | WO03005877 | 1/2003 |
| WO | WO03050643 | 6/2003 |
| WO | WO03068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | WO2005110238 | 11/2005 |
| WO | WO2006021932 | 3/2006 |
| WO | WO2006027586 | 3/2006 |
| WO | WO2006028347 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006116718 | 11/2006 |
| WO | WO2006117355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |

(56) References Cited

FOREIGN PATENT DOCUMENTS

| WO | WO2007067054 | 6/2007 |
| --- | --- | --- |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2006104843 | 1/2008 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO0100085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010129288 | 11/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2015112603 | 7/2015 |
| WO | WO2015112604 | 7/2015 |
| WO | WO2015119911 | 8/2015 |

OTHER PUBLICATIONS

"ASGE Technology Status Evaluation Report: wireless capsule endoscopy" American Soc. For Gastrointestinal Endoscopy (2006) vol. 63, No. 4; 7 pp.

Aydin et al., "Design and implementation considerations for an advanced wireless interface in miniaturized integrated sensor Microsystems" Sch. of Eng. & Electron., Edinburgh Univ., UK; (2003); abstract.

Barrie, Heidelberg pH capsule gastric analysis. Texbook of Natural Medicine, (1992), Pizzorno, Murray & Barrie.

Bohidar et al., "Dielectric Behavior of Gelatin Solutions and Gels" Colloid Polym Sci (1998) 276:81-86.

Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastoenterology (2008) vol. 22, Issue 5, pp. 813-837.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Fawaz et al., "Enhanced Telemetry System using CP-QPSK Band-Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.

Ferguson et al., "Dialectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. (2002), p. 1-43.

Given Imaging, "Agile Patency Brochure" (2006) http://www.inclino.no/documents/AgilePatencyBrochure_Global_GMB-0118-01.pdf; 4pp.

Gonzalez-Guillaumin et al., "Ingestible capsule for impedance and pH monitoring in the esophagus" IEEE Trans Biomed Eng. (2007) 54(12): 2231-6; abstract.

Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.

Heydari et al., "Analysis of the PLL jitter due to power/ground and substrate noise"; IEEE Transactions on Circuits and Systems (2004) 51(12): 2404-16.

Hoeksma, J. "New 'smart pill' to track adherence" E-Health-Insider (2010) http://www.e-health-insider.com/news/5910/new_'smart_pill'_monitors_medicines.

Hoover et al., "Rx for health: Engineers design pill that signals it has been swallowed" University of Florida News (2010) 2pp.; http://news.ufl.edu/2010/03/31/antenna-pill-2/.

ISFET—Ion Sensitive Field-Effect Transistor; MICROSENS S.A. pdf document. First cited by Examiner in Office Action dated Jun. 13, 2011 for U.S. Appl. No. 12/238,345; 4pp.

Intromedic, MicroCam Innovative Capsule Endoscope Pamphlet. (2006) 8 pp (http://www.intromedic.com/en/product/productinfo.asp).

Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.

Kamada K., "Electrophoretic deposition assisted by soluble anode" Materials Letters 57 (2003) 2348-2351.

Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.

Kim et al., "A Semi-Interpenetrating Network System for a Polymer Membrane"; Eur. Polym. J. vol. 33 No. 7; pp. 1009-1014 (1997).

Li, P-Y, et al. "An electrochemical intraocular drug delivery device", Sensors and Actuators A 143 (2008) p. 41-48.

(56) References Cited

OTHER PUBLICATIONS

MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

MacKay et al., "Endoradiosonde" Nature, (1957) 1239-1240, 179 Nature Publishing Group.

McKenzie et al., "Validation of a new telemetric core temperature monitor" J. Therm. Biol. (2004) 29(7-8):605-11.

Melanson, "Walkers swallow RFID pills for science" Engadget (2008); http://www.engadget.com/2008/07/29/walkers-swallow-rfid-pills-for-science/.

Minimitter Co. Inc. "Actiheart" Traditional 510(k) Summary. Sep. 27, 2005.

Minimitter Co. Inc. Noninvasive technology to help your studies succeed. Mini Mitter.com Mar. 31, 2009.

Mini Mitter Co, Inc. 510(k) Premarket Notification Mini-Logger for Diagnostic Spirometer. Sep. 21, 1999.

Mini Mitter Co, Inc. 510(k) Premarket Notification for VitalSense. Apr. 22, 2004.

Minimitter Co. Inc. VitalSense Integrated Physiological Monitoring System. Product Description. (2005).

Minimitter Co. Inc. VitalSense Wireless Vital Signs Monitoring. Temperatures.com Mar. 31, 2009.

Mojaverian et al., "Estimation of gastric residence time of the Heidelberg capsule in humans: effect of varying food composition" Gastroenterology (1985) 89:(2): 392-7.

NPL_AntennaBasics.pdf, Radio Antennae, http://www.erikdeman.de/html/sail018h.htm; (2008) 3pp.

O'Brien et al., "The Production and Characterization of Chemically Reactive Porous Coatings of Zirconium Via Unbalanced Magnetron Sputtering" Surface and Coatings Technology (1996) 86-87; 200-206.

"RFID "pill" monitors marchers" RFID News (2008) http://www.rfidnews.org/2008/07/23/rfid-pill-monitors-marchers/.

Rolison et al., "Electrically conductive oxide aerogels: new materials in electrochemistry" J. Mater. Chem. (2001) 1, 963-980.

Roulstone, et al., "Studies on Polymer Latex Films: I. A study of latex film morphology" Polymer International 24 (1991) pp. 87-94.

Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.

Santini, J.T. et al, "Microchips as controlled drug delivery-devices", Agnew. Chem. Int. Ed. (2000), vol. 39, p. 2396-2407.

"SensiVida minimally invasive clinical systems" Investor Presentation Oct. 2009 28pp; http://www.sensividamedtech.com/SensiVidaGeneralOctober09.pdf.

Shawgo, R.S. et al. "BioMEMS from drug delivery", Current Opinion in Solid State and Material Science 6 (2002), p. 329-334.

Shin et al., "A Simple Route to Metal Nanodots and Nanoporous Metal Films"; Nano Letters, vol. 2, No. 9 (2002) pp. 933-936.

Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).

"Smartlife awarded patent for knitted transducer" Innovation in Textiles News: http://www.innovationintextiles.com/articles/208.php; 2pp. (2009).

"The SmartPill Wireless Motility Capsule" Smartpill, The Measure of GI Health; (2010) http://www.smartpillcorp.com/index.cfm?pagepath=Products/The_SmartPill_Capsule&id=17814.

Solanas et al., "RFID Technology for the Health Care Sector" Recent Patents on Electrical Engineering (2008) 1, 22-31.

Soper, S.A. et al. "Bio-Mems Technologies and Applications", Chapter 12, "MEMS for Drug Delivery", p. 325-346 (2007).

Swedberg, "University Team Sees Ingestible RFID Tag as a Boon to Clinical Trials" RFID Journal (2010) Apr. 27th; http://www.rfidjournal.com/article/view/7560/1 3pp.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.

Tatbul et al., "Confidence-based data management for personal area sensor networks" ACM International Conference Proceeding Series (2004) 72.

Tierney, M.J. et al "Electroreleasing Composite Membranes for Delivery of Insulin and other Biomacromolecules", J. Electrochem. Soc., vol. 137, No. 6, Jun. 1990, p. 2005-2006.

Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.

Walkey, "MOSFET Structure and Processing"; 97.398* Physical Electronics Lecture 20.

Watson, et al., "Determination of the relationship between the pH and conductivity of gastric juice" Physiol Meas. 17 (1996) pp. 21-27.

Whipple, Fred L.; "Endoradiosonde," Nature, Jun. 1957, 1239-1240.

Winter, J. et al. "The material properties of gelatin gels"; USA Ballistic Research Laboratories, Mar. 1975, p. 1-157.

Wongmanerod et al., "Determination of pore size distribution and surface area of thin porous silicon layers by spectroscopic ellipsometry" Applied Surface Science 172 (2001) 117-125.

Xiaoming et al., "A telemedicine system for wireless home healthcare based on bluetooth and the internet" Telemedicine Journal and e-health (2004) 10(S2): S110-6.

Yang et al., "Fast-switching frequency synthesizer with a discriminator-aided phase detector" IEEE Journal of Solid-State Circuits (2000) 35(10): 1445-52.

Yao et al., "Low Power Digital Communication in Implantable Devices Using Volume Conduction of Biological Tissues" Proceedings of the 28th IEEE, EMBS Annual International Conference, Aug. 30-Sep. 3 2006.

Zimmerman, "Personal Area Networks: Near-field intrabody communication" IBM Systems Journal (1996) 35 (3-4):609-17.

Description of ePatch Technology Platform for ECG and EMG, located it http://www.madebydelta.com/imported/images/DELTA_Web/documents/ME/ePatch_ECG_EMG.pdf, Dated Sep. 2, 2010.

Zworkin, "A Radio Pill" Nature, (1957) 898, 179 Nature Publishing Group.

Philips Respironics Products, Noninvasive Technology to Help Your Studies Succeed. 510 (k) Permanent Notification for Vital Sense. Apr. 22, 2004; http/minimitter.com/products.cfm.

Wang, X. et al "Resistance to Tracking and Erosion of Silicone Rubber Material under Various Types of Precipitation", Jpn. J. Appl. Phys. vol. 38 (1999) pp. 5170-5175.

* cited by examiner

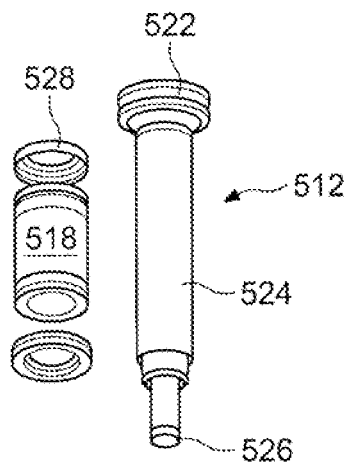
FIG. 9
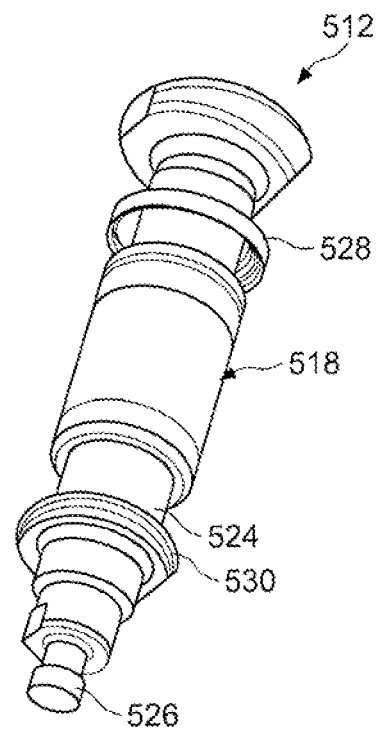
FIG. 10
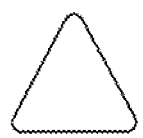 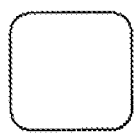 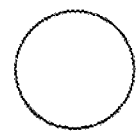
(a)     (b)     (c)
FIG. 11

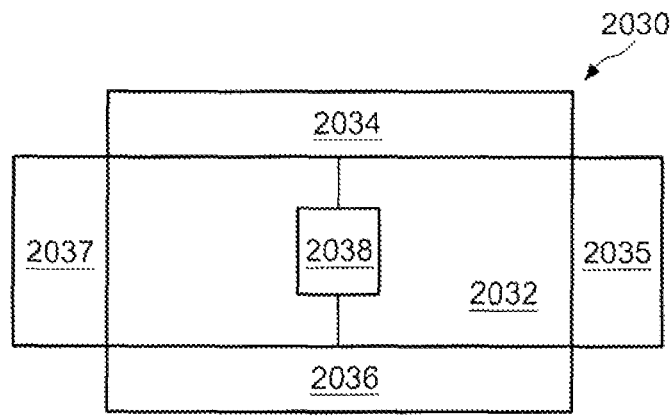
FIG. 34
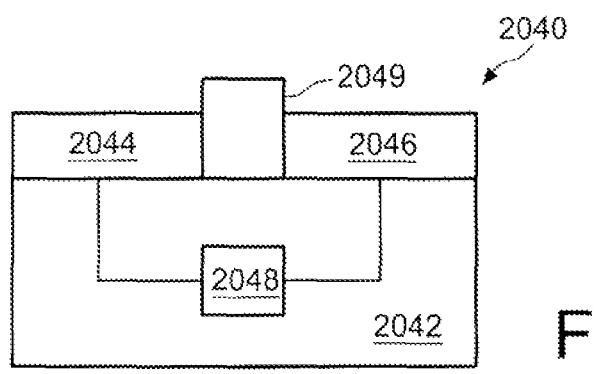
FIG. 35
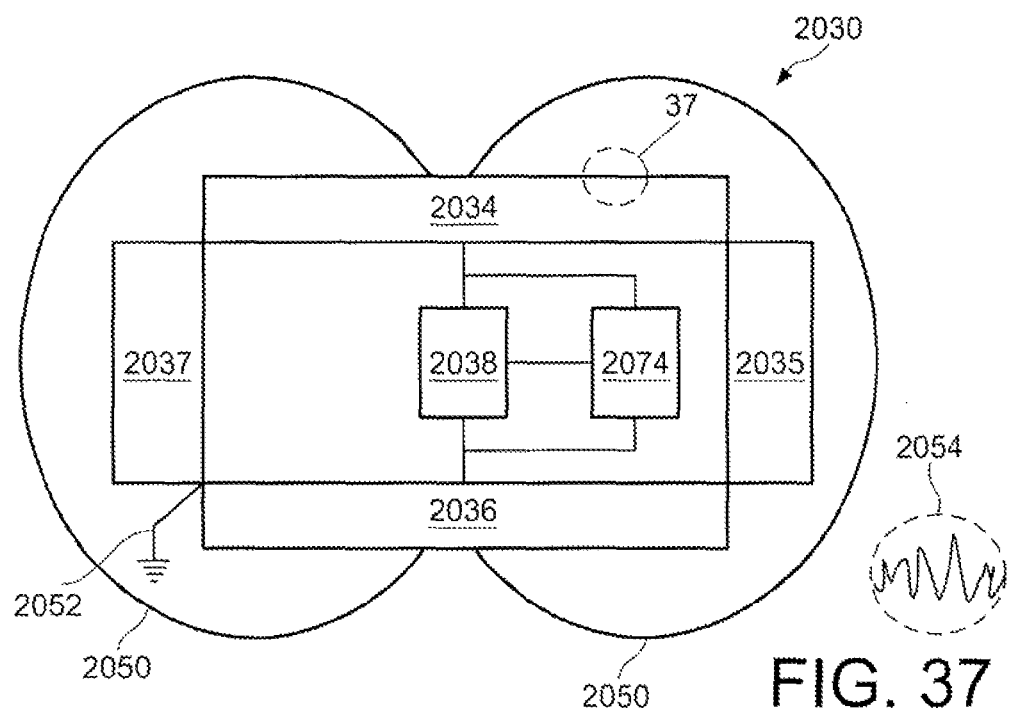
FIG. 36
FIG. 37

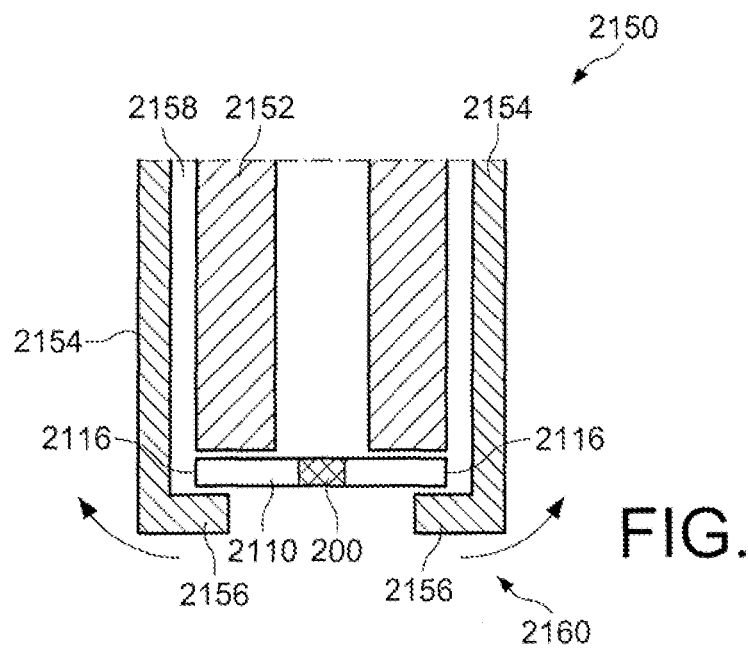
FIG. 46A
FIG. 46B
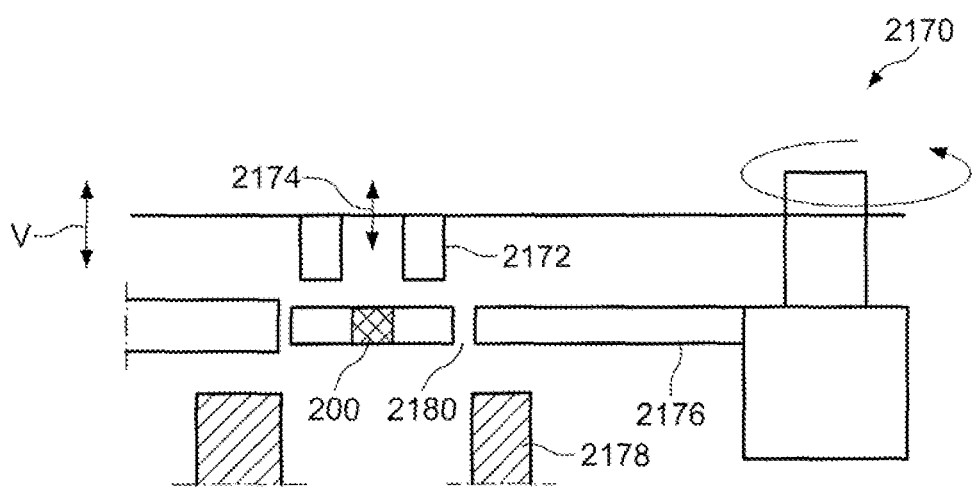
FIG. 47

TECHNIQUES FOR MANUFACTURING INGESTIBLE EVENT MARKERS COMPRISING AN INGESTIBLE COMPONENT

CROSS-REFERENCE TO RELATED APPLICATIONS

This application claims priority to International Application No. PCT/US2013/051511 filed Jul. 22, 2013, which application pursuant to 35 U.S.C. §119(e), claims priority to the filing date of U.S. Provisional Patent Application Ser. No. 61/674,851 filed Jul. 23, 2012; the disclosures of which are herein incorporated by reference.

The present application is also related to commonly assigned U.S. application Ser. No. 13/319,977 entitled INGESTIBLE EVENT MARKERS COMPRISING AN INGESTIBLE COMPONENT, filed May 10, 2010; U.S. application Ser. No. 13/319,309 entitled INTEGRATED INGESTIBLE EVENT MARKER SYSTEM WITH PHARMACEUTICAL PRODUCT, filed Dec. 2, 2010; International Application No. PCT/US2011/031536 entitled MINIATURE INGESTIBLE DEVICE, filed Apr. 4, 2011; and International Application No. PCT/US2011/061478, entitled INGESTIBLE DEVICE WITH PHARMACEUTICAL PRODUCT, filed Nov. 18, 2011; each of which is incorporated herein by reference in its entirety.

INTRODUCTION

Various embodiments are disclosed that relate to manufacturing electronic devices with partial power sources and, more specifically, to electronic devices secured to a tablet wherein the electronic devices are activated upon contact with a conducting fluid.

Pharmaceutical products are delivered to a user in many forms, including a pill. Integration of a pharmaceutical product with an ingestible device into a tablet is often a challenge due to the delicate nature of the electronic components as well as the difficulty in securing the electronic components to the pharmaceutical product, such as a pill, tablet, capsule. For example, tablets are typically made using a press that applies pressure to a powder form. Handling a small electronic device is often a challenge during the assembly process. Therefore, what is needed is a technique for handling a small ingestible electronic device and attaching the device to a pharmaceutical product such as a tablet without damaging the ingestible electronic device.

SUMMARY

In one aspect, a method of manufacturing a tablet comprising an electronic device is provided. The method comprises providing a powdered material into a die cavity of a tablet press; dispensing an electronic device from a tape-and-reel carrier tape operatively coupled to the tablet press, the carrier tape configured for holding the electronic device; locating the electronic device into the die cavity; and compressing the powdered material and the electronic device to form a tablet.

In another aspect, a system for manufacturing a tablet comprising an electronic device is provided. The system comprises a tablet press comprising a die cavity for receiving a powdered material and an electronic device therein, an upper punch, and a lower punch, wherein the upper and lower punches are operative to form the powdered material and the electronic device into a tablet; a tape-and-reel carrier tape operatively coupled to the tablet press, the carrier tape configured for holding the electronic device; and a transfer mechanism to transfer the electronic device from the tape carrier to the die cavity.

FIGURES

FIG. 9 shows an exploded perspective view of one aspect of a lower upper punch with guiding sleeve and sealing rings.

FIG. 10 shows a perspective view of one aspect of an assembly of the upper stamp with sleeve and sealing rings according to FIG. 9.

FIG. 11 shows different cross sections for the punch shafts.

FIG. 34 is a block diagram representation of one aspect of the event indicator system with dissimilar metals positioned on opposite ends.

FIG. 35 is a block diagram representation of another aspect of the event indicator system with dissimilar metals positioned on the same end and separated by a non-conducting material.

FIG. 36 shows ionic transfer or the current path through a conducting fluid when the event indicator system of FIG. 34 is in contact with conducting liquid and in an active state.

FIG. 37 shows an exploded view of the surface of dissimilar materials of FIG. 36.

FIG. 46A is a cross-sectional view of one aspect of a pick-and-place transfer mechanism holding an electronic device within a mechanical gripper 2154.

FIG. 46B is a bottom view of the pick-and-place transfer mechanism holding an electronic device shown in FIG. 46A.

FIG. 47 illustrates one aspect of a friction hold disc technique for handling an electronic device.

Figure 70:
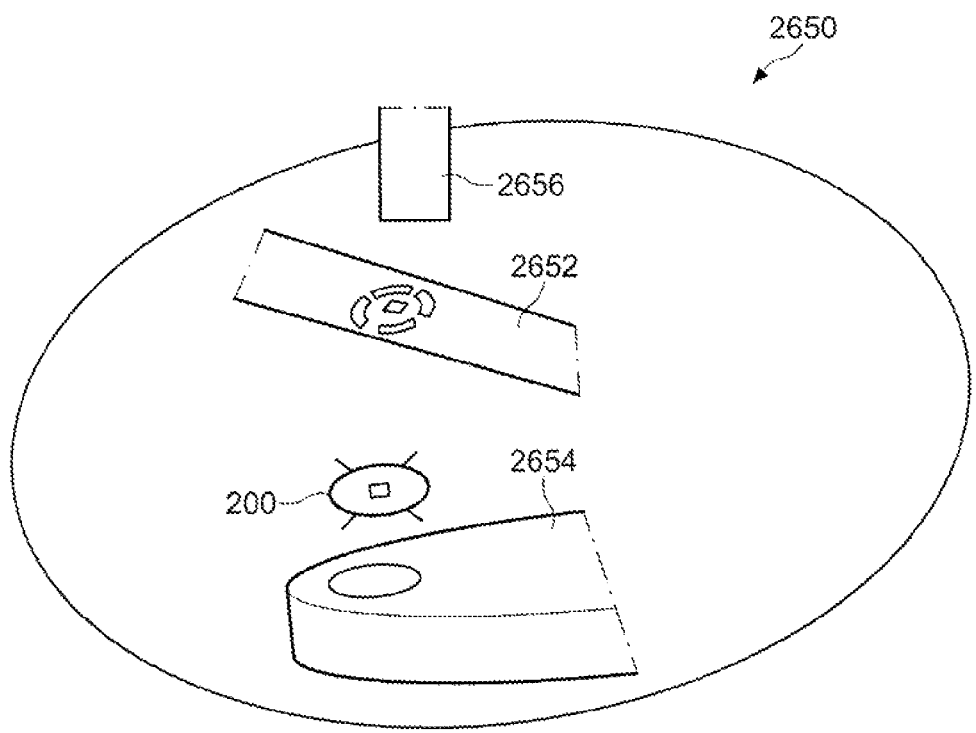
FIG. 70 illustrates one aspect of a transfer mechanism comprising a pre punched film/carrier tape that holds the electronic device so that punching the electronic device out into the press tool with a punch can be facilitated.
Figure 71:
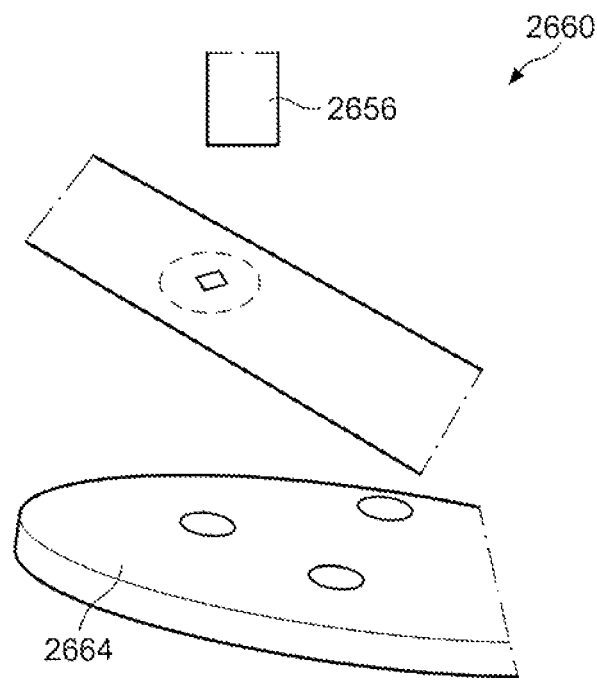
Figure 72:
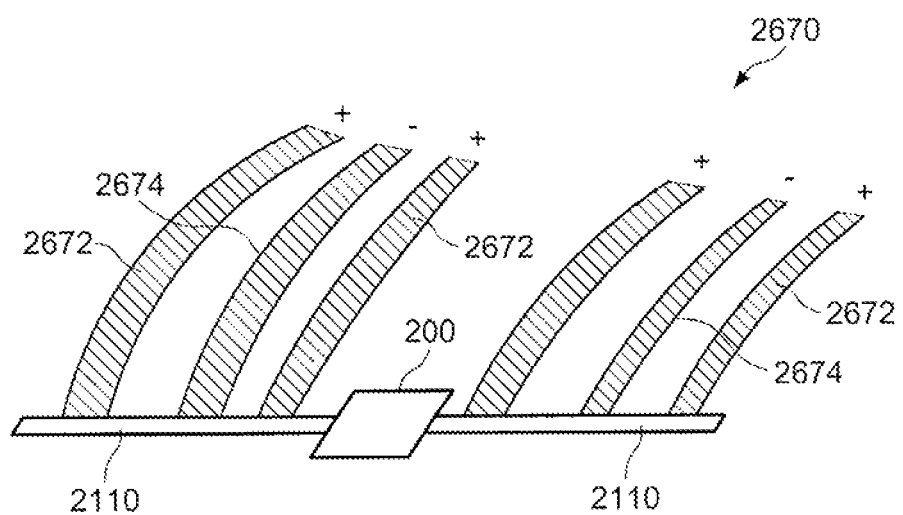

FIG. 71 illustrates one aspect of a transfer mechanism as shown in FIG. 70 except that the punch occurs into a rotating plate that may hold the electronic device with a friction fit around the perimeter, or have some mechanical feature to lock in place FIG. 72 illustrates a transfer mechanism comprising electrically charged pick-up head with fingers having opposite charge to grab the electronic device and hold the electronic device in place by electrostatic forces.

Notwithstanding the claims, the invention is also referred to in the following clauses:

1. A method of manufacturing a tablet comprising an electronic device, the method comprising:
   providing a powdered material into a die cavity of a tablet press;
   dispensing an electronic device from a tape-and-reel carrier tape operatively coupled to the tablet press, the carrier tape configured for holding the electronic device;
   locating the electronic device into the die cavity; and
   compressing the powdered material and the electronic device to form a tablet.
2. The method of clause 1, further comprising one or more of the following steps:
   pre-compressing the powdered material prior to locating the electronic device into the die cavity,
   providing additional powdered material into the die cavity after forming the tablet.
   compressing the additional powdered material to form the tablet.
3. The method of any of the preceding clauses with one or more of the following:
   wherein the tablet press is a rotary tablet press.
   wherein the powdered material is a pharmaceutical material.
   wherein the electronic device is an ingestible event marker.
4. The method of any of the preceding clauses wherein the carrier tape comprises a cover tape and defines a cavity for holding the electronic device between the cavity and the cover tape, wherein dispensing the electronic device from the carrier tape comprises:
   removing the cover tape from the carrier tape to expose the electronic device within the cavity;
   transferring the cover tape to a pick-and-place transfer mechanism;
   picking the electronic device from the cavity with a pick-and-place element of the transfer mechanism, wherein the pick-and-place element is preferably a vacuum tool,
   transferring the pick-and-place element to the tablet press; and
   placing the electronic device in the die cavity.
5. The method of clause 6, further comprising locating the pick-and-place element above the die cavity.
6. The method of clause 4 or 5 further comprising:
   transferring the pick-and-place element to a carrier;
   locating the pick-and-place element above the carrier;
   placing the electronic device in the carrier;
   picking the electronic device from the carrier with a second pick-and-place element of a second transfer mechanism; and
   locating the second pick-and-place element above the die cavity.
7. The method of any of the preceding clauses wherein dispensing the electronic device from the tape carrier comprises:
   transferring the carrier tape to a punch press;
   punching through the carrier tape comprising the electronic device with an ejector pin portion of the punch press, wherein the ejector pin perforates the carrier tape; and
   dispensing the electronic device into the die cavity through the perforations.
8. The method of clause 7, further comprising:
   dispensing the electronic device into a carrier; and
   transferring the carrier to the tablet press, preferably wherein the carrier frictionally engages the electronic device and centers the electronic device with the die cavity.
9. The method of any of the preceding clauses wherein the carrier tape carrier comprises first and second adhesive tapes for holding the electronic device therebetween, wherein dispensing the electronic device from the carrier tape comprises:
   removing the first adhesive tape from the carrier tape to expose the electronic device within the cavity;
   transferring the cover tape to a punch press;
   punching through the carrier tape comprising the electronic device with an ejector pin portion of the punch press, wherein the ejector pin perforates the carrier tape; and
   dispensing the electronic device into the die cavity through the perforations, and preferably further comprising the steps of dispensing the electronic device into a carrier; and
   transferring the carrier to the tablet press.
10. A system for manufacturing a tablet comprising an electronic device, the system comprising:
    a tablet press comprising a die cavity for receiving a powdered material and an electronic device therein, an upper punch, and a lower punch, wherein the upper and lower punches are operative to form the powdered material and the electronic device into a tablet;
    a tape-and-reel carrier tape operatively coupled to the tablet press, the carrier tape configured for holding the electronic device; and
    a transfer mechanism to transfer the electronic device from the tape carrier to the die cavity.
11. The system of clause 17, wherein the transfer mechanism comprises a pick-and-place transfer mechanism operatively coupled to the carrier tape and the tablet press.
12. The system of clause 10 or 11 further comprising a carrier to receive the electronic device and center the electronic device relative to the die cavity, wherein the pick-and-place transfer mechanism locates the electronic device in the carrier.
13. The system of clause 12, further comprising a second pick-and-place transfer mechanism to pick the electronic device from the carrier, locate the second pick-and-place transfer mechanism above the die cavity, preferably wherein the first and/or second pick-and-place transfer mechanism comprises a vacuum tool.
14. The system of any of the preceding clauses 10-13 further comprising a punch press for dispensing the electronic device from the tape carrier operatively coupled to the tablet press, preferably wherein the punch press comprises a rotating punch wheel, and/or wherein the carrier tape carrier comprises first and second adhesive tapes for holding the electronic device therebetween.
15. Use of a system according to any of the preceding clauses 10-14 in a process according to any of the preceding clauses 1-9.

DESCRIPTION

The present disclosure is directed generally to various techniques are disclosed for handling an electronic device and integrating the handling process with a press process used in manufacturing a pill, tablet, or capsule. The technique includes a system and method for securing an ingestible electronic device to a pharmaceutical product in a tablet form in a press process without damaging the ingestible electronic device. The techniques include a process for manufacturing a product comprising the electronic device and a pharmaceutical agent that integrates with a tablet press, such as, for example, a rotary tablet press described hereinbelow. The techniques described herein, however, are not limited to a rotary tablet press.

Tape and reel packaging provides a compact means for storing, transporting, and dispensing integrated circuits. The reel is placed directly onto a relatively small piece of equipment for picking and placing the circuits, and as a result this type of handling equipment has become much more desirable to the end user than the more bulky x/y table used to pick-and-place from trays.

Consequently, a need for packing reels and an assemblage which is compatible with dry baking integrated circuit devices has developed. Simply using existing reels constructed of high temperature plastic has not been successful because the design is inefficiency for baking, and because high temperature plastics are generally more dense, thus resulting in additional shipping weight.

A lightweight packing reel for storing encapsulated semiconductor devices which may be baked for extended periods of time at temperatures sufficiently high to desorb moisture from the packages, and which allows efficient flow of heat and air through the tape and reel assemblage is provided.

In the manufacture of large-scale electronic devices, it is necessary to package the electronic devices in a way which minimizes handling, and which minimizes potential damage to the electronic devices. When large numbers of identical electronic devices are required, the electronic devices frequently are packaged in elongated strips of sealed "pocket tape."

Figure 1:
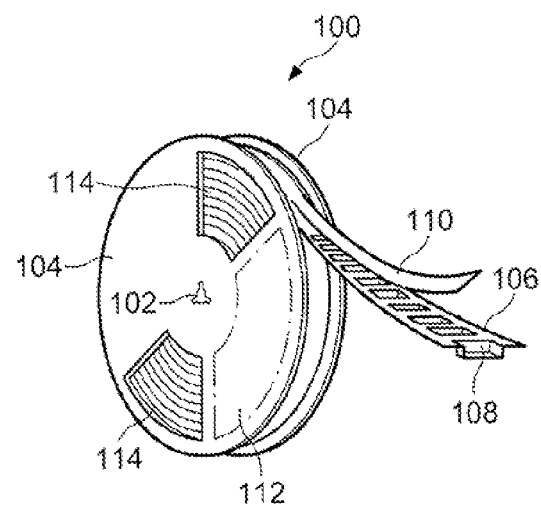
FIG. 1 is a perspective view of one aspect of a tape and reel assemblage for storing electronic devices.

FIG. 1 illustrates a schematic of one aspect of a tape and reel packing assemblage with a reel 100 having a hub 102 and parallel flanges 104, a carrier tape 106 with cavities 108, and a cover tape 110. The reel 100, generally constructed of plastic, provides areas on the flange where labels 112 can be placed to provide information pertaining to the electronic devices. Large openings called windows 114 in the flange are not specified, but may exist to provide a convenient means to grasp the reel. The carrier tape 106 is made of a flexible plastic material in which a series of adjacent pockets or cavities 108 are formed. The size of the cavity 108 is selected to accommodate correspondingly-sized electronic devices, with one electronic device typically being placed in each cavity 108. The cavities 108 are arranged to run the length of the carrier tape 106, which also typically includes perforated flanges along each edge of the tape for utilization in indexing machines, where the electronic devices subsequently are removed from the carrier tape 106. The cavities 108 in the carrier tape 106 can be formed by punching, embossing, thermoforming, or other techniques. The cover tape 110 has a heat or pressure sensitive adhesive on predefined sealing areas which attaches to the carrier tape, and holds the electronic device securely in the cavity 108.

The electronic devices may be automatically vacuum loaded into each cavity 108 in the carrier tape 106, the tape 106 indexed to the next position, a cover tape 110 sealed onto the loaded cavity 108, and the tape 106 indexed onto the reel 100. For unloading, the procedure may be reversed.

At the manufacturer of the electronic devices, the carrier tape 106 is moved along while the devices are inserted, and then a releasable cover tape 110 is sealed to the carrier tape 106 along the edges of the different cavities 108 to hold the electronic devices securely in the cavity 108. After this is done, the sealed carrier tape 106 is rolled up on reels 100 for delivery. The orientation of the electronic devise in the cavities 108 of the reels 100 follows according to specifications of the particular device package. Normally, inspection of the orientation of the electronic packages in the cavities 108 of the carrier tape may involve visual monitoring by an operator or machine monitoring using a suitable sensing technique, such optical inspection which is less prone to human error.

Figure 2:
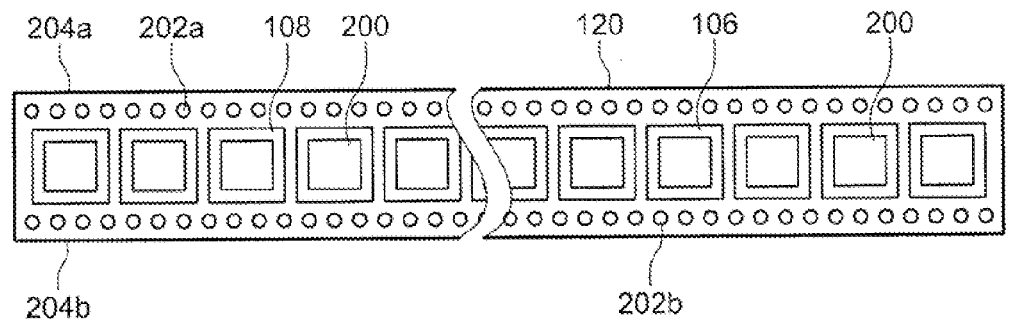
FIG. 2 is an illustration of one aspect of a carrier tape with the cover tape removed to show an electronic device located within each of the cavities of the carrier tape.

FIG. 2 is an illustration of one aspect of the carrier tape 106 with the cover tape 110 removed to show the electronic device 200 located within each of the cavities 108 of the carrier tape 106. The size of the cavity 108 is selected to accommodate correspondingly-sized electronic devices 200, with one electronic device 200 being placed in each of the cavities 108. The cavities 108 are arranged to run the length of the carrier tape 106, which includes perforated flanges 202a, 202b along each corresponding edge 204a, 204b of the carrier tape 106 for utilization in indexing machines, where the electronic devices 200 subsequently are removed from the carrier tape 106.

In one aspect, the electronic device 200 may be activated upon contact with a conducting fluid. The scope of the present disclosure, however, is not limited by the environment or type of the conducting fluid. Once ingested, the electronic device 200 comes into contact with a conducting fluid, such as stomach fluids, and the device 200 is activated. Referring again to the instance where the device 200 is used with the product that is ingested by the living organism, when the product that includes the device 200 is taken or ingested, the device 200 comes into contact with the conducting liquid of the body and a voltage potential is created and the system is activated. A portion of the power source is provided by the device 200, while another portion of the power source is provided by the conducting fluid.

Figure 3:
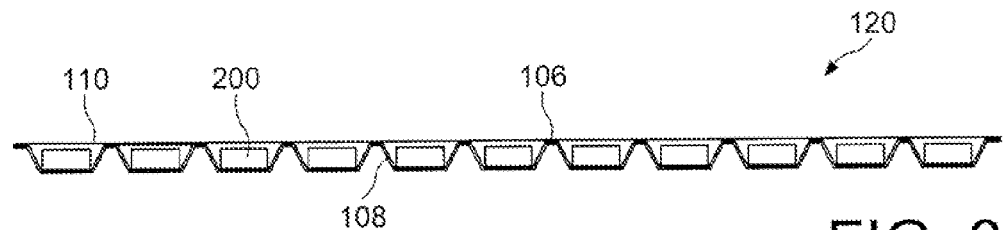
FIG. 3 is a side view of one aspect of a carrier tape comprising a cover tape and an electronic device located within each of the cavities of the carrier tape.

FIG. 3 is a side view of one aspect of the carrier tape 106 comprising the cover tape 110 and an electronic device 200 located within each of the cavities 108 of the carrier tape 106.

Figure 4:
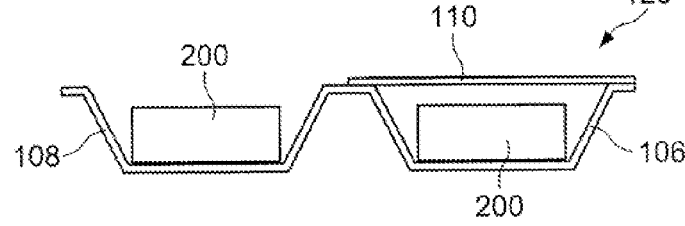
FIG. 4 is a side view of one aspect of a carrier tape showing one cavity with the cover tape located over the cavity to secure the electronic device located within each of the cavities and one cavity with the cover tape removed to expose the electronic device for removal from the carrier tape.

FIG. 4 is a side view of one aspect of the carrier tape 106 showing one cavity with the cover tape 110 located over the cavity 108 to secure the electronic device 200 located within each of the cavities 108 and one cavity 108 with the cover tape 110 removed to expose the electronic device 200 for removal from the carrier tape 106. The electronic device 200 may be removed from the carrier tape 106 using a variety of techniques including, without limitation, pick and place components, actuators, punch portion, peeled off tape, conveyor, gravity feed, air pressure, laser cuts, die ejection, among other techniques. Pick and place components include, without limitation, vacuum tools, adhesion, gripper. Once dispensed, the electronic devices 200 can be provided to a subsequent process, such as a rotary tablet press process, by a transfer wheel, conveyor, pick and place components, actuators, hopper, gravity feed, vibratory feed, punched into rotary tablet press, slide/ramp, or air pressure.

In one aspect, the reel 100 described in connection with FIGS. 1-3, may be configured such that the carrier tape 106 or the cover tape 110 can be perforated by a punch press to eject the electronic component 200. In such aspects, the cover tape 110, for example, which may be laminated onto the carrier tape 106, may be reinforced and may have a thickness that is minimal in comparison to the thickness of the ultimate tablet product. In addition, the cover tape 110 may be made of a biocompatible material that is soluble in a liquid such as water and has low mechanical strength. In one aspect, the liquid soluble biocompatible material may be fast dissolving when exposed to a liquid. In other examples, the cover tape 110 may be formed of a non-liquid soluble material. In such cases, the cover tape 110 may be porous to allow liquid ingress.

Figure 5:
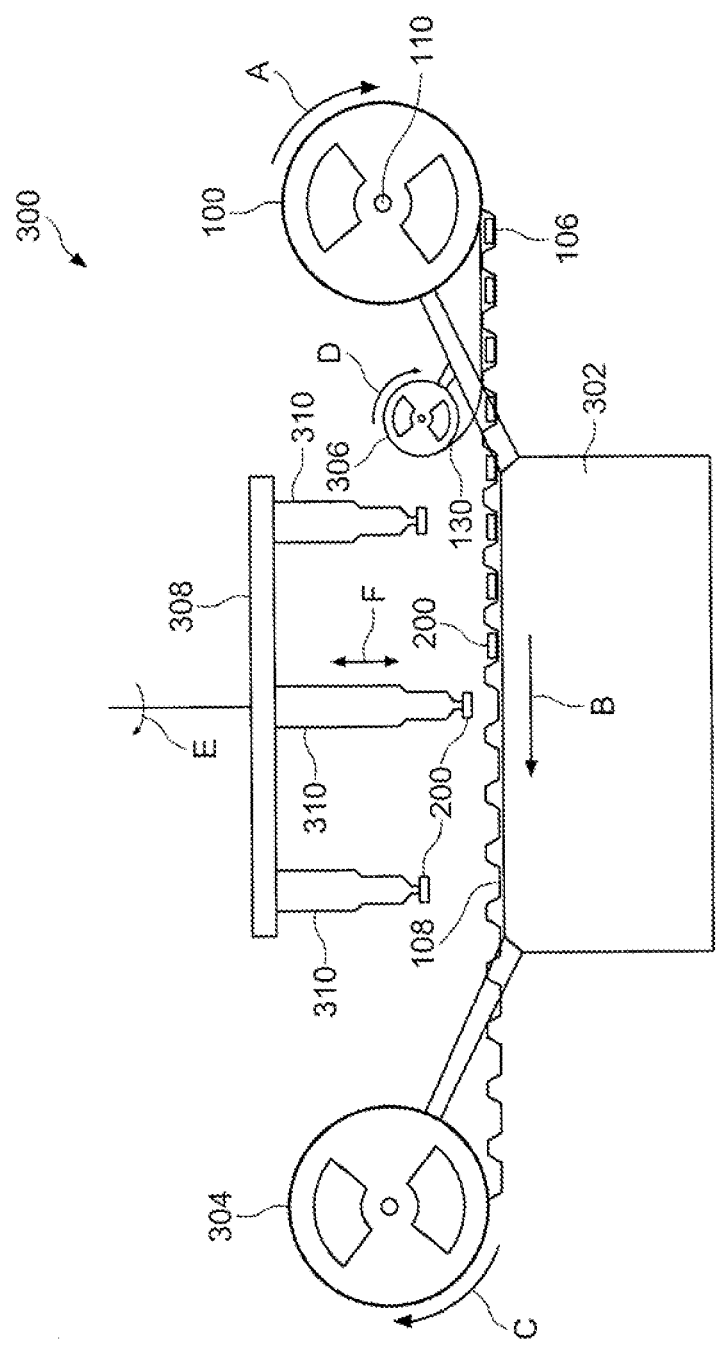
FIG. 5 illustrates a schematic of one aspect of a tape and reel feed mechanism with a reel 100 having a hub, a carrier tape with cavities, and a cover tape.

FIG. 5 illustrates a schematic of one aspect of a tape and reel feed mechanism 300 with a reel 100 having a hub 102, a carrier tape 106 with cavities 108, and a cover tape 110. In order to dispense the carrier tape 106 from right to left in direction B, the reel 100 is rotatably unwound in direction A. The carrier tape 106 moves along a guide rail 302 and wound by a second reel 304 in direction C. A third reel 306 is wound in direction D and is used to wind the cover tape 110 as it is removed from the carrier tape 106 to expose the electronic device 200 located within the cavity 108 of the carrier tape 106. After the cover tape 110 is removed from the carrier tape 106, the electronic device 200 is exposed and passes below a rotary pick-and-place transfer mechanism 308. The rotary pick-and-place transfer mechanism 308 rotates in direction E and includes multiple suction (vacuum) based pick-and-place elements 310 that move in direction F to pick an electronic device 200 from the carrier tape 106 cavity 108. Once the pick-and-place element 310 secures the electronic device 200, the rotary pick-and-place transfer mechanism 308 rotates in direction E and the carrier tape 106 advances (feeds) in direction B such the next pick-and-place element 310 rotates into position and lowers to pick up the next electronic device 200 in the carrier tape 106. The rotary pick-and-place transfer mechanism 308 can be interfaced with a rotary tablet press to secure an ingestible electronic device to a pharmaceutical product into a tablet form in without damaging the ingestible electronic device as discussed hereinafter. It will be appreciated that any suitable robotic electronic component transfer mechanism maybe employed to transfer the electronic device 200 from the carrier tape 106 to a rotary tablet press.

Figure 6:
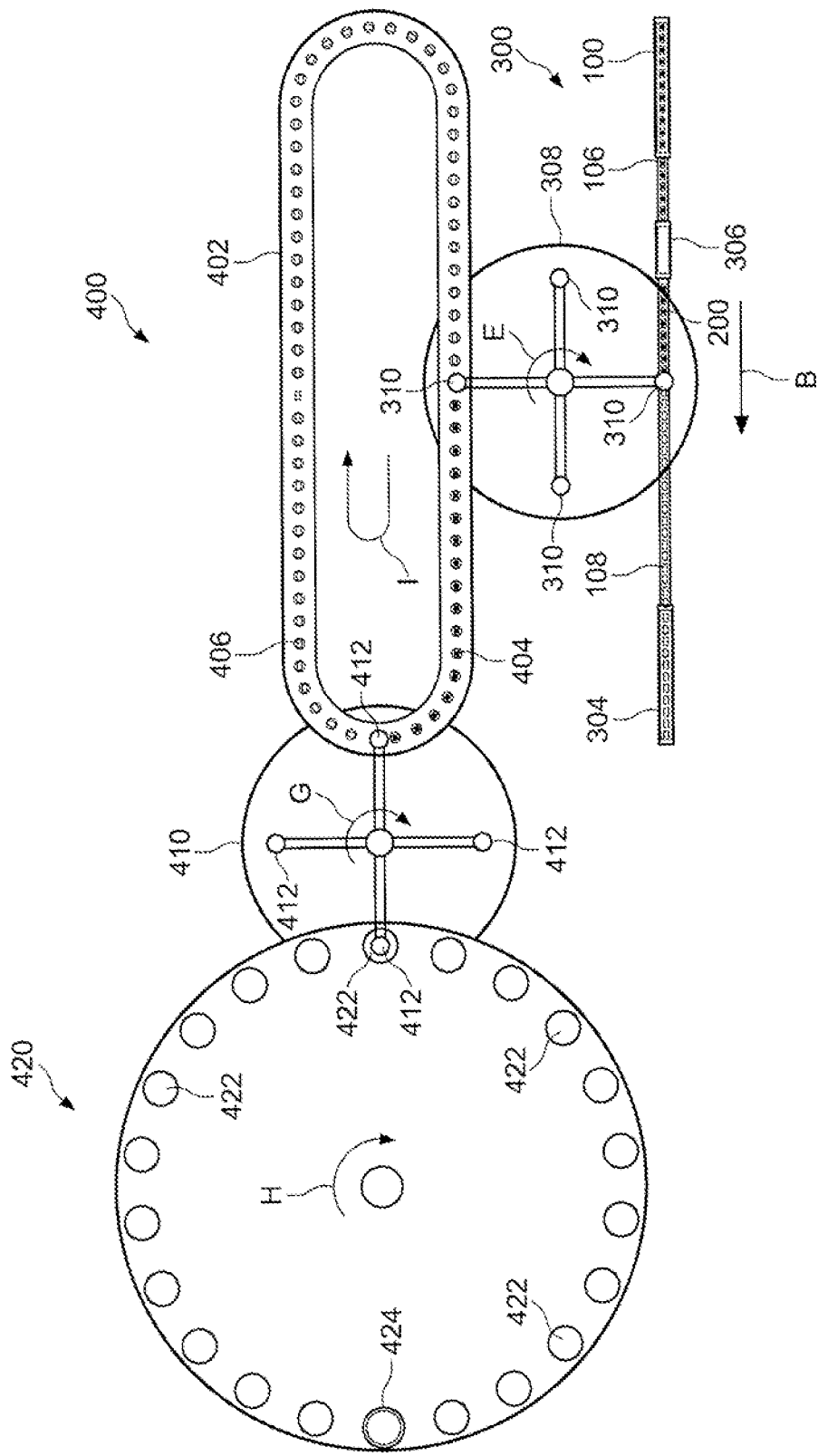
FIG. 6 illustrates one aspect of an assembling apparatus for compressing an electronic device with a powdered material into a tablet.

FIG. 6 illustrates one aspect of an assembling apparatus 400 for compressing an electronic device with a powdered material into a tablet. In one aspect, the assembling apparatus 400 comprises a tape and reel feed mechanism 300 operatively coupled to a rotary punch press 420. The tape and reel feed mechanism 300 interfaces with a conveyor system 402 moving in direction I. As shown, the tape and reel feed mechanism 300 as described in connection with FIG. 5, comprises a pick-and-place transfer mechanism 308 to pick electronic devices 200 fed by the tape and reel feed mechanism 300 and place the electronic devices 200 in a carrier 404 located on the conveyor system 402. The carrier 404 includes a compartment 406, which is dimensioned to frictionally hold the electronic device 200 until a second rotary pick-and place machine 410 transfer the electronic device 200 from the carrier 404 to the rotary punch press 420. The second rotary pick-and-place transfer mechanism 410 rotates in direction G and includes multiple suction (vacuum) pick-and-place elements 412 to pick electronic devices 200 from the carrier 404 and place them in a die cavity 422 (punch cavity) of the rotary punch press 420, which has been pre filled with a powdered material, e.g., a powdered pharmaceutical product.

The rotary punch press 420 rotates in direction H as shown. The press 420 includes a die cavity 422 and an ejection tray (not shown). A powdered material is deposited into the die cavity 422 and may be tamped or pre-compressed. The press 420 rotates to another position, which is positioned below a pick-and-place element 412 of the pick-and-place transfer mechanism 410 to receive the electronic device 200 in the die cavity 422 that includes the powdered material.

In various aspects, the carrier 404 may be configured to center the electronic component 200 to properly align the electronic device with the die cavity 422. Thus, the carrier 404 may be configured to align the electronic device 200 with the center of the die cavity 422. This process may be assisted by vision guidance systems, pick-and-place tip designs, or other suitable mechanical configurations. Additional features include features formed on the electronic device 200 to enable suitable placement of the electronic device 200 relative to the die cavity 422.

Some of these configurations include providing a flexible membrane on the electronic device that includes a plurality of legs that engage the wall of the carrier 404 when the electronic device 200 and the powdered material in the die cavity 422 are pressed into a tablet. In various aspects, the electronic device 200 may be placed within the carrier 404 and in other aspects the electronic device 200 may be secured within the carrier using friction, ingestible glues, pressure sensitive adhesives, thermal adhesives, mechanically attachment, secured to a band that is later placed around the tablet.

Referring again to FIG. 6, the rotary punch press 420 comprises a punch portion 424 to form a tablet from a powdered material and the electronic device 200 by compression or tamping. The rotary punch press 420 is activated each time a die cavity 422 containing a powdered material and an electronic device 200 passes below the punch portion 424. A completed tablet comprising the electronic device is eventually ejected from the rotary punch press 420 and moved to a collection point through an ejection tray (not shown) for further processing, such as coating layers as needed. Examples of an ejection tray is discussed in commonly assigned International PCT US Patent Application No. 2012/0116359 titled "Integrated Ingestible Event Marker System With Pharmaceutical Product," which is incorporated herein by reference in its entirety.

Figure 7:
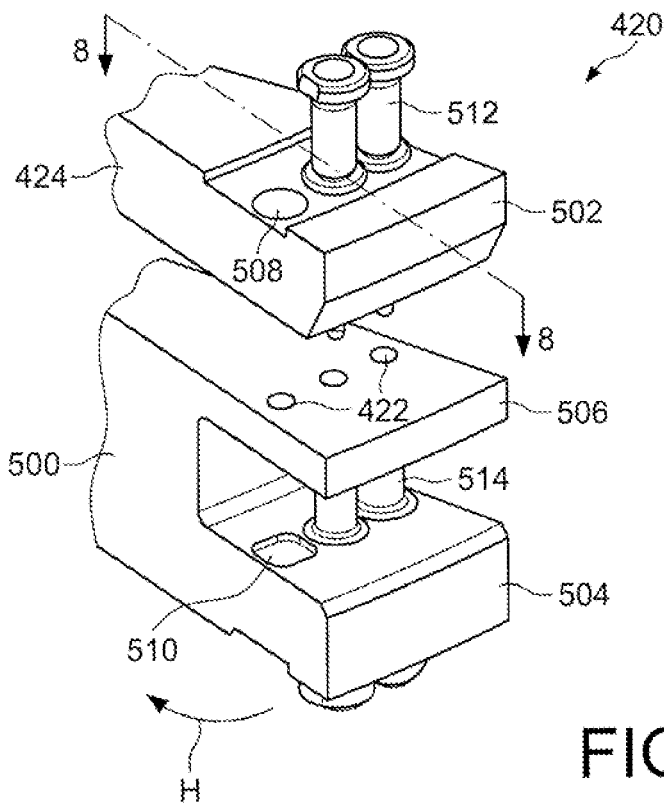
FIG. 7 is a perspective view of one aspect of a portion of one aspect of a rotor of the rotary tablet press shown in FIG. 6.
Figure 8:
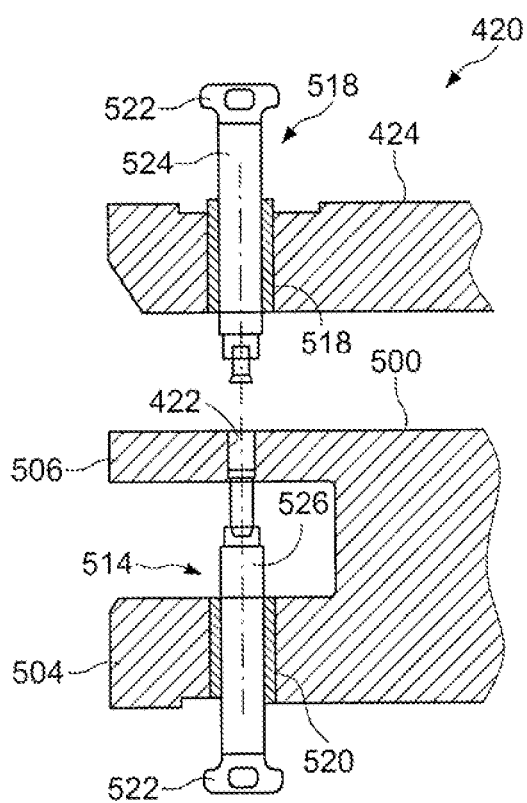
FIG. 8 shows a section through the arrangement according to FIG. 7, along the line 8-8.

FIG. 7 is a perspective view of one aspect of a portion of a rotor 500 of the rotary punch press 420 shown in FIG. 6. FIG. 8 shows a section through the arrangement according to FIG. 7, along the line 8-8. Generally, the rotary punch press 420 comprises a rotor portion 500 and punch portion 424. When the rotor 500 is aligned with the punch portion 424, upper and a lower punch guides for upper and lower punches co-operate with die cavity 422 bores in a die plate 506 which is arranged between the upper and the lower punch guides. The punches have shafts, which are sealedly axially movable in guiding bores of the punch guides by means of a sealing arrangement.

Turning now to FIGS. 7 and 8, in one aspect, the rotary punch press 420, from which only a cut-out is shown in FIG. 7, has an upper punch guide 502 and a lower punch guide 504, as well as a die plate 506 between the upper and the lower punch guiding 502, 504. In the illustrated example, the rotary punch press 420 is formed of plural pieces where the upper punch portion 424 is stationary and the lower rotor 500 portion rotates in direction H. In other aspects, the punch portion 424 and the rotor 500 may be formed as a unit in one single piece. The die plate 506 in particular may comprise individual segments.

The upper punch guide 502 has accommodation bores 508, and the lower punch guide 504 has accommodation bores 510. The punch guides 502, 504 guide in a pair-wise fashion upper punches 512 and lower punches 514, which co-operate with die bores 516 of the die plate 506 in order to press together powder-shaped material (e.g., the powdered material) and the electronic device 200 in the die cavities 422.

As shown in FIG. 8 in particular, the accommodation bores 508, 510 receive guiding sleeves 518, 520. FIG. 9 shows the upper and lower punches 512, 514 with the respective guiding sleeves 524, 526 and sealing rings 528, 530, in an exploded perspective view. FIG. 10 shows the assembly of the upper stamp with sleeve 518, and sealing rings according to FIG. 9, in a perspective view. In FIG. 9, the upper and lower punches 512, 514 and guiding sleeves 518, 520 are depicted. FIG. 11 shows different cross sections for the punch shafts. The pressing punches 512, 514 have a head 522, a shaft 524 and a tool portion 526. Only the tool portion 526 co-operates with the die bores 516 (in the following, only the upper punch 512 is treated, wherein the lower punch 514 is to be regarded in the same way). The head 522 is essentially standardized in its topside. It co-operates with not shown pressing rollers, which press the upper punch 512 into the die bore 516 against the material which is to be pressed, e.g., the pharmaceutical powder and electronic device. The shaft 524 may have an out of round cross section. In FIG. 11, cross section shapes are exemplified. FIG. 11a shows a triangular cross section, FIG. 11b a square one, and FIG. 11c a cross section which is composed of three circle sections, wherein the transitions are rounded. The guiding sleeves 518, 520, which can consist of ceramic material and which are glued into the accommodation bores 508 and 510, respectively, have a cross section which is complementary to the cross section of the shafts 524. For this reason, the described cross sections fix the rotational position of the punches 512, 514 in the punch guiding 502 or 504, respectively. An upper sealing ring 528 and a lower sealing ring 530 is associated to each punch 512, 514 and to each guiding sleeve 518, 520 respectively.

The rotary punch press 420 described in connection with FIGS. 7-11 may be embodied in many different forms, there are described in detail merely as a specific embodiment example and this description is not intended to limit the claimed subject matter to the particular aspect illustrated.

Figure 12:
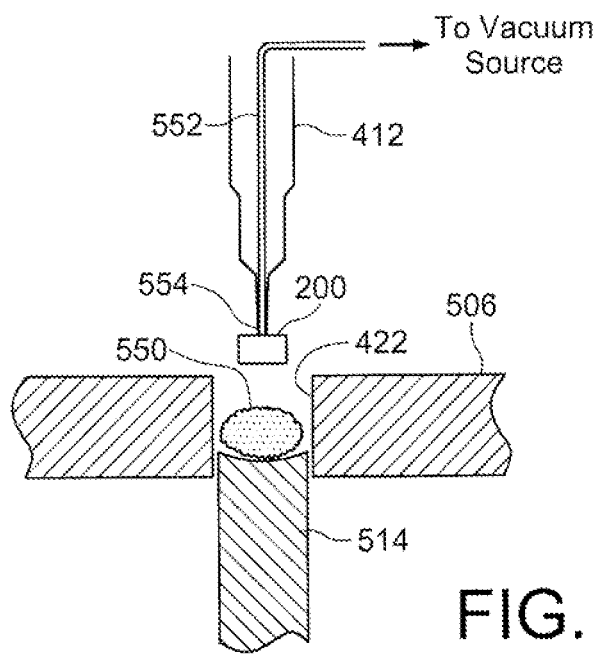
FIG. 12 is a diagram of one aspect of a suction (vacuum) pick-and-place element transferring an electronic device in a die cavity of a die plate.

FIG. 12 is a diagram of a suction (vacuum) pick-and-place element 412 transferring an electronic device 200 in a die cavity 422 of a die plate 506. The die cavity 422 includes a powdered material 550, e.g., powdered pharmaceutical, which has been tamped or pre-compressed and which will be compressed together with the electronic device 200 into a tablet. The pick-and-place element 412 includes a vacuum line 552 coupled to a vacuum source. To pick up an electronic device 200, the tip 554 of the pick-and-place element 412 is placed in contact with a top surface of the electronic device 200 and the vacuum source is turned on. Once the pick-and-place element 412 is aligned with the die cavity 422, the vacuum source is turned off and the electronic device 200 falls into the die cavity 422 and is positioned above the pre-compressed powdered material 550.

Figure 13:
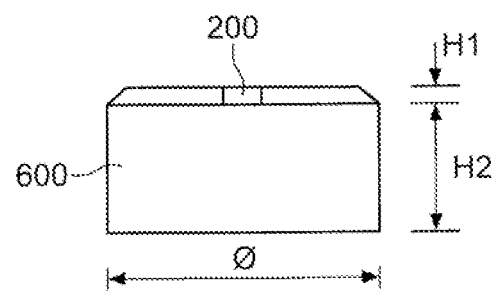
FIG. 13 illustrates one aspect of a low profile carrier tablet for use with a tablet press, such as the rotary punch press.

FIG. 13 illustrates one aspect of a low profile carrier tablet 600 for use with a tablet press, such as the rotary punch press 420. The low profile carrier tablet 600 is combined with an electronic device 200. The low profile carrier tablet 600 may have a diameter φ of about 2 to 6 mm and a thickness H2 of about 300 μm to about 3 mm. The electronic device 200 may have a diameter comparable with the low profile carrier tablet 600 and a thickness H1 of about 300 μm. The low profile carrier tablet 600 comprises a low tack adhesive applied to the surface that receives the electronic device 200 for rapid separation of the carrier 600 and the electronic device 200 when exposed to a liquid (e.g., water). Also, the carrier 600 is formed of a material for fast dissolution in the liquid.

Figure 14:
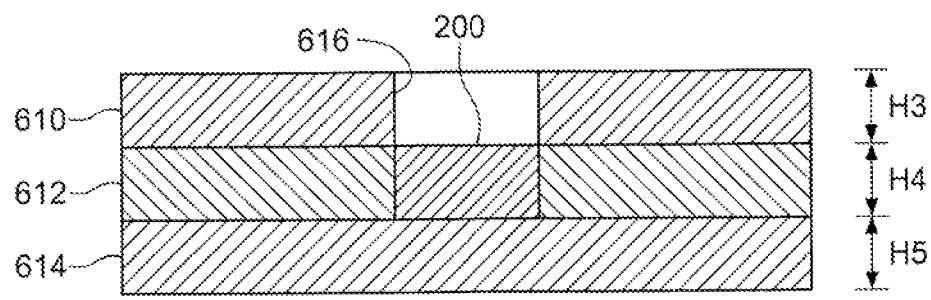
FIG. 14 illustrates one aspect an electronic device comprising materials and a base material for increased thickness.

FIG. 14 illustrates one aspect of an electronic device 200 comprising materials 610, 612 and a base material 614 for increased thickness. The base material 614 is attached to the base of the electronic device 200 by low pressure lamination. As shown, each layer of material 610, 612, 614 has a corresponding thickness H3, H4, H5. The dimensions of these thicknesses may vary from about 300 μm to about 3 mm. Optionally, a bore 616 may be defined in the area above the electronic device 200. Although in the illustrated example, three separate materials 610, 612, 614 are depicted, one or more materials may be employed. In one aspect, the skirt materials 610, 612, 614 are "non-electrically-conducting materials" and may be formed in various shapes and configurations. For example, the electronic device 200 may be surrounded entirely or partially by the materials 610, 612, 614 and may be positioned along a central axis of the electronic device 200 or off-center relative to a central axis. Thus, the shape of the materials 610, 612, 614 is not limited by the shape or size. Furthermore, in other aspects, the materials 610, 612, 614 may be separated by an additional material that is positioned in any defined region between the materials 610, 612, 614.

Figure 15:
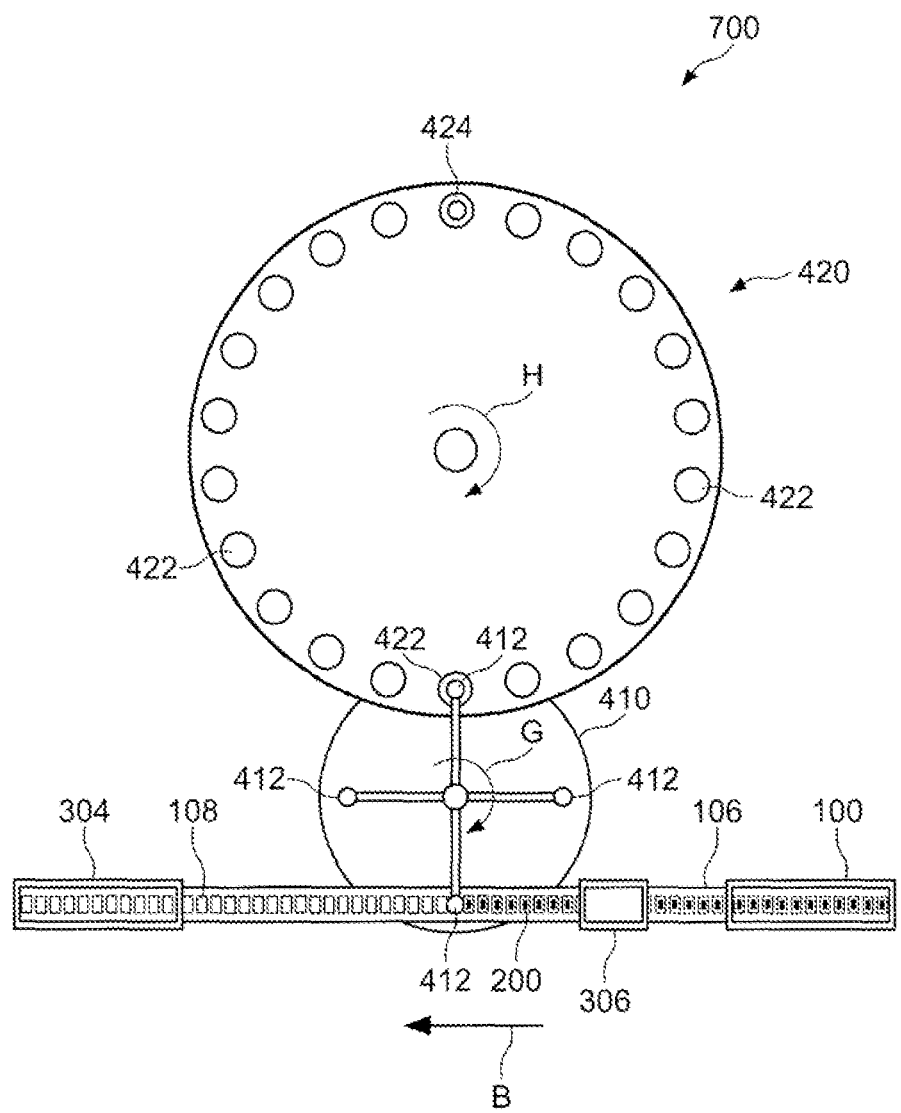
FIG. 15 illustrates one aspect of an assembling apparatus for compressing an electronic device with a powdered material into a tablet.

FIG. 15 illustrates one aspect of an assembling apparatus 700 for compressing an electronic device with a powdered material into a tablet. In one aspect, the assembling apparatus 700 comprises a tape and reel feed mechanism 300 operatively coupled to a rotary punch press 420. The tape and reel feed mechanism 300 interfaces directly with the rotary punch press 420 without using the conveyor system of FIG. 6. As shown, the tape and reel feed mechanism 300 comprises a rotary pick-and-place transfer mechanism 410 that rotates in direction G and includes multiple suction (vacuum) pick-and-place elements 412. The pick-and-place elements 412 pick electronic devices 200 from the carrier tape 106 and place them in a die cavity 422 of the rotary punch press 420, which has been pre filled with a powdered material. As the tape and reel feed mechanism 300 moves in direction B, the rotary punch press 420 rotates in direction H as shown. The rotary punch press 420 and the punch portion 424 operate in the same manner previously discussed in connection with FIGS. 6-12 to produce a tablet comprising the electronic device 200.

Figure 16:
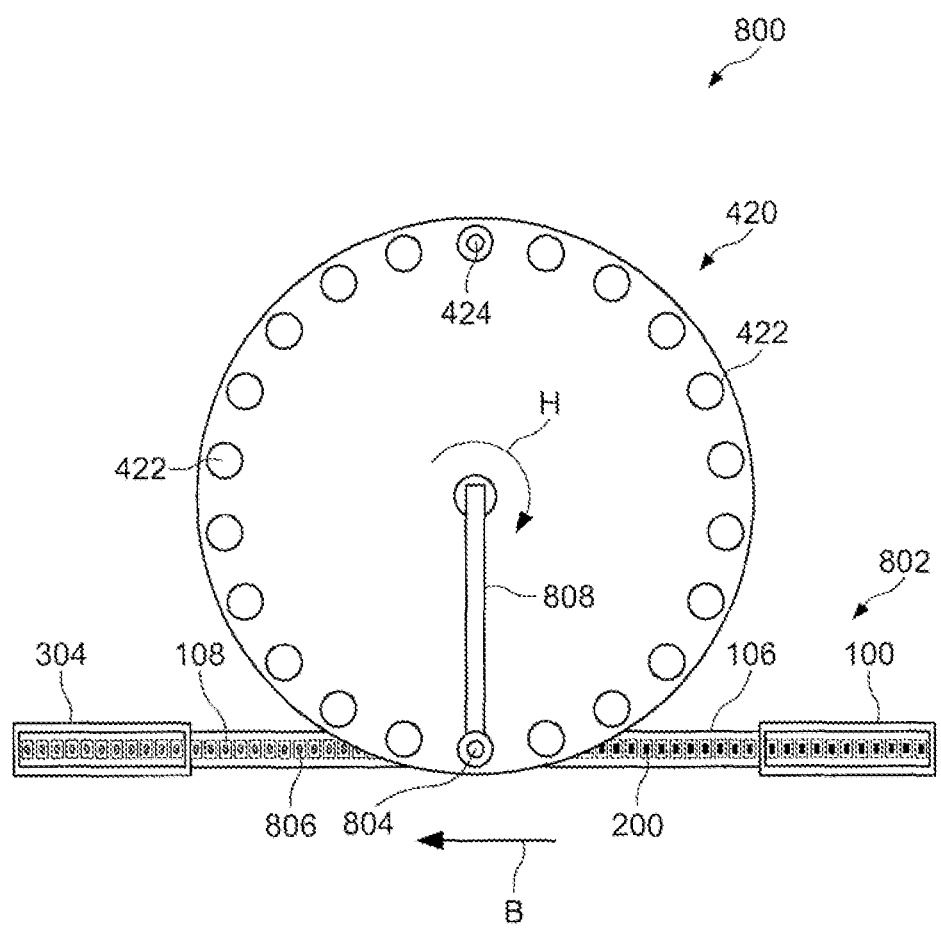
FIG. 16 illustrates one aspect of an assembling apparatus employing a punch station to dispense an electronic device and compress the electronic device with a powdered material into a tablet.

FIG. 16 illustrates one aspect of an assembling apparatus 800 employing a punch station 808 to dispense an electronic device 200 and compress the electronic device 200 with a powdered material into a tablet. In one aspect, the assembling apparatus 800 comprises a tape and reel feed mechanism 802 operatively coupled to a rotary punch press 420, previously discussed in connection with FIGS. 6-12. The tape and reel feed mechanism 802 does not include a rotary transfer mechanism using a rotary pick-and-place transfer mechanism as previously discussed herein. The tape and reel feed mechanism 802 feeds the carrier tape 106 in direction B without removing the cover tape from the carrier tape 106. Rather than using a rotary pick-and-place transfer mechanism to pick and place the electronic device 200 into the die cavity 422 of the rotary punch press 420, an ejector pin 804 (or punch) on the punch station 808 is used to punch the electronic device 200 through the carrier tape 106 package by perforating the carrier tape 106, leaving a perforation 806 or aperture, such that the electronic device 200 drops into the die cavity 422 positioned below the ejector pin 804. The ejector pin 804 is rotationally stationary and vertically movable by cam, solenoid, or other suitable actuation mechanism, without limitation. As the tape and reel feed mechanism 802 moves in direction B, the rotary punch press 420 rotates in direction H as shown. The rotary punch press 420 and the punch portion 424 operate in the same manner previously discussed in connection with FIGS. 6-12 to produce a tablet comprising the electronic device 200.

Figure 17:
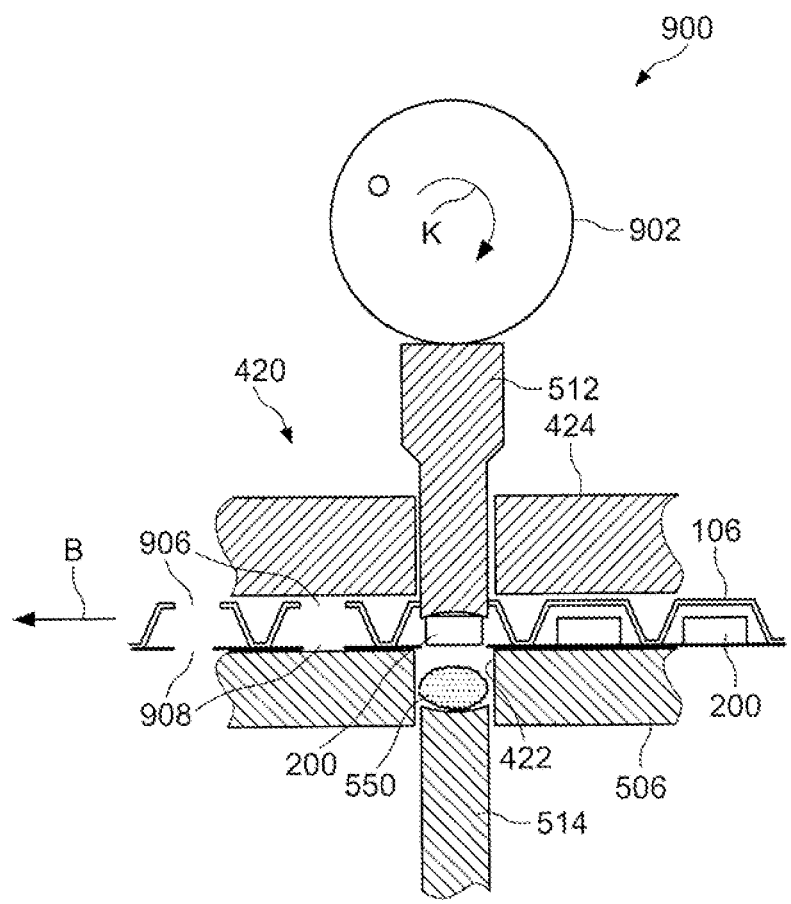
FIG. 17 illustrates one aspect of an assembling apparatus employing a punch press arrangement for dispensing an electronic device from a carrier tape and compressing the electronic device with a powdered material into a tablet.

FIG. 17 illustrates one aspect of an assembling apparatus 900 employing a punch press arrangement for dispensing an electronic device from a carrier tape and compressing the electronic device with a powdered material into a tablet. In one aspect, the assembling apparatus 900 comprises a tape and reel feed mechanism operatively coupled to a rotary punch press 420, previously discussed in connection with FIGS. 6-12. In the illustrated example, the carrier tape 106 is fed in direction B in between the die plate 506 and the punch portion 424 of the rotary punch press 420. The carrier tape 106 indexes in direction B such that the electronic device 200 is axially centered with the die cavity 422, which contains a powdered material 550, which has been tamped or pre-compressed, and the upper and lower punches 512, 514. A cam 902 actuates the upper punch 512—which acts as an ejector pin—to perforate the carrier tape 106, forming apertures 906, 908 above and below the carrier tape 106, to dispense the electronic device 200 into the die cavity 422 above the pre-compressed powdered material 550. As the cam 902 rotates further in direction K, the upper punch 512 compresses the powdered material 550 and the electronic device 200 into a tablet form. Thus, in a single operation, the electronic device 200 is dispensed and pressed into the tablet by actuating the upper punch 512 with the cam 902.

Figure 18:
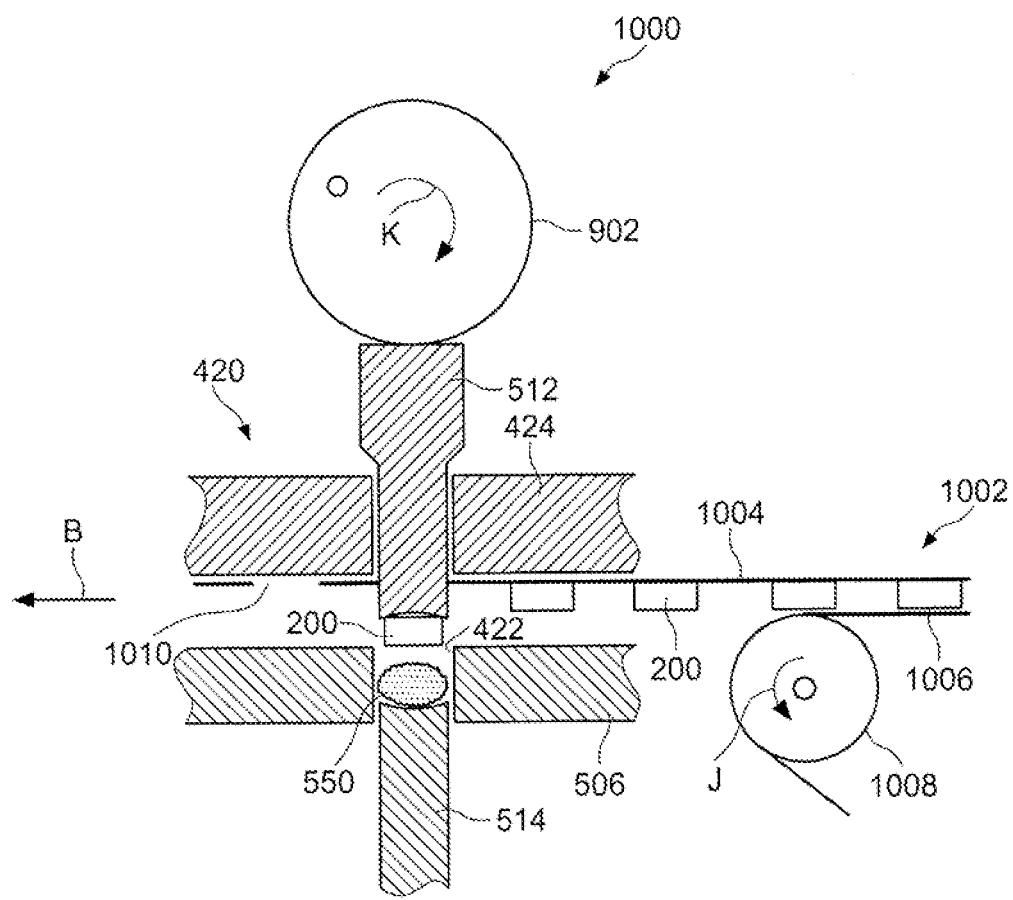
FIG. 18 illustrates one aspect of an assembling apparatus employing a punch press arrangement for dispensing an electronic device from a carrier tape comprising first and second adhesive tapes and compressing the electronic device with a powdered material into a tablet.

FIG. 18 illustrates one aspect of an assembling apparatus 1000 employing a punch press arrangement for dispensing an electronic device 200 from a carrier tape 1002 comprising first and second adhesive tapes 1004, 1006 and compressing the electronic device 200 with a powdered material into a tablet. In one aspect, the assembling apparatus 1000 comprises a tape and reel feed mechanism operatively coupled to a rotary punch press 420, previously discussed in connection with FIGS. 6-12. In the illustrated example, a carrier tape 1002 comprises a first adhesive tape 1004 and a second adhesive tape 1006 with the electronic device 200 located therebetween. The first and second adhesive tapes 1004, 1006 should have low mechanical strength but may be reinforced to facilitate reel handling. The first and second adhesive tapes 1004, 1006 may be laminated to the carrier tape 1002. As the carrier tape 1002 feds in direction B, a roller 1008 peels off the second adhesive tape 1006 to expose one side of the electronic device 200. The opposite side of the electronic device 200 remains attached to the first adhesive tape 1004. When the electronic device 200 is axially aligned with the die cavity 422 and the upper and lower punches 512, 514, the cam 902 actuates the upper punch 512 to perforate the first adhesive tape 1004 forming apertures 1010 in the first adhesive tape 1004 to eject the electronic device 200 into the die cavity 422 above the powdered material 550, which has been tamped or pre-compressed. As the cam 902 rotates further in direction K, the upper punch 512 compresses the powdered material 550 and the electronic device 200 into a tablet form. Thus, in a single operation, the electronic device 200 is dispensed and pressed into the tablet by actuating the upper punch 512 with the cam 902.

In one aspect, the upper punch 512 of the rotary punch press 420 used to cut through the carrier tape 1002, can have the same diameter as the electronic device 200, for example. Thus, after the electronic device 200 is ejected from the first adhesive tape 1004, the portion of the first adhesive tape 1004 located above the electronic device 200 remains attached to the electronic device 200. Accordingly, the first adhesive tape 1004 should be made of a biocompatible material and the thickness of the first adhesive tape 1004 should be selected to minimize the appearance on the tablet. The first adhesive tape 1004 may be made of a material that is fast dissolving in an aqueous solution. In another example, the adhesive tape 1004 need not necessarily be soluble in an aqueous solution. As such, the adhesive tape 1004 in contact with the electronic device 200 can be porous to allow aqueous solution ingress.

Figure 19:
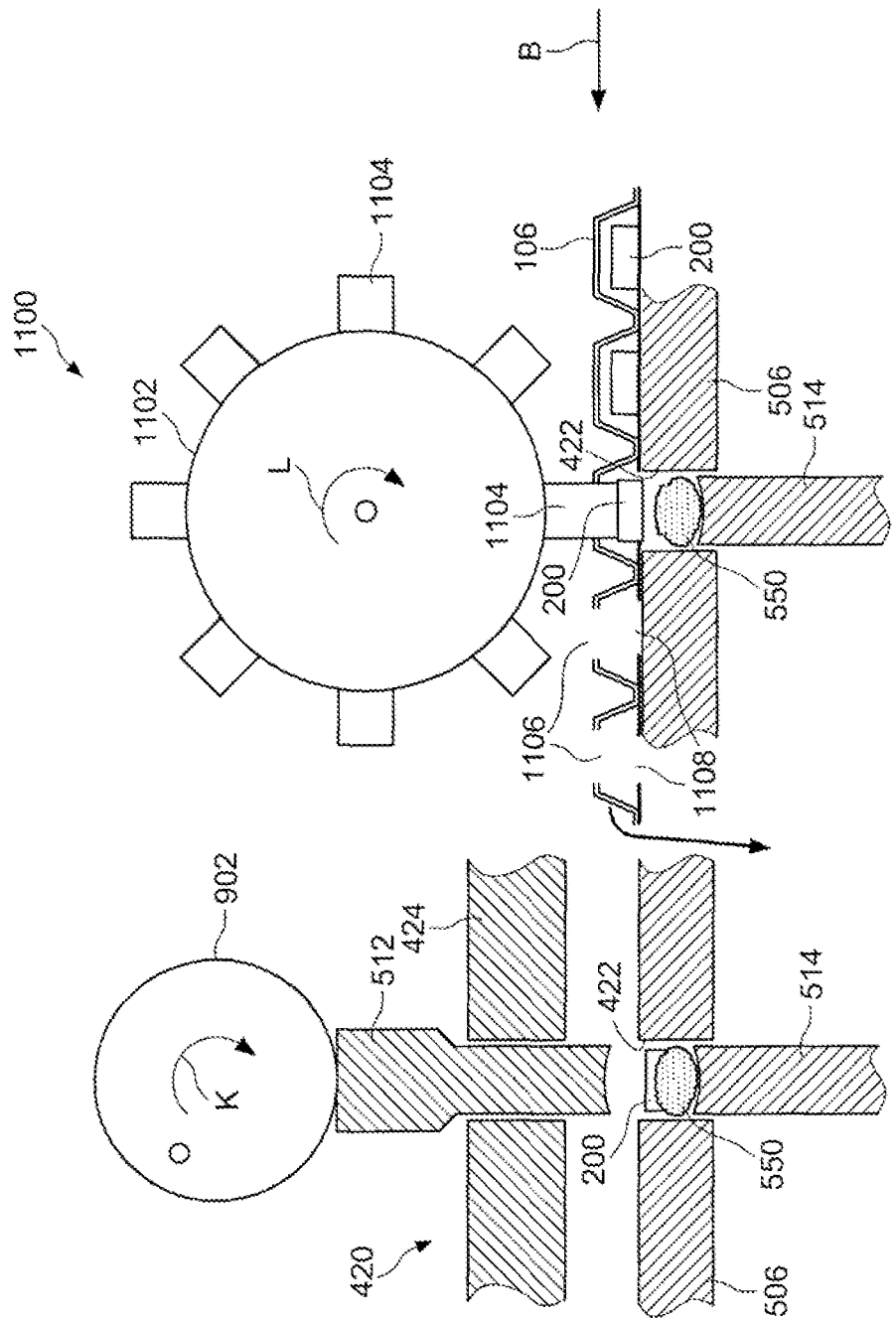
FIG. 19 illustrates one aspect of an assembling apparatus employing a rotating punch wheel comprising multiple punch heads for dispensing an electronic device from a carrier tape, and a separate punch press process for compressing the electronic device with a powdered material into a tablet.

FIG. 19 illustrates one aspect of an assembling apparatus 1100 employing a rotating punch wheel 1102 comprising multiple punch heads 1104 for dispensing an electronic device 200 from a carrier tape 106, and a separate punch press process for compressing the electronic device 200 with a powdered material into a tablet. In one aspect, the assembling apparatus 1100 comprises a tape and reel feed mechanism operatively coupled to a rotary punch press 420, previously discussed in connection with FIGS. 6-12. In the illustrated example, the assembling apparatus 1100 comprises a rotating punch wheel 1102 comprising multiple punch heads 1104. As the carrier tape 106 is fed in direction B, the punch wheel 1102 rotates in direction L such that the punch head 1104 perforates the carrier tape 106, forming apertures 1106, 1108 above and below the carrier tape 106, to dispense the electronic device 200 into the die cavity 422 above the powdered material 550, which has been tamped or pre-compressed. Once the electronic device 200 is positioned within the die cavity 422, the process continues to the punch portion 424 of the rotary punch press 420 to press the electronic device 200 into a tablet using the upper and lower pressing punches 512, 514.

Figure 20:
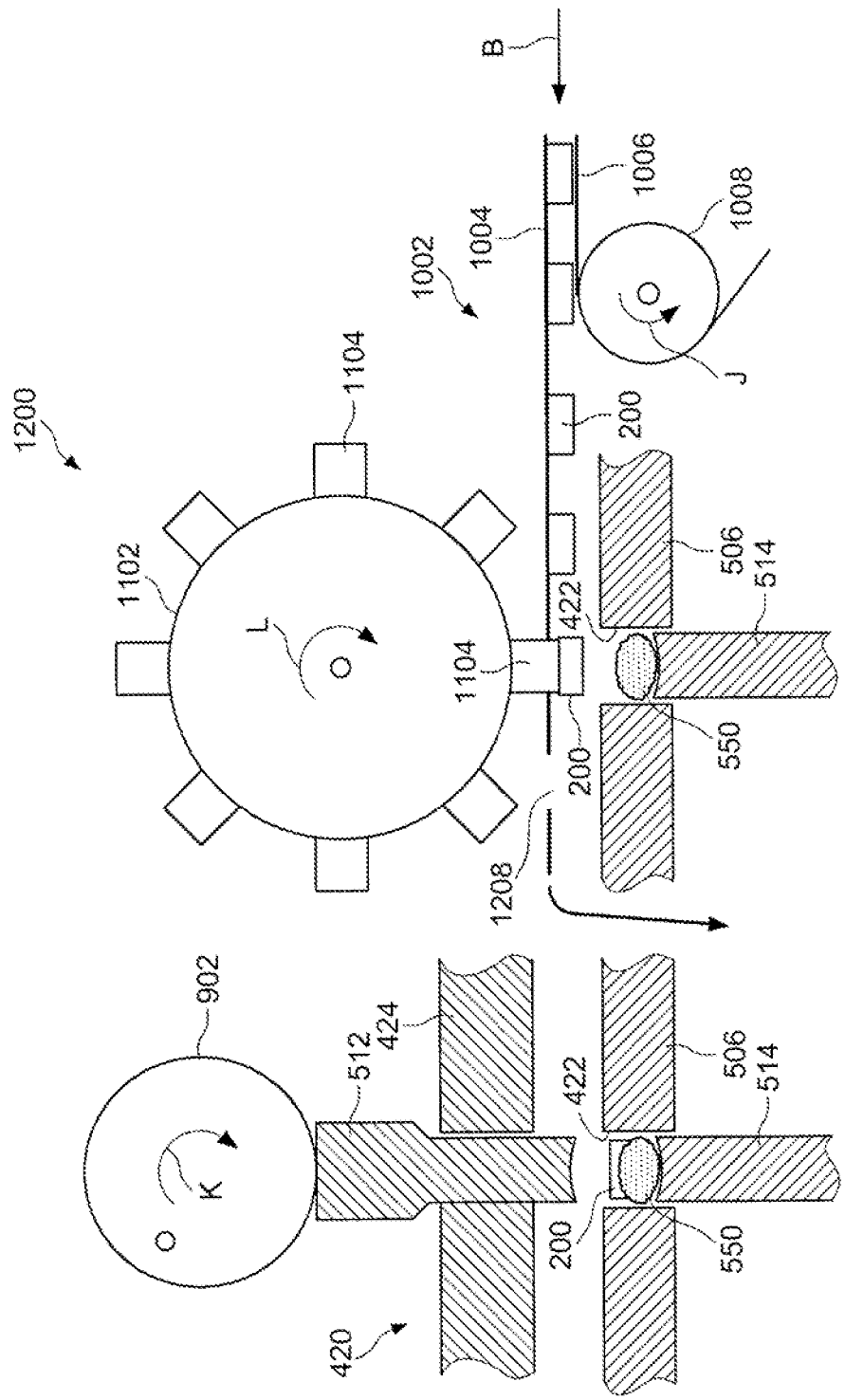
FIG. 20 illustrates one aspect of an assembling apparatus employing a rotating punch wheel comprising multiple punch heads for dispensing an electronic device from a carrier tape comprising first and second adhesive tapes sandwiching an electronic device therebetween, and a separate punch press process for compressing the electronic device with a powdered material into a tablet.

FIG. 20 illustrates one aspect of an assembling apparatus 1200 employing a rotating punch wheel 1102 comprising multiple punch heads 1104 for dispensing an electronic device 200 from a carrier tape 1002 comprising first and second adhesive tapes 1004, 1006 sandwiching an electronic device 200 therebetween, and a separate punch press process for compressing the electronic device 200 with a powdered material into a tablet. In one aspect, the assembling apparatus 1200 comprises a tape and reel feed mechanism operatively coupled to a rotary punch press 420, previously discussed in connection with FIGS. 6-12. In the illustrated example, the assembling apparatus 1200 comprises a rotating punch wheel 1102 comprising multiple punch heads 1104. The carrier 1002 comprises a first adhesive tape 1004 and a second adhesive tape 1006 with the electronic device 200 located therebetween, where the first and second adhesive tapes 1004, 1006 have low mechanical strength but may be reinforced to facilitate reel handling, as discussed in connection with FIG. 18. As the carrier tape 1002 is fed in direction B, the second adhesive tape 1006 is peeled from the electronic device 200 and is rolled up by a roller 1008. The punch wheel 1102 rotates in direction L such that the punch head 1104 perforates the first adhesive tape 1004, forming apertures 1206 in the first adhesive tape 1104, to dispense the electronic device 200 into the die cavity 422 above the powdered material 550, which has been tamped or pre-compressed. Once the electronic device 200 is positioned within the die cavity 422, the process continues to the punch portion 424 of the rotary punch press 420 to press the electronic device 200 into a tablet using the upper and lower pressing punches 512, 514.

Figure 21:
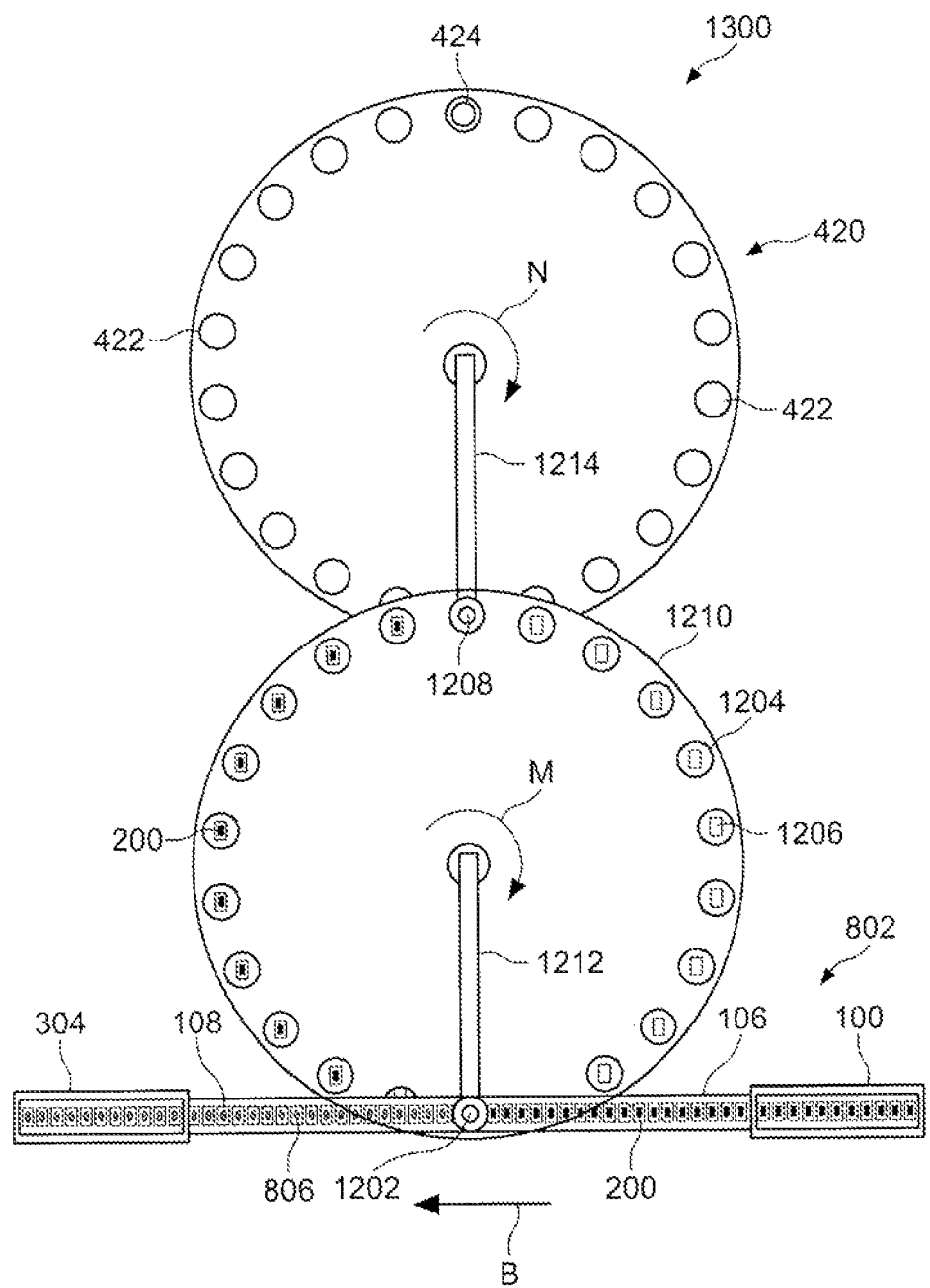
FIG. 21 illustrates one aspect of an assembling apparatus employing a rotary carrier wheel comprising a first punch station and rotary punch press comprising a second punch station to dispense an electronic device and compress the electronic device with a powdered material into a tablet.

FIG. 21 illustrates one aspect of an assembling apparatus 1200 employing a rotary carrier wheel 1210 comprising a first punch station 1212 and rotary punch press 420 comprising a second punch station 1214 to dispense an electronic device 200 and compress the electronic device 200 with a powdered material into a tablet. In one aspect, the assembling apparatus 1200 comprises a tape and reel feed mechanism 802 operatively coupled to a rotary punch press 420, previously discussed in connection with FIGS. 6-12. The tape and reel feed mechanism 802 does not include a rotary transfer mechanism using a rotary pick-and-place transfer mechanism as previously discussed herein. The tape and reel feed mechanism 802 feeds the carrier tape 106 in direction B without removing the cover tape from the carrier tape 106.

In the illustrated example, the carrier tape 106 is positioned below a first punch station 1212 comprising an ejector pin 1202 as the rotary carrier wheel 1210 rotates in direction M. The rotary carrier wheel 1210 can ride on a top surface of the rotary punch press 420 table for placement control. As the rotary carrier wheel 1210 rotates in direction M, the ejector pin 1202 of the first punch station 1212 punches the electronic device 200 through the carrier tape 106 package by perforating the carrier tape 106, leaving a perforation 806 or aperture, such that the electronic device 200 drops into a carrier assembly 1204 positioned below the ejector pin 804. The ejector pin 804 is rotationally stationary and vertically movable by cam, solenoid, or other suitable actuation mechanism, without limitation. The carrier assembly 1204 comprises an aperture 1206 to frictionally hold the electronic device 200 in place until the next transfer process step. The transfer wheel 1210 rotates in direction M to the second punch station 1214 at the rotary punch press 420, which rotates in direction N, where a second ejector pin 1208 punches the electronic device 200 into the die cavity 422 of the rotary punch press 420, which has been pre filled with a powdered material 550, which has been tamped or pre-compressed. In one aspect, the second ejector pin 1208 can provide pre-compression or tamping of the powdered material 550. The rotary punch press 420 and the punch portion 424 operate in the same manner previously discussed in connection with FIGS. 6-12 to produce a tablet comprising the electronic device 200.

In various aspects, the carrier assembly 1204 may be configured to center the electronic component 200 to properly align the electronic device with the die cavity 422. Thus, the carrier assembly 1204 may be configured to align the electronic device 200 with the center of the die cavity 422. This process may be assisted by vision guidance systems, pick-and-place tip designs, or other suitable mechanical configurations. Additional features include features formed on the electronic device 200 to enable suitable placement of the electronic device 200 relative to the die cavity 422.

In other aspects, rather than employing the first or second punch stations 1212, 1214 comprising ejector pins 1202, 1208 at the rotary carrier wheel 1210 or the rotary punch press 420 wheel, the electronic device 200 can be handled with a vacuum pick-and-place machine can be employed to pick-up pre-punched electronic devices 200 from a waffle pack, tube, vibratory bowl, sheet, web strip, IDEC tray, carrier tape with adhered electronic device, among others.

Figure 22:
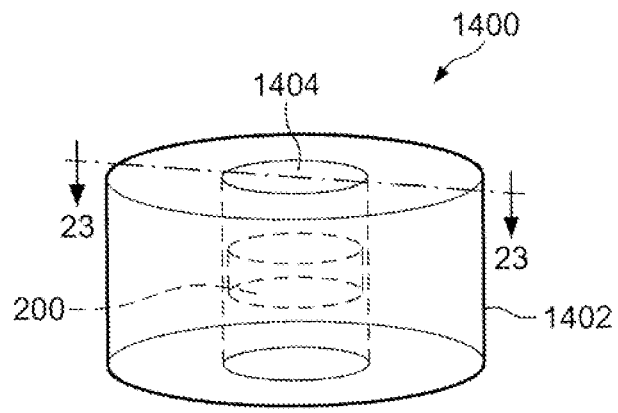
FIG. 22 illustrates one aspect of a carrier comprising an electronic device embedded in a weighted annulus.
Figure 23:
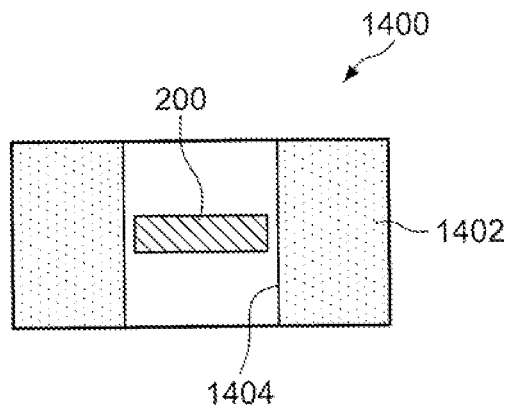
FIG. 23 is a cross-sectional view taken along line 23-23 of the carrier shown in FIG. 22.

FIG. 22 illustrates one aspect of a carrier 1400 comprising an electronic device 200 embedded in a weighted annulus 1402, and FIG. 23 is a cross-sectional view taken along line 23-23. With reference now to FIGS. 22 and 23, in one aspect, the weight and shape of the carrier 1400 is compatible with core tablet press handlers that interface with the rotary punch press 420, as previously described. The carrier 1400 defines a cavity 1404 for receiving the electronic device 200 therein.

Figure 24:
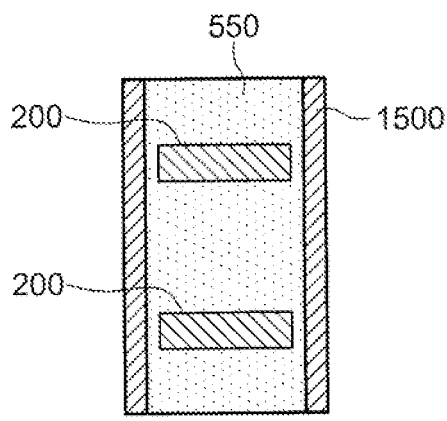
FIG. 24 illustrates one aspect of a tube filled with a powdered material and at least two electronic devices.

FIG. 24 illustrates one aspect of a tube 1500 filled with a powdered material 550 and at least two electronic devices 200. The tube 1500 is loaded with powdered material 550 and is then tamped or pre-compressed. The tube 1500 is loaded with alternating layers of a pre-metered quantity of powdered material 550 and electronic devices 200. A press punch compresses the powdered material 550 and the electronic devices 200 into tablet forms.

Any of the processes described hereinabove for manufacturing a tablet comprising an electronic device may be controlled using a variety of process controls. Such process controls include, without limitation, monitoring for various process variables or parameters to ensure that a suitable amount of powdered material was or is dispensed into the die cavity and to also to determine that a single electronic device, or suitable number of electronic devices, is dispensed in the die cavity per tablet. Such process variables or parameters that can be monitored by a process control system include, without limitation, weight of the dispended powdered material, weight of the electronic device, metal detection to detect the electronic device, wireless interrogation of the electronic device, tamp/compression force compression measurements, vision, X-rays, light/backlight/dark contrast, vertical placement, electrical, among others. In addition, any of the electronic device, powder filling, or tablet ejection operations described hereinabove, may be vision controlled, or controlled by other suitable process control means described herein.

Any of the operations described hereinabove for transferring the electronic device, powdered material, or tablet may be performed using transfer wheels, conveyors, pick-and-place machines, hopper feed, gravity feed, mechanical feed, punch press, slide ramp, rotary wheel, vibratory bowl, among other suitable transfer mechanisms. In addition, any of such component transfer operations may be performed by a SCARA Cartesian robotic device, where SCARA is an acronym that stands for Selective Compliant Assembly Robot. It also may be referred to as a Selective Compliant Articulated Robot Arm. In general, a SCARA robot is a 4-axis robot arm that can move to any X-Y-Z coordinate within a predefined work envelope. A fourth axis of motion may include wrist rotation (Theta-Z). The vertical motion is usually an independent linear axis at the wrist or in the base. The SCARA robot arm includes a parallel-axis joint layout with an arm that is slightly compliant in the X-Y direction but rigid in the "Z" direction making it selective compliant. A SCARA robot may be configured to operate under controlling software that requires inverse kinematics for linear interpolated moves.

As previously discussed, accessing and handling of the electronic device 200 may be performed using a variety of techniques including, without limitation, pick and place components, actuators, punch portion, peeled off tape, conveyor, gravity feed, air pressure, laser cuts, die ejection, among other techniques. Pick and place components include, without limitation, vacuum tools, adhesion, gripper. Once dispensed, the electronic devices 200 can be provided to a subsequent process, such as a rotary tablet press process, by a transfer wheel, conveyor, pick and place components, actuators, hopper, gravity feed, vibratory feed, punched into rotary tablet press, slide/ramp, or air pressure.

It will be appreciated that any of the tape-and-reel feed mechanisms described hereinabove may be configured to operate with a singles reel or with multiple reels. In other aspects, the reel may be replaced with a web or sheet comprising one or more rows and columns of components, e.g., electronic devices, for dispensing and transferring into the die cavity for compression with a powdered material into a tablet.

Figure 25A:
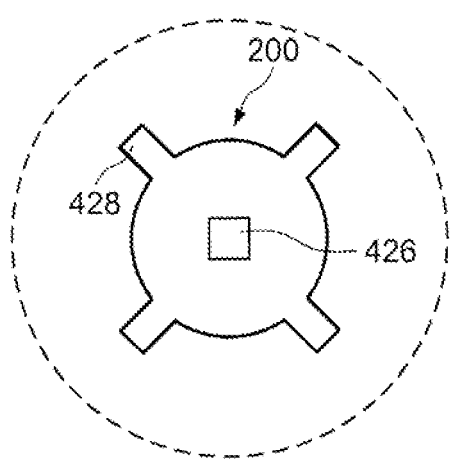
FIG. 25A illustrates one aspect of an electronic device that includes tabs or legs and electronics.

Referring now to FIG. 25A, in accordance with one aspect, the electronic device 200 includes tabs or legs 428 and electronics 426. The legs 428 are flexible and as the electronic device 200 is pushed into the die cavity 422, the friction between the legs 428 and the wall of the die cavity 422 hold the electronic device 200 in place.

Figure 25B:
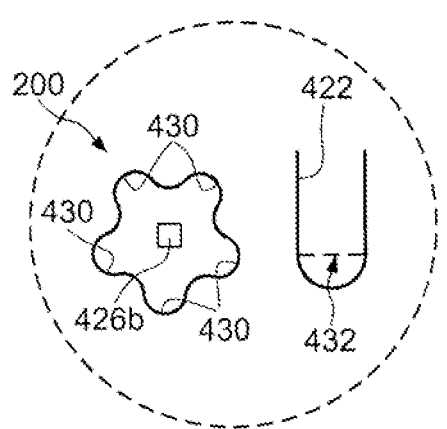
FIG. 25B illustrates one aspect of an electronic device that includes tabs or legs and electronics.

Turning now to FIG. 25B, in accordance with one aspect, the electronic device 200 includes tabs or legs 430 and electronics 426. The legs 430 are used to secure the electronic device 200 into the carrier 404. The carrier 404 includes a matching number of slots or indentations 432 to the legs 430 of the electronic device 200. In an alternative aspect, the number of legs 430 may differ from the number of slots 432. As the electronic device 200 is pressed inside the carrier 404, the tabs 430 engage the slots 432 and lock the electronic device 200 into place mechanically. In use, as the carrier 404 dissolves, the walls of the carrier 404 change shape or collapse causing the electronic device 200 to be released from the carrier 404. In addition, a film layer may be manufactured via lamination, application of a coating solution, or slurry followed by a cure. In accordance with other aspects, the film or layer may be formed using dry compression, such as tablet press.

Figure 26:
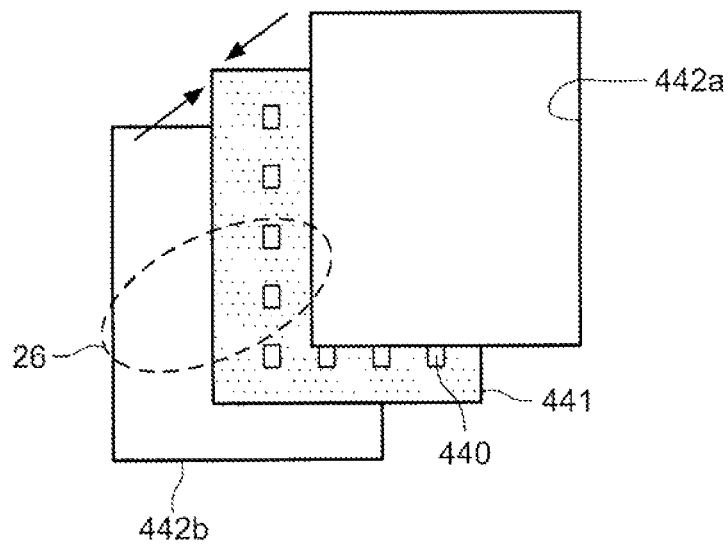
FIG. 26 illustrates one aspect of an electronic device shown on a sheet, where the electronic device includes a skirt with a plurality of holes and electronics.
Figure 27:
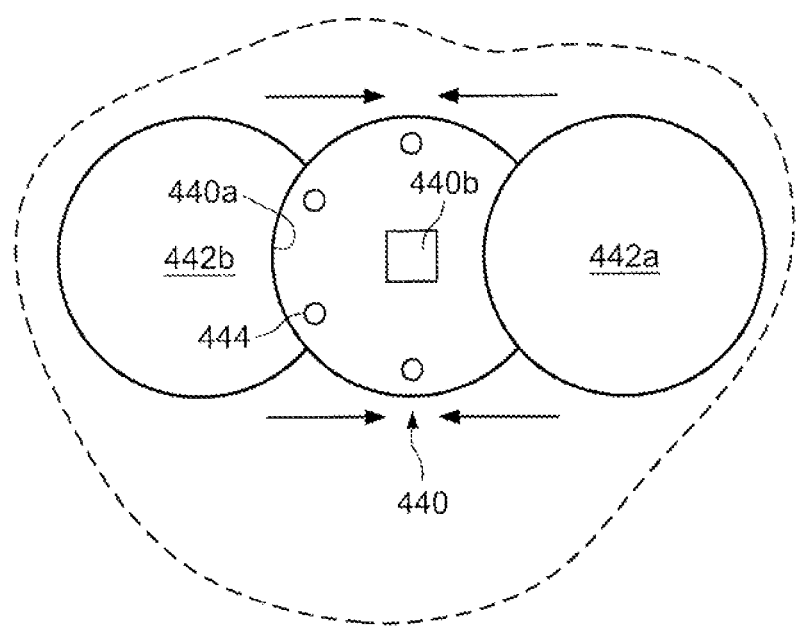
FIG. 27 illustrates one aspect of an electronic device laminated between two sheets.

As shown in FIG. 26, the electronic device 200 shown on a sheet 441, where the electronic device 200 includes a skirt with a plurality of holes 444 and electronics 440. As the sheets 442a and 442b are subject to heating or pressure, then the sheets 442a and 442b are secured to each other through the holes 444 and the electronic device 200 is securely held between the sheets 442a and 442b. As shown in FIG. 27, the electronic device 200 is laminated between the sheets 442a and 442b. Thus, as the portions of the sheets 442a and 442b are exposed to heat or pressure, then the oversized portions at the edges are secured to each other forming a pocket that surrounds the electronic device 200 as well as secured to in place through the holes 444 as noted above. In accordance with another aspect, the holes 444 may be eliminated when the device is placed between the oversized portions and secured within a pocket that surrounds the electronic device 200.

Figure 28:
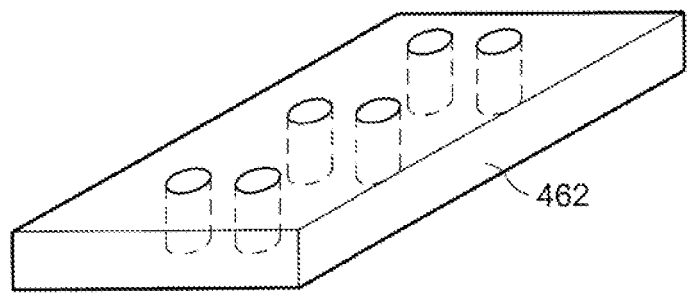
FIGS. 28-32 illustrate one aspect of an electronic device punched out and placed inside a hole of a transfer tray.
Figure 29:
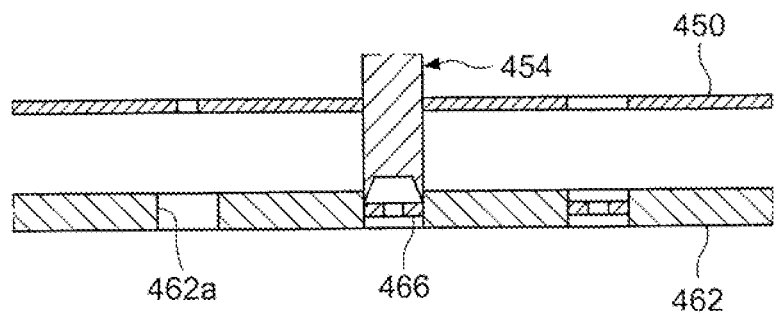
Figure 30:
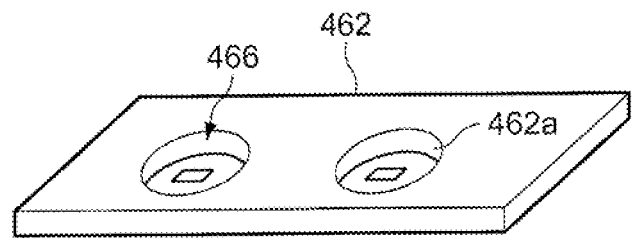
Figure 31:
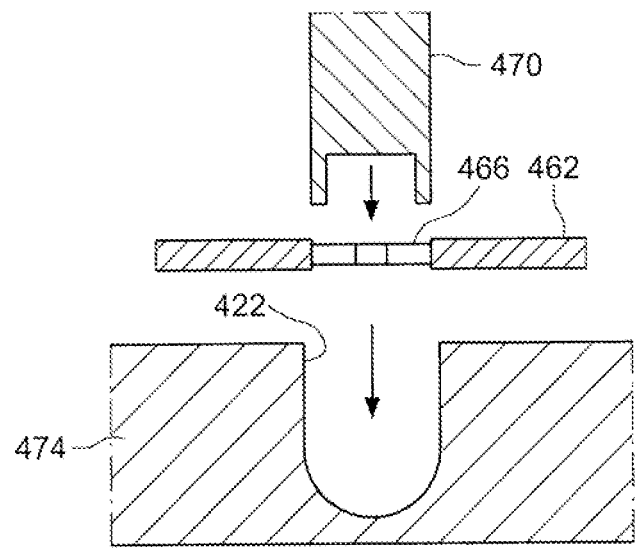
Figure 32:
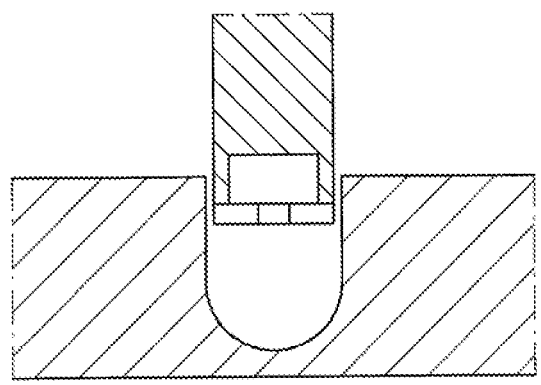

Referring now to FIGS. 28-32, in accordance with one aspect, the electronic device 200 may be punched out and placed inside a hole 462a of a transfer tray 462. The tray 462 is shown in FIG. 28 with a plurality of holes. As shown in FIG. 29, the tray 462 is positioned below a sheet of electronic devices 200. A punch blade 454 cuts an electronic device 200 from the sheet of devices and inserts the electronic device 200 into the hole 462a. The electronic device 200 is held in place in the hole 462 with friction as shown in FIG. 30. The tray 462 is then advanced to the next step of the process and a punch press 470 pushes the electronic device 200 into a die cavity 422 as shown in FIGS. 31 and 32.

Figure 33:
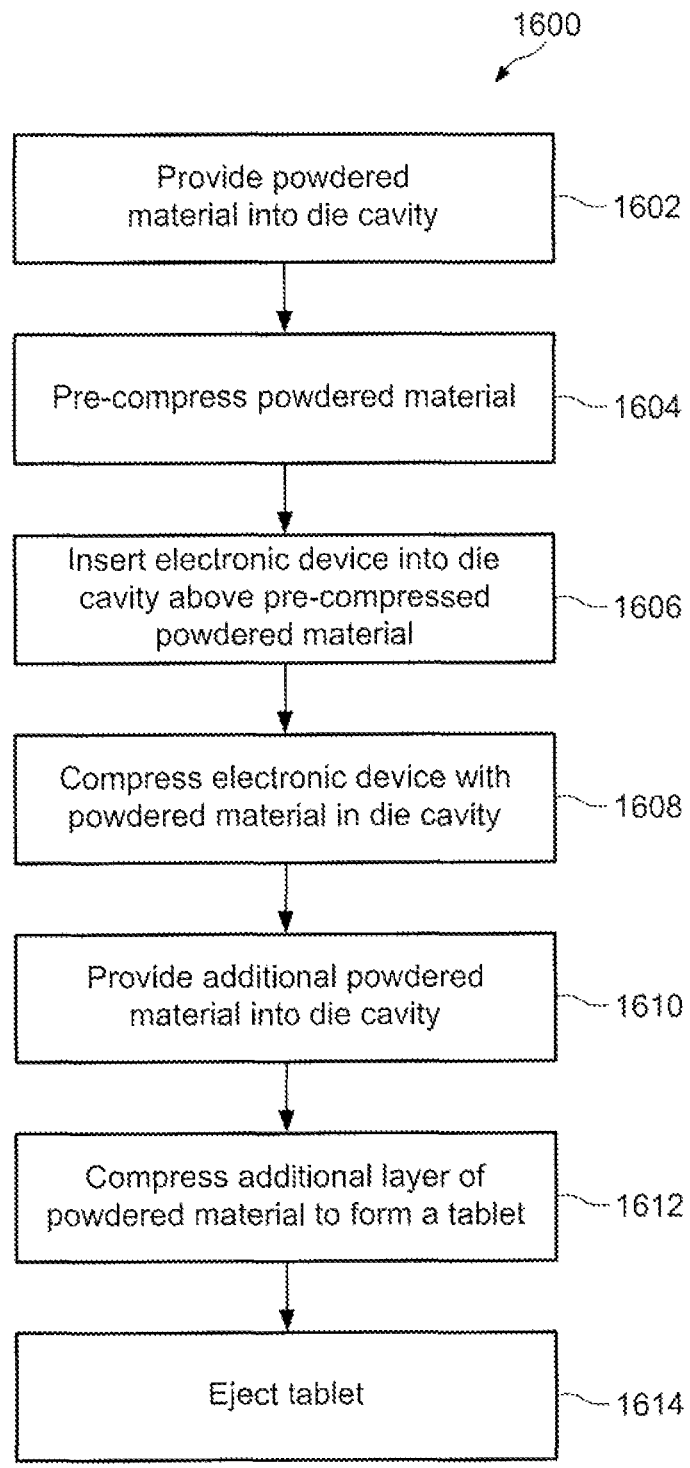
FIG. 33 illustrates one aspect of a logic flow diagram for a process of producing a tablet by compressing an electronic device with a powdered material.

Having described various manufacturing systems for producing a tablet by compressing an electronic device with a powdered material, the present disclosure now turns to a description of a general process for producing a tablet by compressing an electronic device with a powdered material. Accordingly, FIG. 33 illustrates one aspect of a logic flow diagram 1600 for a process of producing a tablet by compressing an electronic device with a powdered material. At 1602, a powdered material is provided into a die cavity. At 1604, the powdered material in the die cavity tamped or pre-compressed. At 1606, an electronic device, preferably in the form of a semiconductor die, is inserted into the die cavity above the pre-compressed powdered material. At 1608, the electronic device is compressed with the pre-compressed powdered material. At 1610, an additional, over layer, of powdered material is provided into the die cavity to form a tablet. At 1612, the over layer of powdered material is compressed. At 1614, the pressed electronic device and powdered material in the form of a tablet is ejected from the die cavity.

In one aspect, a machine vision inspection of the die cavity may be performed after any one of the steps 1602-1614. The vision inspection can be useful to determine whether the powdered material and/or the die have been properly placed in the die cavity prior to tamping or compressing them into the final tablet product. In other aspects, in addition to machine vision, other forms of inspection may be employed, such as, for example, without limitation, weight of the dispended powdered material, weight of the electronic device, metal detection to detect the electronic device, wireless interrogation of the electronic device, tamp/compression force compression measurements, X-rays, light/backlight/dark contrast, vertical placement, electrical, among others.

In one aspect, the electronic device 200 is an ingestible event marker (IEM) as illustrated and described in connection with FIG. 34. With reference to FIG. 34, there is shown one aspect of an ingestible device event indicator system with dissimilar metals positioned on opposite ends as system 2030. The system 2030 can be used in association with any pharmaceutical product, as mentioned above, to determine when a patient takes the pharmaceutical product. As indicated above, the scope of the present disclosure is not limited by the environment and the product that is used with the system 2030. For example, the system 2030 may be compressed into a tablet or placed within a capsule and the tablet or capsule is placed within the conducting liquid. The tablet or capsule would then dissolve over a period of time and release the system 2030 into the conducting liquid. Thus, in one aspect, the tablet or capsule would contain the system 2030 and no product. Such a tablet or capsule may then be used in any environment where a conducting liquid is present and with any product. For example, the tablet or capsule may be dropped into a container filled with jet fuel, salt water, tomato sauce, motor oil, or any similar product. Additionally, the tablet or capsule containing the system 2030 may be ingested at the same time that any pharmaceutical product is ingested in order to record the occurrence of the event, such as when the product was taken.

In the specific example of the system 2030 combined with the pharmaceutical product, as the product or pill, tablet, or capsule is ingested, the system 2030 is activated. The system 2030 controls conductance to produce a unique current signature that is detected, thereby signifying that the pharmaceutical product has been taken. The system 2030 includes a framework 2032. The framework 2032 is a chassis for the system 2030 and multiple components are attached to, deposited upon, or secured to the framework 2032. In this aspect of the system 2030, a digestible material 2034 is physically associated with the framework 2032. The material 2034 may be chemically deposited on, evaporated onto, secured to, or built-up on the framework all of which may be referred to herein as "deposit" with respect to the framework 2032. The material 2034 is deposited on one side of the framework 2032. The materials of interest that can be used as material 2034 include, but are not limited to: Cu or CuI. The material 2034 is deposited by physical vapor deposition, electrodeposition, or plasma deposition, among other protocols. The material 2034 may be from about 0.05 to about 500 μm thick, such as from about 5 to about 100 μm thick. The shape is controlled by shadow mask deposition, or photolithography and etching. Additionally, even though only one region is shown for depositing the material, each system 2030 may contain two or more electrically unique regions where the material 2034 may be deposited, as desired.

At a different side, which is the opposite side as shown in FIG. 34, another digestible material 2036 is deposited, such that materials 2034 and 2036 are dissimilar. Although not shown, the different side selected may be the side next to the side selected for the material 2034. The scope of the present disclosure is not limited by the side selected and the term "different side" can mean any of the multiple sides that are different from the first selected side. Furthermore, even though the shape of the system is shown as a square, the shape maybe any geometrically suitable shape. Material 2034 and 2036 are selected such that they produce a voltage potential difference when the system 2030 is in contact with conducting liquid, such as body fluids. The materials of interest for material 2036 include, but are not limited to: Mg, Zn, or other electronegative metals. As indicated above with respect to the material 2034, the material 2036 may be chemically deposited on, evaporated onto, secured to, or built-up on the framework. Also, an adhesion layer may be necessary to help the material 2036 (as well as material 2034 when needed) to adhere to the framework 2032. Typical adhesion layers for the material 2036 are Ti, TiW, Cr or similar material. Anode material and the adhesion layer may be deposited by physical vapor deposition, electrodeposition or plasma deposition. The material 2036 may be from about 0.05 to about 500 μm thick, such as from about 5 to about 100 μm thick. However, the scope of the present disclosure is not limited by the thickness of any of the materials nor by the type of process used to deposit or secure the materials to the framework 2032.

Thus, when the system 2030 is in contact with the conducting liquid, a current path, an example is shown in FIG. 36, is formed through the conducting liquid between material 2034 and 2036. A control device 2038 is secured to the framework 2032 and electrically coupled to the materials 2034 and 2036. The control device 2038 includes electronic circuitry, for example control logic that is capable of controlling and altering the conductance between the materials 2034 and 2036.

The voltage potential created between the materials 2034 and 2036 provides the power for operating the system as well as produces the current flow through the conducting fluid and the system. In one aspect, the system operates in direct current mode. In an alternative aspect, the system controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the materials 2034 and 2036 is completed external to the system 2030; the current path through the system 2030 is controlled by the control device 2038. Completion of the current path allows for the current to flow and in turn a receiver, not shown, can detect the presence of the current and recognize that the system 2030 has been activate and the desired event is occurring or has occurred.

In one aspect, the two materials 2034 and 2036 are similar in function to the two electrodes needed for a direct current power source, such as a battery. The conducting liquid acts as the electrolyte needed to complete the power source. The completed power source described is defined by the physical chemical reaction between the materials 2034 and 2036 of the system 2030 and the surrounding fluids of the body. The completed power source may be viewed as a power source that exploits reverse electrolysis in an ionic or a conductive solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, these two materials are shielded from the surrounding environment by an additional layer of material. Accordingly, when the shield is dissolved and the two dissimilar materials are exposed to the target site, a voltage potential is generated.

Referring again to FIG. 34, the materials 2034 and 2036 provide the voltage potential to activate the control device 2038. Once the control device 2038 is activated or powered up, the control device 2038 can alter conductance between the materials 2034 and 2036 in a unique manner. By altering the conductance between materials 2034 and 2036, the control device 2038 is capable of controlling the magnitude of the current through the conducting liquid that surrounds the system 2030. This produces a unique current signature that can be detected and measured by a receiver (not shown), which can be positioned internal or external to the body. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, the entire content of which is incorporated herein by reference. Alternatively, throughout the disclosure herein, the terms "non-conducting material", "membrane", and "skirt" are interchangeably with the term "current path extender" without impacting the scope or the present aspects and the claims herein. The skirt, shown in portion at 2035 and 2037, respectively, may be associated with, e.g., secured to, the framework 2032. Various shapes and configurations for the skirt are contemplated as within the scope of the present disclosure. For example, the system 2030 may be surrounded entirely or partially by the skirt and the skirt maybe positioned along a central axis of the system 2030 or off-center relative to a central axis. Thus, the scope of the present disclosure is not limited by the shape or size of the skirt. Furthermore, in other aspects, the materials 2034 and 2036 may be separated by one skirt that is positioned in any defined region between the materials 2034 and 2036.

Referring now to FIG. 35, in another aspect of an ingestible device is shown in more detail as system 2040. The system 2040 includes a framework 2042. The framework 2042 is similar to the framework 2032 of FIG. 34. In this aspect of the system 2040, a digestible or dissolvable material 2044 is deposited on a portion of one side of the framework 2042. At a different portion of the same side of the framework 2042, another digestible material 2046 is deposited, such that materials 2044 and 2046 are dissimilar. More specifically, material 2044 and 2046 are selected such that they form a voltage potential difference when in contact with a conducting liquid, such as body fluids. Thus, when the system 2040 is in contact with and/or partially in contact with the conducting liquid, then a current path, an example is shown in FIG. 36, is formed through the conducting liquid between material 2044 and 2046. A control device 2048 is secured to the framework 2042 and electrically coupled to the materials 2044 and 2046. The control device 2048 includes electronic circuitry that is capable of controlling part of the conductance path between the materials 2044 and 2046. The materials 2044 and 2046 are separated by a non-conducting skirt 2049. Various examples of the skirt 2049 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and published as 2009-0082645, entitled "IN-BODY DEVICE WITH VIRTUAL DIPOLE SIGNAL AMPLIFICATION"; the entire disclosure of each is incorporated herein by reference.

Once the control device 2048 is activated or powered up, the control device 2048 can alter conductance between the materials 2044 and 2046. Thus, the control device 2048 is capable of controlling the magnitude of the current through the conducting liquid that surrounds the system 2040. As indicated above with respect to system 2030, a unique current signature that is associated with the system 2040 can be detected by a receiver (not shown) to mark the activation of the system 2040. In order to increase the "length" of the current path the size of the skirt 2049 is altered. The longer the current path, the easier it may be for the receiver to detect the current.

Referring now to FIG. 36, the system 2030 of FIG. 34 is shown in an activated state and in contact with conducting liquid. The system 2030 is grounded through ground contact 2052. The system 2030 also includes a sensor module 2074, which is described in greater detail with respect to FIG. 39 ion or current paths 2050 form between material 2034 to material 2036 through the conducting fluid in contact with the system 2030. The voltage potential created between the material 2034 and 2036 is created through chemical reactions between materials 2034/2036 and the conducting fluid.

FIG. 37 shows an exploded view of the surface of the material 2034. The surface of the material 2034 is not planar, but rather an irregular surface 2054 as shown. The irregular surface 2054 increases the surface area of the material and, hence, the area that comes in contact with the conducting fluid.

In one aspect, at the surface of the material 2034, there is chemical reaction between the material 2034 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl⁻ in solution. The flow of ions into the conduction fluid is depicted by the ion paths 2050. In a similar manner, there is a chemical reaction between the material 2036 and the surrounding conducting fluid and ions are captured by the material 2036. The release of ions at the material 2034 and capture of ion by the material 2036 is collectively referred to as the ionic exchange. The rate of ionic exchange and, hence the ionic emission rate or flow, is controlled by the control device 2038. The control device 2038 can increase or decrease the rate of ion flow by altering the conductance, which alters the impedance, between the materials 2034 and 2036. Through controlling the ion exchange, the system 2030 can encode information in the ionic exchange process. Thus, the system 2030 uses ionic emission to encode information in the ionic exchange.

The control device 2038 can vary the duration of a fixed ionic exchange rate or current flow magnitude while keeping the rate or magnitude near constant, similar to when the frequency is modulated and the amplitude is constant. Also, the control device 2038 can vary the level of the ionic exchange rate or the magnitude of the current flow while keeping the duration near constant. Thus, using various combinations of changes in duration and altering the rate or magnitude, the control device 2038 encodes information in the current flow or the ionic exchange. For example, the control device 2038 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 2030 and 2040 of FIGS. 34 and 35, respectively, include electronic components as part of the control device 2038 or the control device 2048. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 2030 and 2040, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 2030 and 2040 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 39:
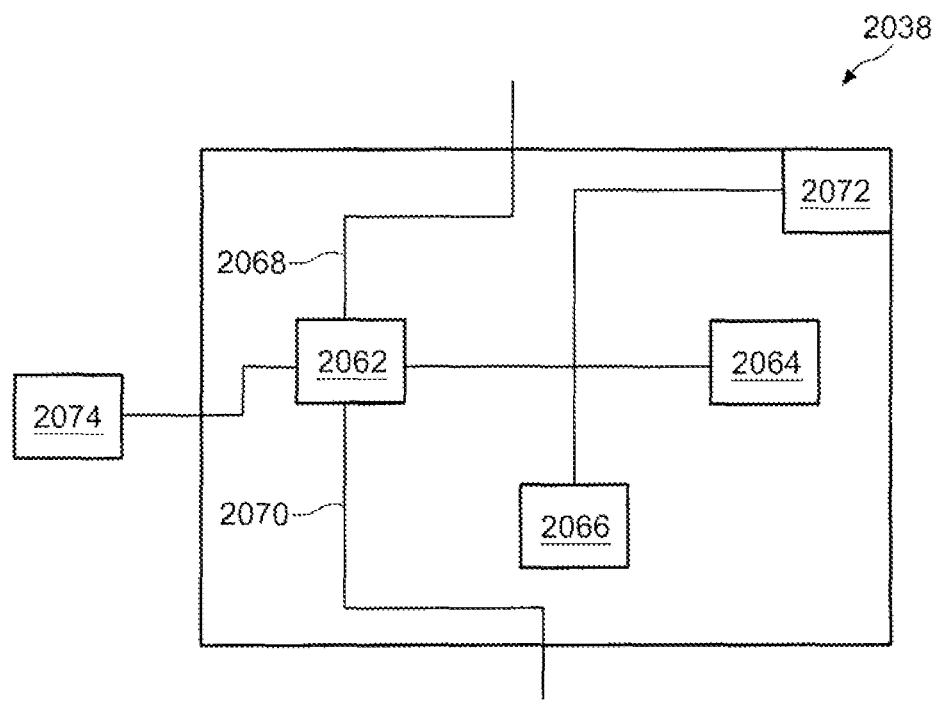
FIG. 39 is a block diagram illustration of one aspect of the control device used in the system of FIGS. 34 and 35.

Referring now to FIG. 39, a block diagram representation of the control device 2038 is shown. The device 2030 includes a control module 2062, a counter or clock 2064, and a memory 2066. Additionally, the device 2038 is shown to include a sensor module 2072 as well as the sensor module 2074, which was referenced in FIG. 36. The control module 2062 has an input 2068 electrically coupled to the material 2034 and an output 2070 electrically coupled to the material 2036. The control module 2062, the clock 2064, the memory 2066, and the sensor modules 2072/2074 also have power inputs (some not shown). The power for each of these components is supplied by the voltage potential produced by the chemical reaction between materials 2034 and 2036 and the conducting fluid, when the system 2030 is in contact with the conducting fluid. The control module 2062 controls the conductance through logic that alters the overall impedance of the system 2030. The control module 2062 is electrically coupled to the clock 2064. The clock 2064 provides a clock cycle to the control module 2062. Based upon the programmed characteristics of the control module 2062, when a set number of clock cycles have passed, the control module 2062 alters the conductance characteristics between materials 2034 and 2036. This cycle is repeated and thereby the control device 2038 produces a unique current signature characteristic. The control module 2062 is also electrically coupled to the memory 2066. Both the clock 2064 and the memory 2066 are powered by the voltage potential created between the materials 2034 and 2036.

The control module 2062 is also electrically coupled to and in communication with the sensor modules 2072 and 2074. In the aspect shown, the sensor module 2072 is part of the control device 2038 and the sensor module 2074 is a separate component. In alternative aspects, either one of the sensor modules 2072 and 2074 can be used without the other and the scope of the present disclosure is not limited by the structural or functional location of the sensor modules 2072 or 2074. Additionally, any component of the system 2030 may be functionally or structurally moved, combined, or repositioned without limiting the scope of the present disclosure. Thus, it is possible to have one single structure, for example a processor, which is designed to perform the functions of all of the following modules: the control module 2062, the clock 2064, the memory 2066, and the sensor module 2072 or 2074. On the other hand, it is also within the scope of the present disclosure to have each of these functional components located in independent structures that are linked electrically and able to communicate.

Referring again to FIG. 39, the sensor modules 2072 or 2074 can include any of the following sensors: temperature, pressure, pH level, and conductivity. In one aspect, the sensor modules 2072 or 2074 gather information from the environment and communicate the analog information to the control module 2062. The control module then converts the analog information to digital information and the digital information is encoded in the current flow or the rate of the transfer of mass that produces the ionic flow. In another aspect, the sensor modules 2072 or 2074 gather information from the environment and convert the analog information to digital information and then communicate the digital information to control module 2062. In the aspect shown in FIG. 36, the sensor modules 2074 is shown as being electrically coupled to the material 2034 and 2036 as well as the control device 2038.

In another aspect, as shown in FIG. 39, the sensor module 2074 is electrically coupled to the control device 2038 at connection 2078. The connection 2078 acts as both a source for power supply to the sensor module 2074 and a communication channel between the sensor module 2074 and the control device 2038.

Figure 38:
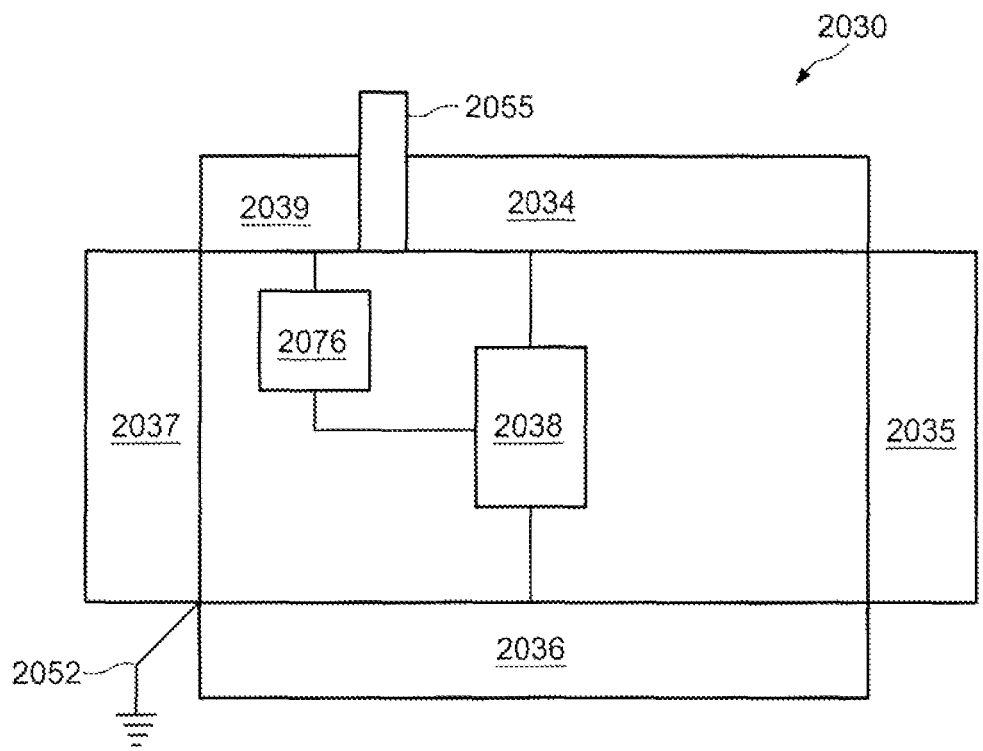
FIG. 38 shows the event indicator system of FIG. 5 with a pH sensor unit.

Referring now to FIG. 38, the system 2030 includes a pH sensor module 2076 connected to a material 2039, which is selected in accordance with the specific type of sensing function being performed. The pH sensor module 2076 is also connected to the control device 2038. The material 2039 is electrically isolated from the material 2034 by a non-conductive barrier 2055. In one aspect, the material 2039 is platinum. In operation, the pH sensor module 2076 uses the voltage potential difference between the materials 2034/2036. The pH sensor module 2076 measures the voltage potential difference between the material 2034 and the material 2039 and records that value for later comparison. The pH sensor module 2076 also measures the voltage potential difference between the material 2039 and the material 2036 and records that value for later comparison. The pH sensor module 2076 calculates the pH level of the surrounding environment using the voltage potential values. The pH sensor module 2076 provides that information to the control device 2038. The control device 2038 varies the rate of the transfer of mass that produces the ionic transfer and the current flow to encode the information relevant to the pH level in the ionic transfer, which can be detected by a receiver (not shown). Thus, the system 2030 can determine and provide the information related to the pH level to a source external to the environment.

As indicated above, the control device 2038 can be programmed in advance to output a pre-defined current signature. In another aspect, the system can include a receiver system that can receive programming information when the system is activated. In another aspect, not shown, the switch 2064 and the memory 2066 can be combined into one device.

In addition to the above components, the system 2030 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc.

In various aspects, the techniques described herein provide bonding of a skirt material and or/sensor surface to the tablet powdered material blend or granulation during compression of tablets or the placement of an electronic device such as an IEM in the tablet press for sensor-in-tablet platform. In one aspect, texture or features may be added to the skirt film during manufacturing of the film, during manufacturing of the IEM, or after manufacturing the IEM. The texture may be created by mechanical deformation of the skirt, laser texturing of the skirt, chemical etch, or by making the formulation more porous, or by thermal processing. In another aspect, macroscale features may be created such as holes, slots, indentations, or other shapes to provide tablet bonding or riveting to the IEM. In yet another aspect, an adhesive may be added to the skirt, or otherwise the skirt may be made sticky to enhance bonding of the tablet material to the IEM.

Figure 40:
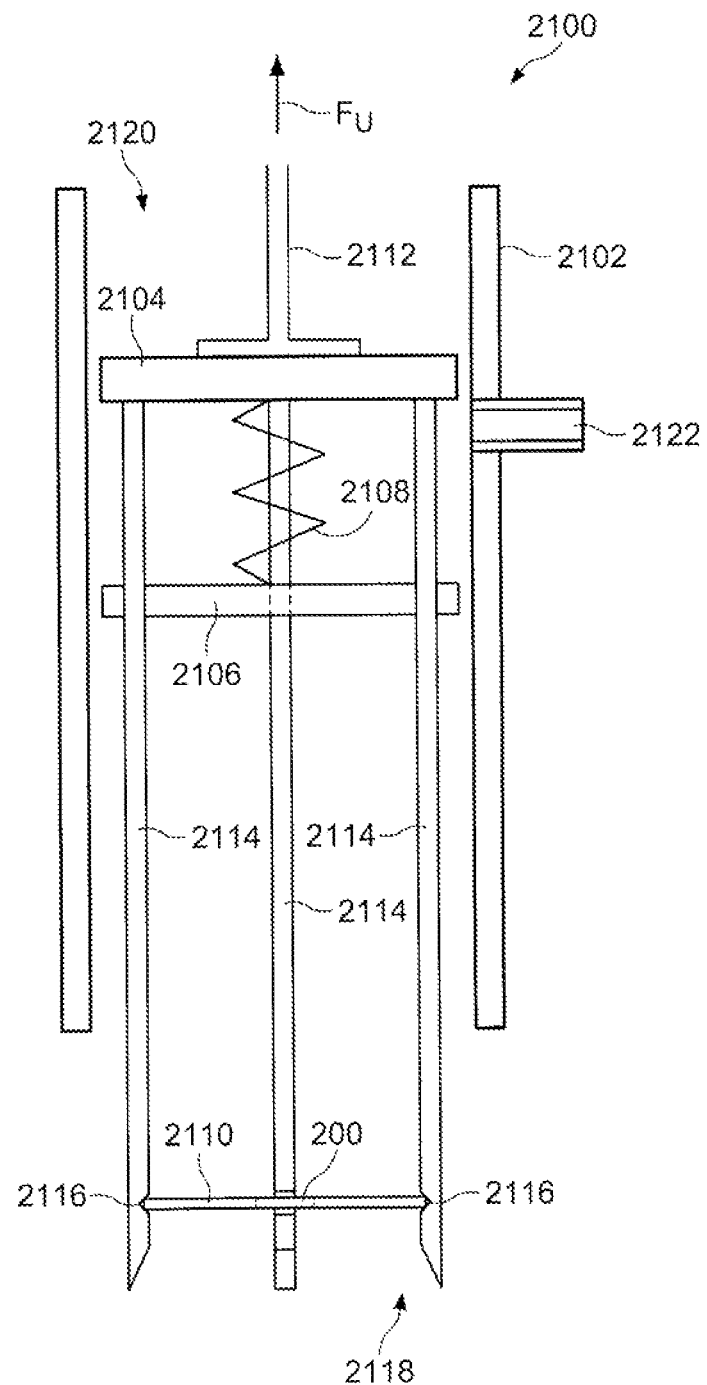
FIGS. 40 and 41 are cross-sectional side-views of one aspect of a pick-and-place transfer mechanism for picking an electronic device from a cavity of a carrier tape.
Figure 41:
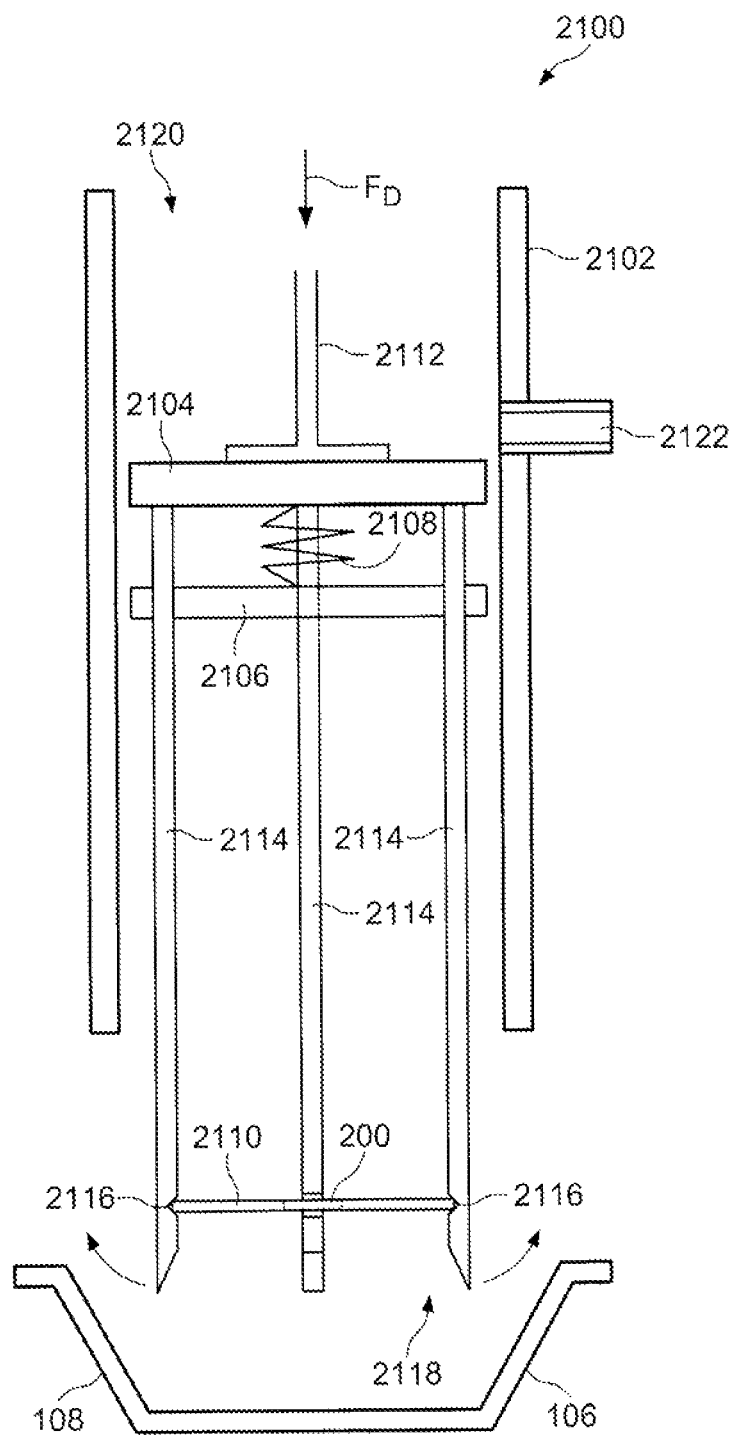

FIGS. 40 and 41 illustrate one aspect of a pick-and-place transfer mechanism 2100 for picking an electronic device 200 from a cavity 108 of a carrier tape 106 and transferring the electronic device 200. The pick-and-place transfer mechanism 2100 comprises a housing 2102 that defines a chamber 2120 to contain a movable pressure plate 2104 and a movable prong holder plate 2106. The pressure plate 2104 is movable in a downward direction to pick an electronic device 200 comprising a skirt 2110 by the application of a force $F_D$, which also compresses a spring 2108. The spring 2108 stores energy and applies an upward force $F_U$ to lift the electronic device 200 from the cavity 108 of the carrier tape 106. The downward force $F_D$ may be applied mechanically by a piston 2112 (as shown) or by pressurized air acting against the pressure plate 2104. If the downward force $F_D$ is applied by the piston 212, the spring force $F_C$ may be used as the lifting force. If the downward force $F_D$ is applied by pressurized air, then the application of a vacuum may be employed to lift the pressure plate 2104.

Figure 45:
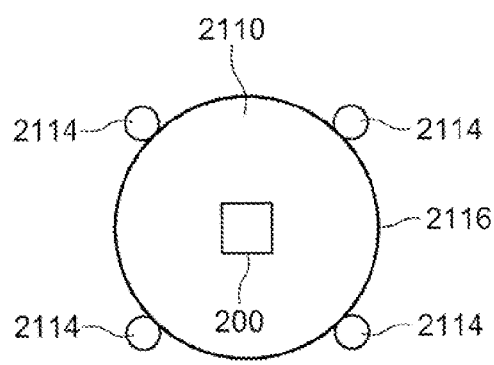
FIG. 45 illustrates a bottom view perspective of four prongs engaging an outer diameter of a skirt portion of an electronic device.

Attached to the pressure plate 2104 are a plurality of prongs 2114 (arms), which are elongated members employed to engage the outer diameter 2116 (perimeter) of the skirt 2110 portion of the electronic device 200 in order to lift the electronic device 200 out of the cavity 108. In one aspect four prongs 2114 are employed to grasp the outer diameter 2116 of the skirt 2110 surrounding the electronic device 200. This is best illustrated in FIG. 45, which illustrates a bottom view perspective of the four prongs 2114 engaging the outer diameter 2116 of the skirt 2110 portion of the electronic device 200. With reference now to FIGS. 40, 41, and 45, the four prongs 2114 are slidably disposed within corresponding apertures formed in prong holder 2106. The prong holder 2106 is configured such that the distal ends 2118 of the prongs 2114 expand slightly as indicted by the arrows in order to facilitate engagement of the perimeter of the skirt 2110. Once the electronic device 200 is grasped by the outer diameter 2116 of the skirt portion 2110 of the electronic device 200, the electronic device 200 can be released by extending and expanding the prongs 2114 from the spring loaded chamber 2120. This will help lock the electronic device 200 into a controlled environment to lift out of the carrier tape 106 and load into the rotary tablet press or onto a conveyor belt, as previously discussed.

In one aspect, the spring loaded chamber 2120 may comprise a vacuum opening 2122 on a side to add vacuum to assist with lifting and holding the electronic device 200.

Figure 42:
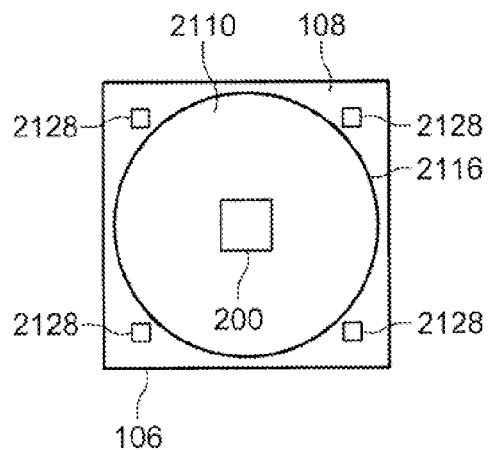
FIG. 42 is a top view of an electronic device located within a cavity of a carrier tape.
Figure 43:
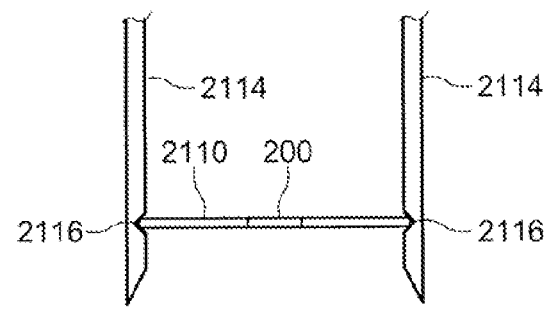
FIG. 43 is a side view of a pair of prongs grasping an electronic device.

FIG. 42 is a top view of the electronic device 200 located within the cavity 108 of the carrier tape 106. As illustrated, the electronic device 200 sits in a square surface mount technology (SMT) carrier tape 106 pocket or cavity 106, which leaves the four corners 2128 open and available to receive the distal ends 2118 of the prongs 2114. As described in connection with FIGS. 40 and 41, the prongs 2114 are attached to a spring loaded (or air actuated) chamber 2120 that expands the prongs 2114 to fit into the four corners 2128 of the carrier tape cavity 108 pocket, and then retracts and tightens the prongs 2114 around the outer diameter 2116 of the skirt 2110 portion of the electronic device 2110 as shown in FIG. 45, from a bottom view perspective, and FIG. 43 from a side view perspective.

Figure 44:
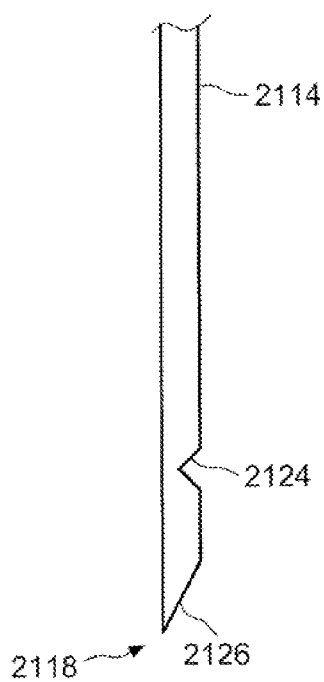
FIG. 44 illustrates features provided at a distal end of a prong to facilitate locating and grasping an electronic device using the pick-and-place transfer mechanism shown in FIGS. 41 and 42.

As shown in FIG. 44, the distal end 2118 of each prong 2114 comprises feature to assist locating and grasping the electronic device 200. In one aspect, for example, a indent 2124 feature located near the distal end 2118 of the prong 2114 will assist to secure the electronic device 200 into place. Also, the tip portion of the prong 2114 comprises a slight chamfer 2126 to help slide the prong 2114 corners 2128 inside the cavity 108 portion of the carrier tape 106.

FIG. 46A is a cross-sectional view of one aspect of a pick-and-place tool 2150 holding an electronic device 200 within a mechanical gripper 2154. FIG. 46B is a bottom view of the pick-and-place tool 2150 holding an electronic device 200 shown in FIG. 46A. With reference to both FIGS. 46A and 46B, as shown, a vacuum tube 2152 pick tool is located within a chamber 2158 defined by a mechanical gripper 2154. The pick-and-place tool 2150 may comprise a plurality of mechanical grippers 2154 comprising a flange 2156 portion for grasping and holding the outer diameter 2116 portion of the skirt 2110 portion of the electronic device 200. As illustrated in FIG. 46B, in one aspect, the pick-and-place tool 2150 may comprise four mechanical grippers 2154 each comprising a flange 2156 portion for clamping or grasping and holding the electronic 200 by the outer diameter 2116 of the skirt 2110. In operation, the mechanical gripper 2154 is sued to clamp around the outer diameter 2116 of the skirt 2110 portion of the electronic device 200. The distal ends 2160 of the mechanical gripper 2154 spread open when the pick-and-place tool 2150 is extended, but when the retracted, the mechanical gripper 2154 closes around the outer diameter 2116 of the skirt 2110 portion of the electronic device 200 and centers the electronic device 200 relative to the vacuum tube 2152 pick tip.

FIG. 47 illustrates one aspect of a friction hold disc mechanism 2170 for handling an electronic device 200. An electronic device 200 is initially contained within a tape carrier 2172. A cam driven pin 2174 movable in direction V is used to push the electronic device 200 from the carrier tape 2172 into a cavity 2180 of a rotating disc 2176. The electronic device 200 is pushed or placed in the cavity 2180 of the rotating disc 2176 and is then centered over a carrier 2178 before being pushed into the carrier 2178 by the vertically V cam driven pin 2174.

Figures 48, 49:
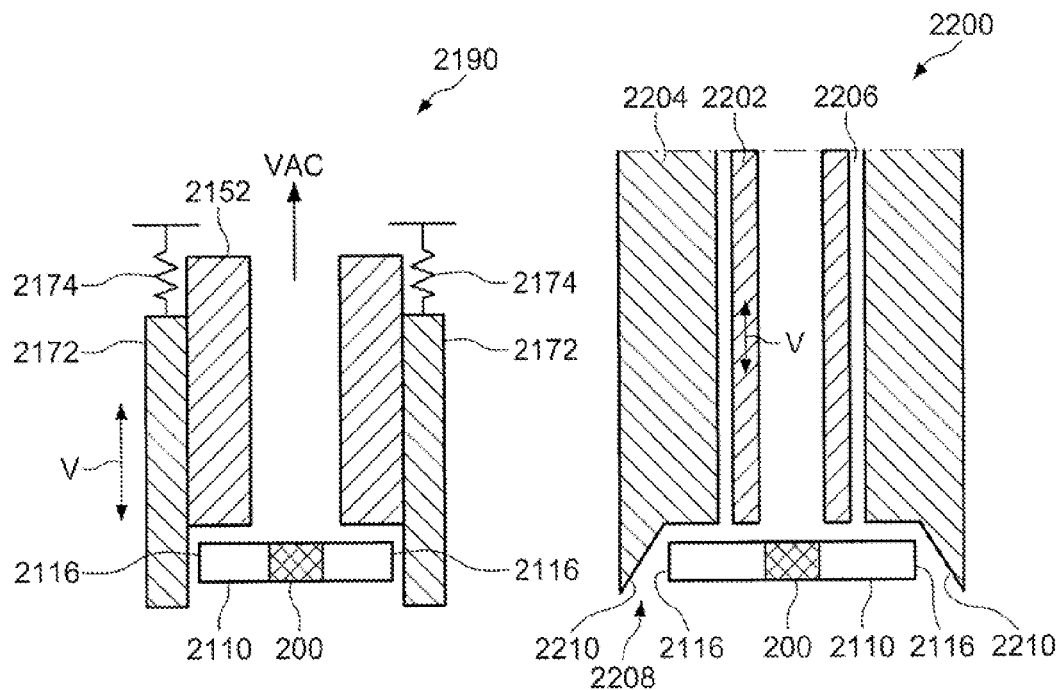
FIG. 48 illustrates one aspect of a pick-and-place transfer mechanism comprising a mobile sleeve.
FIG. 49 illustrates one aspect of a pick-and-place tool comprising an internal ejection member and a vacuum tube.

FIG. 48 illustrates one aspect of a pick-and-place tool 2170 comprising a mobile sleeve 2172. As shown in FIG. 48, the pick-and-place tool 2170 comprises mobile sleeve 2172 that is capable of moving up-and-down in a direction V. The mobile sleeve 2172 is spring 2174 loaded. As shown, the mobile sleeve 2172 is used to center the electronic device 200 relative to a vacuum tube 2152 pick tool is located within the mobile sleeve 2172.

FIG. 49 illustrates one aspect of a pick-and-place tool 2200 comprising an internal ejection member 2202 (plunger) and a vacuum tube 2204. The ejection member 2202 is movable in direction V within an inner chamber 2206 defined by the vacuum tube 2204. The distal end 2208 of the vacuum tube 2204 is shaped to center the electronic device 200 with the ejection member 2202. In the illustrated example, the distal end 2208 of the vacuum tube 2204 comprises tapered edges 2210 to slidably receive and center the electronic device 200 relative to the ejection member 2202. The electronic device 200 is picked when a vacuum is applied to the vacuum tube 2204. The ejection member 2202 may be spring loaded, or otherwise movable, to push out the electronic device 200 once the vacuum is removed for placement.

Figures 50, 51:
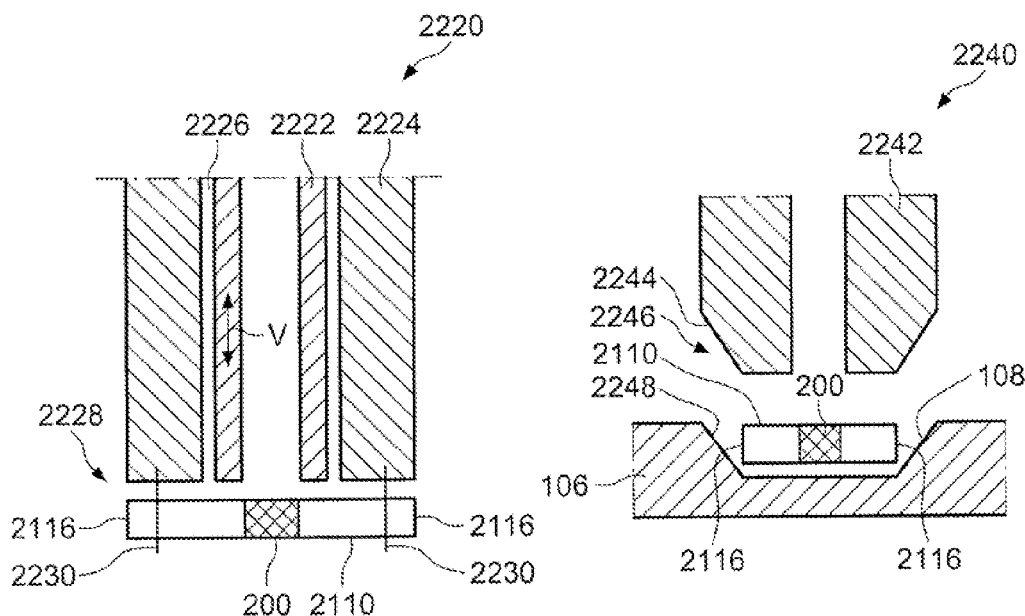
FIG. 50 illustrates one aspect of pick-and-place tool comprising an internal ejection member and an external tube comprising needles located at a distal end of the external tube.
FIG. 51 illustrates one aspect of pick-and-place tool comprising a head that has an external profile that matches the internal cavity profile of the carrier tape.

FIG. 50 illustrates one aspect of pick-and-place tool 2220 comprising an internal ejection member 2222 (plunger) and an external tube 2224 comprising needles 2230 located at a distal end of the external tube 2224. The needles 2230 puncture the skirt 2210 portion of the electronic device 200. The ejection tube 2222 is movable in direction V within an inner chamber 2226 defined by the external tube 2224. The ejection tube 2222 can be mechanically pushed to eject the electronic device 200 from the needles 2230 when the placed over a desired location. The ejection tube 2222 may be spring loaded or cam driven without the need of a vacuum source for picking and/or placing the electronic device.

FIG. 51 illustrates one aspect of pick-and-place tool 2240 comprising a head 2242 that has an external profile that matches the internal cavity profile of the carrier tape. As shown, the distal end 2246 of the head 2242 comprises a tapered outer wall 2244 where the profile of the tapered outer wall 2244 complements (or matches) the internal profile 2248 of the carrier tape 106 cavity 108. Thus, when the distal end 2246 of the head 2242 is inserted within the cavity 108 of the carrier tape 108, the distal end 2246 of the head 2242 is centered with the electronic device 200. Similarly, the shape of the tapered outer wall 2244 forces the electronic device 200 to be centered with a complementary shaped inner cavity during placement.

Figures 52, 53:
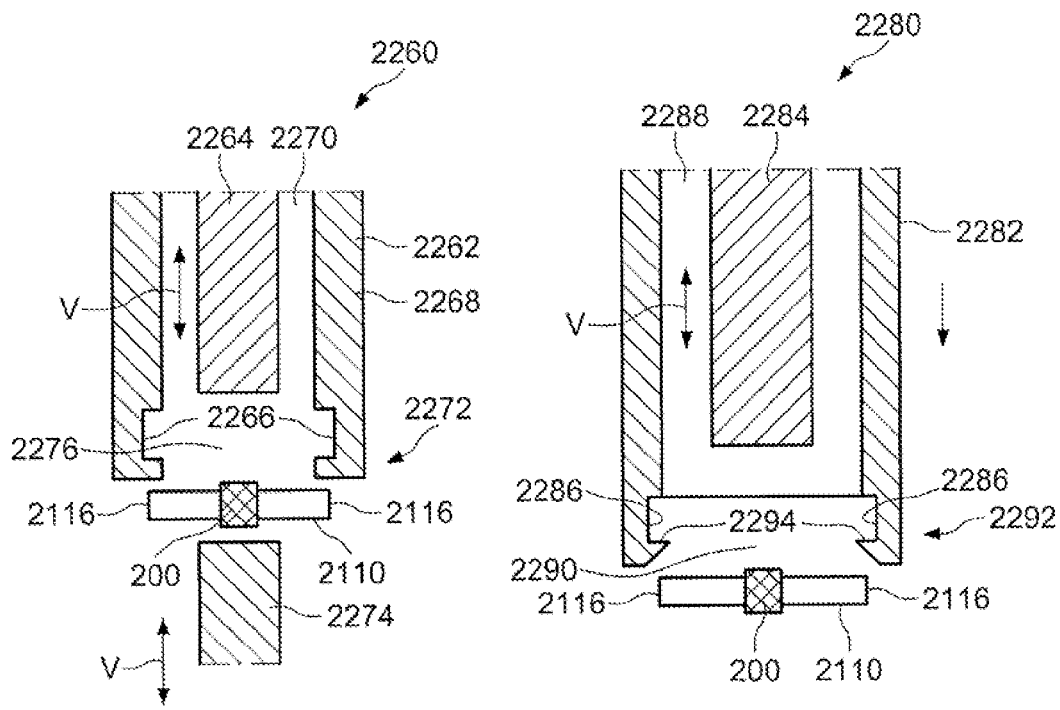
FIG. 52 illustrates one aspect of a pick-and-place tool comprising an inner slot at a distal end of a gripper.
FIG. 53 illustrates one aspect of a pick-and-place tool comprising an inner slot at a distal end of a gripper.

FIG. 52 illustrates one aspect of a pick-and-place tool 2260 comprising an inner slot 2266 at a distal end 2272 of a gripper 2268. As shown, the pick-and-place tool 2260 comprises an outer gripper 2268 with an inner slot 2266 defined at a distal end 2272 of the gripper 2268. A punch 2274 that is movable in direction V is used to push the electronic device 200 into a chamber 2276 defined within the distal end 2272 of the gripper 2268. The outer diameter 2116 of the skirt 2110 portion of the electronic device 200 flexes and snaps in and out of the slot 2266 within the chamber 2276. An ejection member 2264 that is movable in direction V is used to eject the electronic device 200 when it is time for placement.

FIG. 53 illustrates one aspect of a pick-and-place tool 2280 comprising an inner slot 2286 at a distal end 2292 of a gripper 2282. As shown, the pick-and-place tool 2280 comprises an outer gripper 2282 with an inner slot 2286 defined by snap elements 2294 located at the distal end 2292 of the gripper 2282. The pick-and-place tool 2280 is plunged in a downward direction to snap the outer diameter 2116 of the skirt 2110 portion of the electronic device 200 such that it is snapped into the chamber 2290. The outer diameter 2116 of the skirt 2110 portion of the electronic device 200 flexes and snaps in and out of the chamber 2290 and is held in place by the vertical seat defined by the snap elements 2294. An ejection member 2284 (plunger) that is movable in direction V is used to eject the electronic device 200 when it is time for placement.

Figures 54, 55:
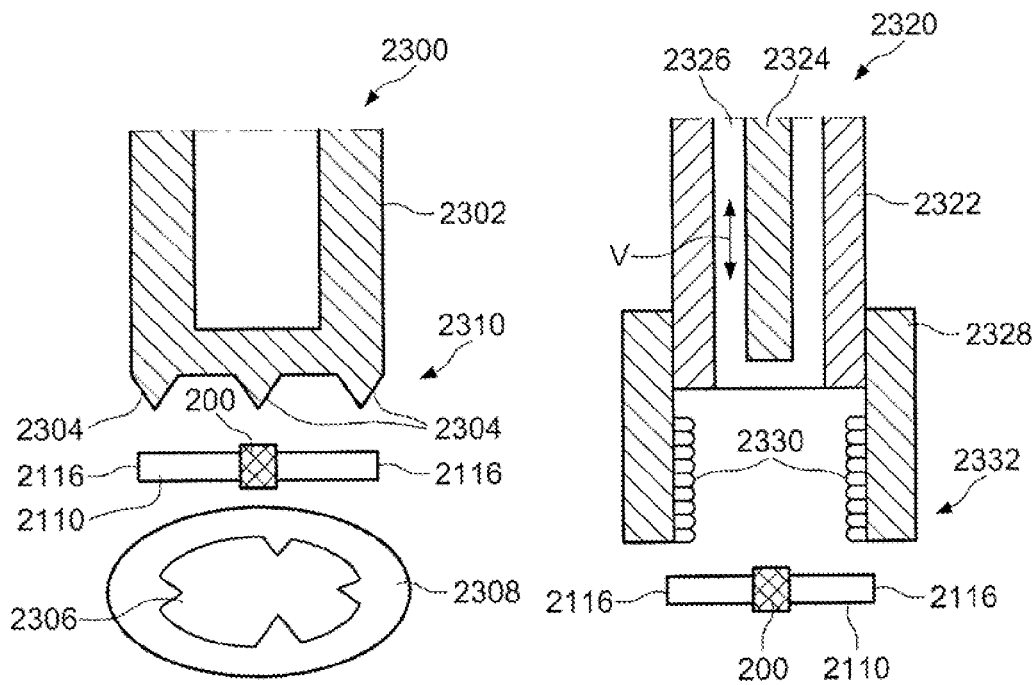
FIG. 54 illustrates one aspect of a pick-and-place tool comprising features at a distal end to create notches around the outer diameter of the skirt portion of the electronic device.
FIG. 55 illustrates one aspect of pick-and-place tool configured with hook-and-loop (VELCRO) or ridges at a distal end to hold the electronic device in place.

FIG. 54 illustrates one aspect of a pick-and-place tool 2300 comprising features 2304 at a distal end 2310 to create notches around the outer diameter 2116 of the skirt 2110 portion of the electronic device 200. The pick-and-place tool 2300 comprises a movable body portion 2302 and notching features 2304 at the distal end. The notching features 2304 pinch the edges of the skirt material 2308 to create notches in the skirt portion 2110 of the electronic device 200 for frictional holding in a carrier. The cutout 2306 portion below the tool 2300 shows the features formed in the skirt 2110 portion of the electronic device 200. Since the notched edges hold the electronic device 200 in a carrier or cavity by friction, the electronic device 200 forced out by a plunger, similar to the ejection members described previously.

FIG. 55 illustrates one aspect of pick-and-place tool 2320 configured with hook-and-loop (VELCRO) or ridges 2330 at a distal end 2332 to hold the electronic device 200 in place. The pick-and-place tool 2320 comprises an outer body 2322 portion defining an inner chamber 2326 for movably receiving therein an ejection member 2324 (plunger) that is movable in direction V. A distal end 2332 of the pick-and-place tool 2320 comprises hook-and-loop (VELCRO) or ridges 2330 at a distal end 2332 to hold the electronic device 200. The ejection tool 2324 or plunger is used to force out or eject the electronic device when it is time for placement.

Figure 56:
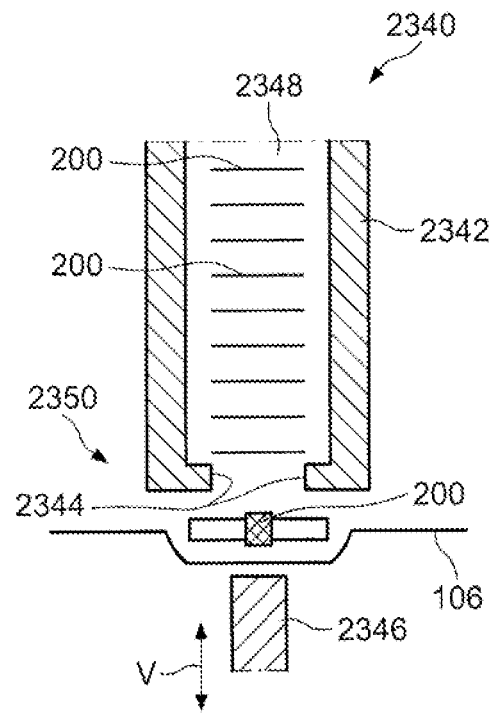
FIG. 56 illustrates one aspect of a tower for storing electronic devices.

FIG. 56 illustrates one aspect of a tower 2340 for storing electronic devices 200. In the illustrated example, the tower 2340 comprises a cylindrical body 2342 defining an inner chamber 2348 suitable for storing electronic devices 200. The cylindrical body 2342 comprises seats 2344 or ledges to holding the electronic devices 200 within the chamber 2348.

Electronic devices 200 are located below the tower body 2342 in the usual carrier tape 106. A punch 2346 movable in direction V is used to punch through the carrier tape 106 and load the electronic device 200 into the camber 2348.

Figure 57:
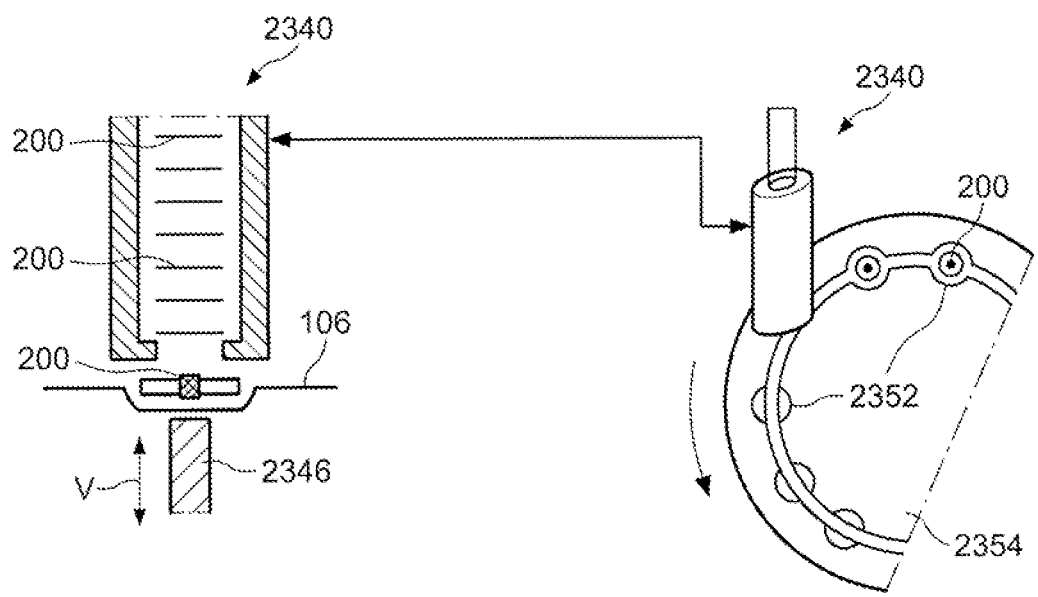
FIG. 57 illustrates one aspect of the tower shown in FIG. 56 interfaced with a rotary transfer plate.

FIG. 57 illustrates one aspect of the tower 2340 interfaced with a rotary transfer plate 2354. A shown, the tower 2340 may be flipped upside down to dispense the electronic devices 200 into nests 2352 located on the rotary transfer plate 2354.

Figure 58:
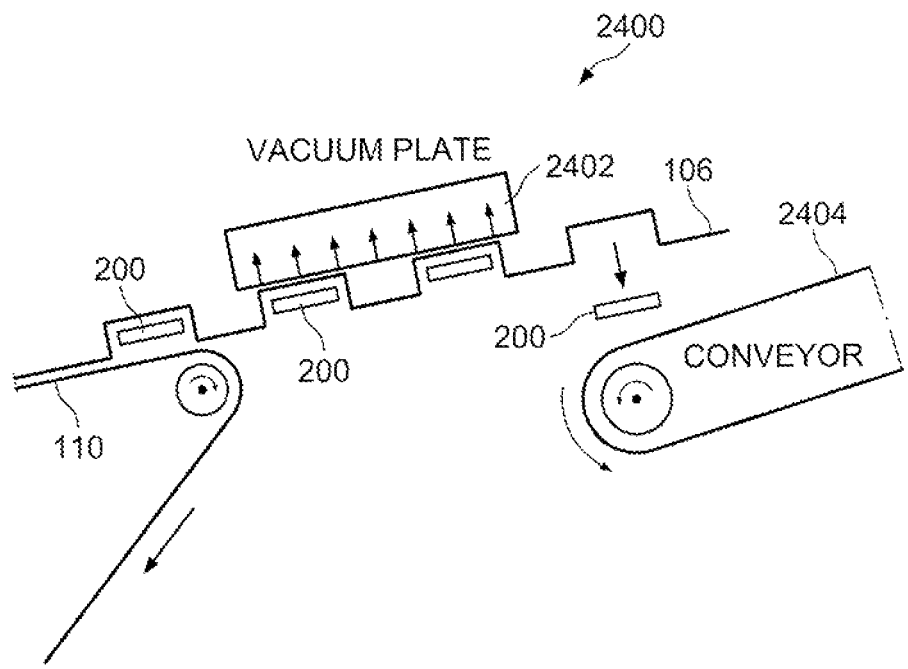
FIG. 58 illustrates one aspect of a transfer mechanism employing a vacuum plate for holding electronic devices until they are ready to be dispensed.

FIG. 58 illustrates one aspect of a transfer mechanism 2400 employing a vacuum plate 2402 for holding electronic devices 200 until they are ready to be dispensed. In the illustrated example, the electronic devices 200 are moving along the in the carrier tape 106. Just prior to reaching the vacuum plate 2402, the cover tape 110 is removed such that the vacuum plate 2402 applies negative pressure to the top side of the electronic device 200 to hold the electronic device 200 in place until ready for dispensing on a conveyor 2404, as shown, or a carrier.

Figure 59:
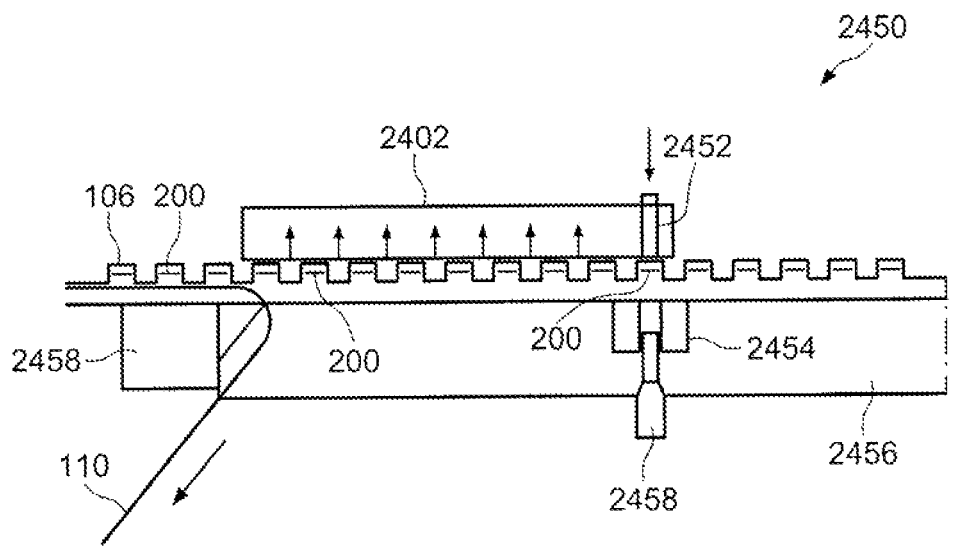
FIG. 59 illustrates another aspect of a transfer mechanism that employs a vacuum plate for holding electronic devices until they are ready to be dispensed.

FIG. 59 illustrates another aspect of a transfer mechanism 2450 that employs a vacuum plate 2402 for holding electronic devices 200 until they are ready to be dispensed. The electronic devices 200 are supplied by way of the carrier tape 106. The cover tape 110 is removed at a stripping station 2458 just prior to the vacuum plate 2402 such that when the cover tape 110 is removed, the negative pressure from the vacuum plate is applied to the top portion of the electronic device 200 to hold the electronic device in place until it is time to dispense. In the illustrated example, an insert pin 2452 pushes out the electronic device 200 into a die cavity 2454 located on the tablet top plate 2456. A bottom punch 2458 is used to form the electronic device 200 into a tablet using the die cavity 2454.

Figure 60:
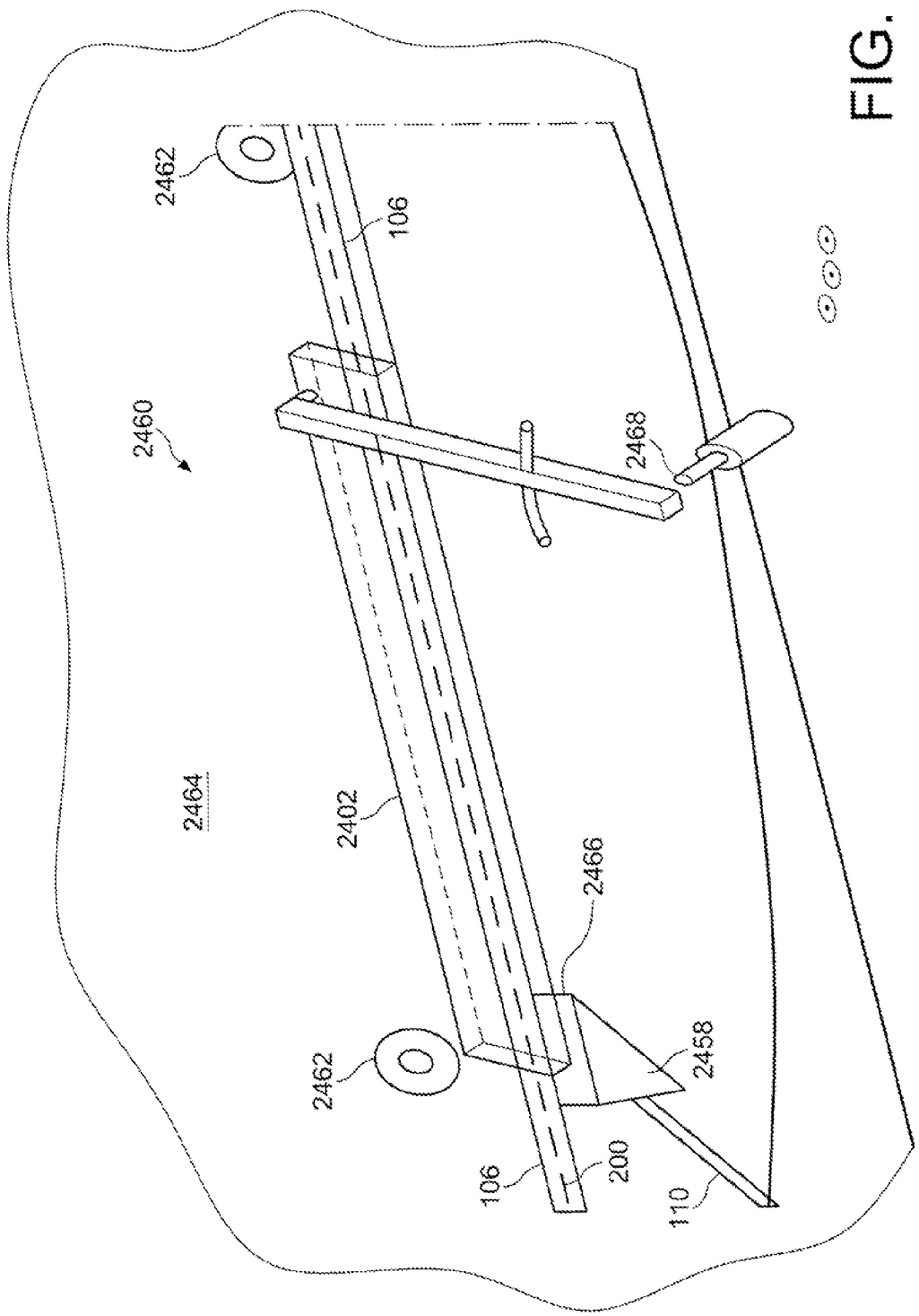
FIG. 60 illustrates one aspect of a transfer mechanism that employs a vacuum plate for holding electronic devices until they are ready to be dispensed.

FIG. 60 illustrates one aspect of a transfer mechanism that employs a vacuum plate 2402 for holding electronic devices 200 until they are ready to be dispensed. The electronic devices 200 are supplied by way of the carrier tape 106. The cover tape 110 is removed at a stripping station 2458 by a stripping edge 2455 just prior to the vacuum plate 2402 such that when the cover tape 110 is removed, the negative pressure from the vacuum plate is applied to the top portion of the electronic device 200 to hold the electronic device in place until it is time to dispense. In the illustrated example, an insert pin 2468 pushes out the electronic device 200 into a die cavity 2462 located on the tablet top plate 2464. The insert pin 2468 moves through the carrier tape 106 to push the electronic device 200 into the die cavity 2462. In one aspect, the insert pin 2468 activation can be linear motion.

Figure 61:
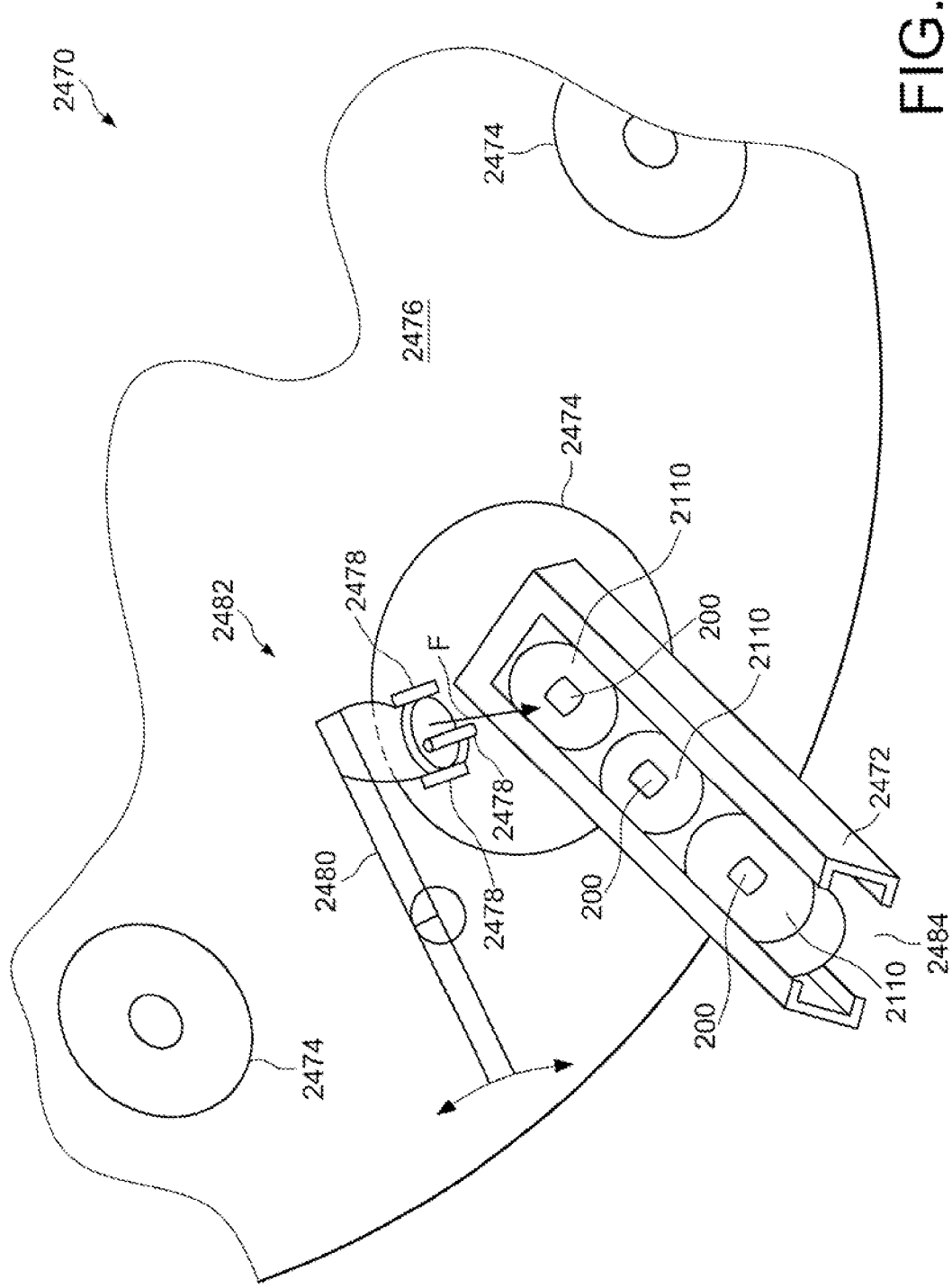
FIG. 61 illustrates one aspect of a transfer mechanism employing a rail feed to supply the electronic devices top the tablet process table top.

FIG. 61 illustrates one aspect of a transfer mechanism 2470 employing a rail feed 2472 to supply the electronic devices 200 top the tablet process table top 2476. In the illustrated example, the electronic devices 200 are supplied to the punch station 2482 above the punch die cavity 2474 by way of the rail feed 2472. A linear actuator 2480 having electronic device 200 alignment pins 2478 is used to transfer the electronic device 100 into the die cavity 2474. The electronic devices 200 are forced down the rail feed 2472 into insert position. The linear actuator 2480 aligns the electronic device 200 with four pins 2478 and then applies a force F to the electronic device 200 to bend or flex the skirt 2110 portion of the electronic device 200 slightly out of the opening 2484 beneath the rail feed 2472 and in to the die cavity 2474. In another aspect, the linear actuator 2480 dispense the electronic devices 200 into carriers or nests located on the process table top 2476.

Figure 62:
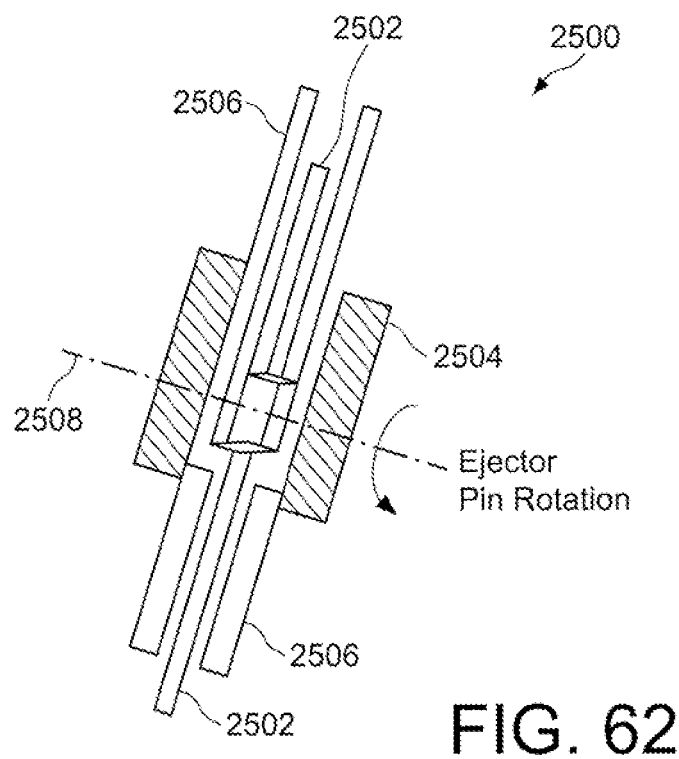
FIG. 62 illustrates a cross sectional view of an ejection mechanism that rotates eccentrically about a first axis.

FIG. 62 illustrates a cross sectional view of an ejection mechanism 2500 that rotates eccentrically about a first axis 2508. The ejection mechanism 2500 comprises vacuum tubes 2506 and ejector members 2502 therebetween. The ejector members 2502 are rotatably attached to a wheel 2504 that rotates eccentrically such that the ejector members 2502 act on the electronic device.

Figure 63:
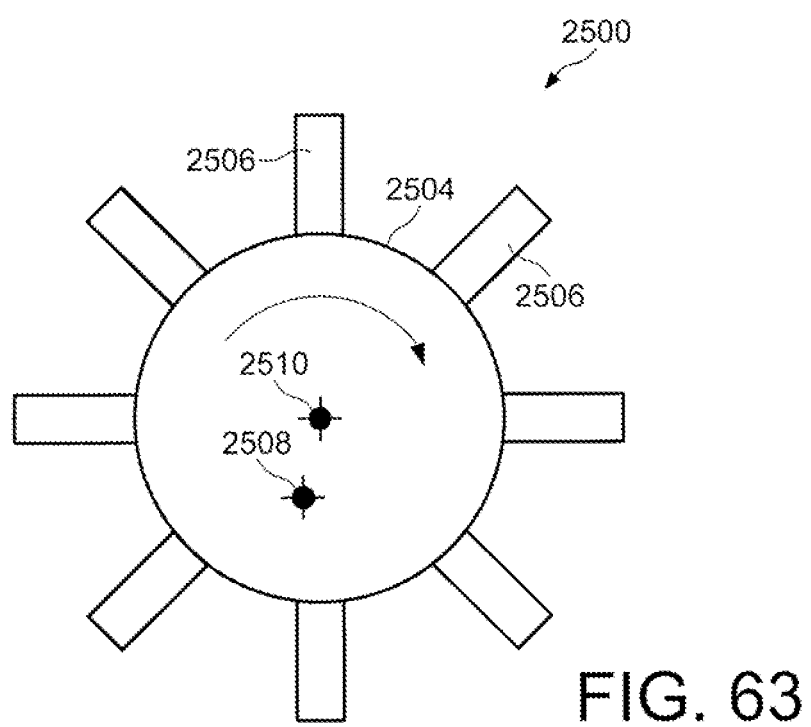
FIG. 63 illustrates a side view of the ejection mechanism shown in FIG. 62.

FIG. 63 illustrates a side view of the ejection mechanism 2500 shown in FIG. 62. As shown, the wheel 2504 rotates about the axis 2508, which causes the ejector members 2502 to move accordingly. A second wheel attached to the vacuum tubes 2506 (not shown) rotates about a center axis 2510.

Figure 64:
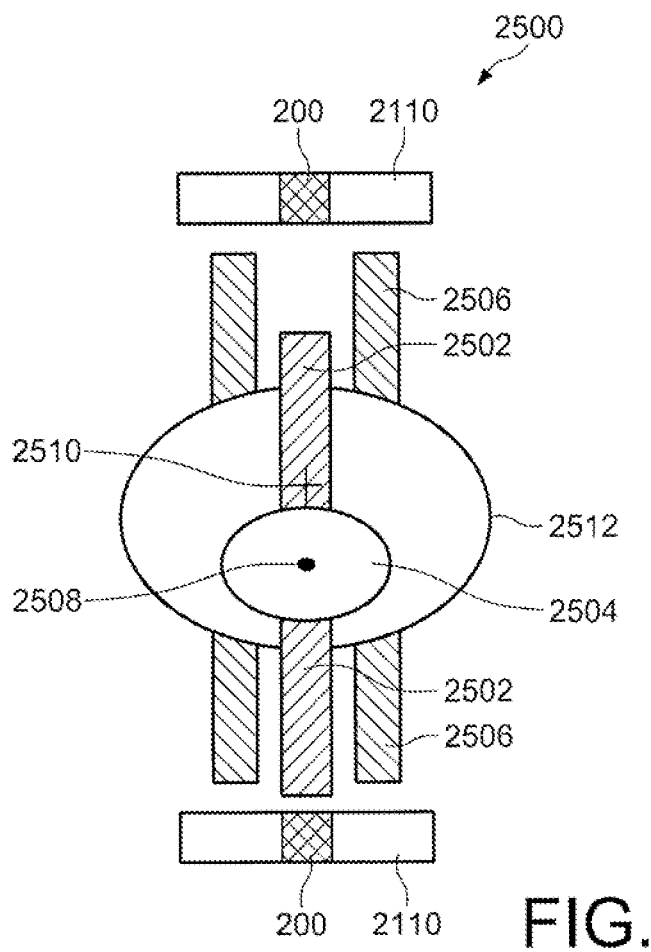
FIG. 64 illustrates a cross sectional view of the ejection mechanism shown in FIGS. 62 and 63.

FIG. 64 illustrates a cross sectional view of the ejection mechanism 2500 shown in FIGS. 62 and 63. As shown, the vacuum tubes 2506 hold the electronic device 200 place. The ejector members 2502 are coupled to a first wheel 2504 that rotates eccentrically about the axis 2508. The vacuum tubes 2506 for holding the electronic device 200 are coupled to a second wheel 2512 that rotates on center about axis 2510. Thus, when the electronic device 200 gets to the bottom and interfaces with the tablet press cavity, the offset ejector member 2502 ejects the electronic device 200 out into the cavity.

Figure 65:
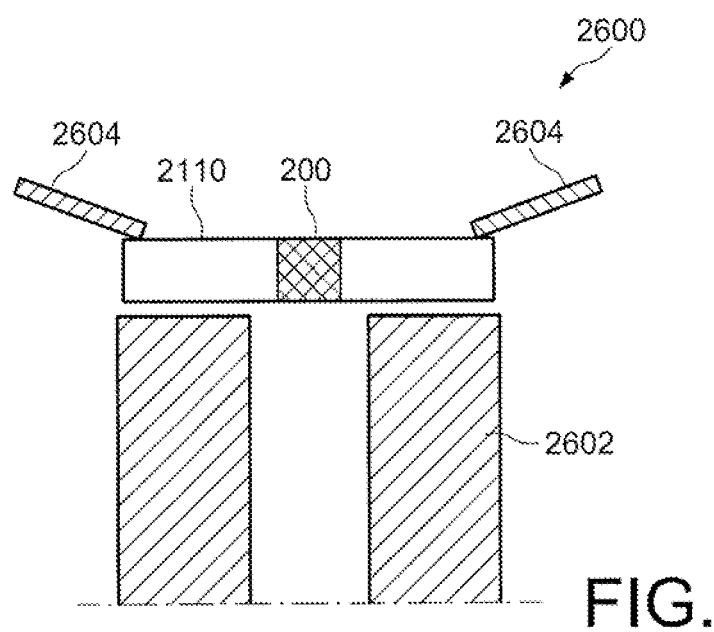
FIG. 65 illustrates a pick-and-place tool comprising a body and flexible (resilient) fingers or flaps to grasp and hold the electronic device.

FIG. 65 illustrates a pick-and-place tool 2600 comprising a body 2602 and flexible (resilient) fingers or flaps 2604 to grasp and hold the electronic device 200. In one aspect, the resilient fingers 2604 may be made of rubber or other suitable material.

Figure 66:
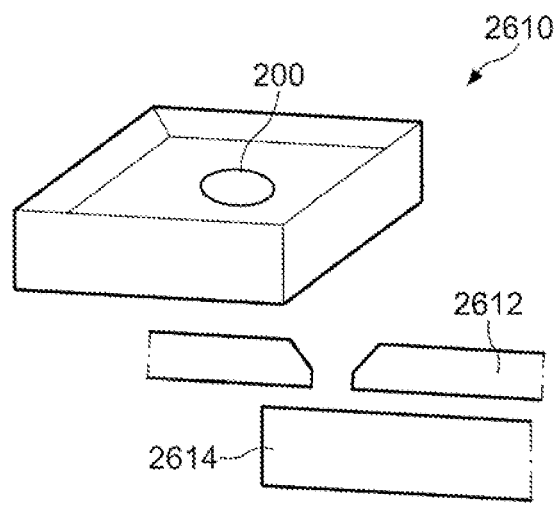
FIG. 66 illustrates one aspect of a transfer mechanism that employs gravity.

FIG. 66 illustrates one aspect of a transfer mechanism 2610 that employs gravity. The transfer mechanism 2610 uses of gravity and a plated template 2612 to allow an electronic device 200 to fall into the press 2614 and center it as it falls thru the template.

Figure 67:
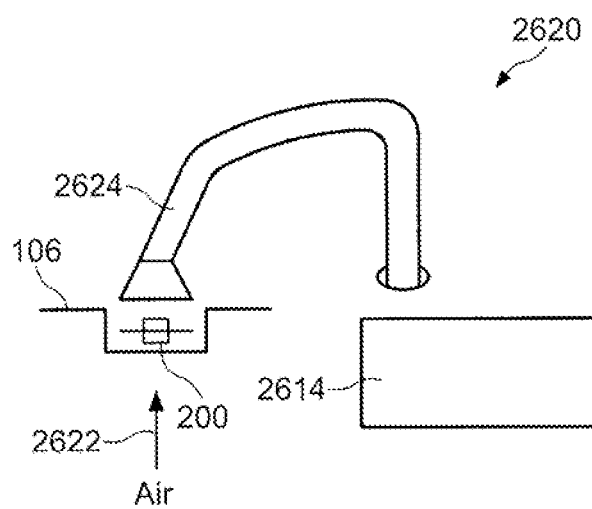
FIG. 67 illustrates one aspect of a transfer mechanism that employs air pressure.

FIG. 67 illustrates one aspect of a transfer mechanism 2620 that employs air pressure. The transfer mechanism 2620 uses air pressure 2622 from the bottom of the carrier tape 106 to push the electronic device 200 out of the carrier tape 106 through a pressurized feeder tube 2624 which ejects the electronic device 200 into the press 2614.

Figure 68:
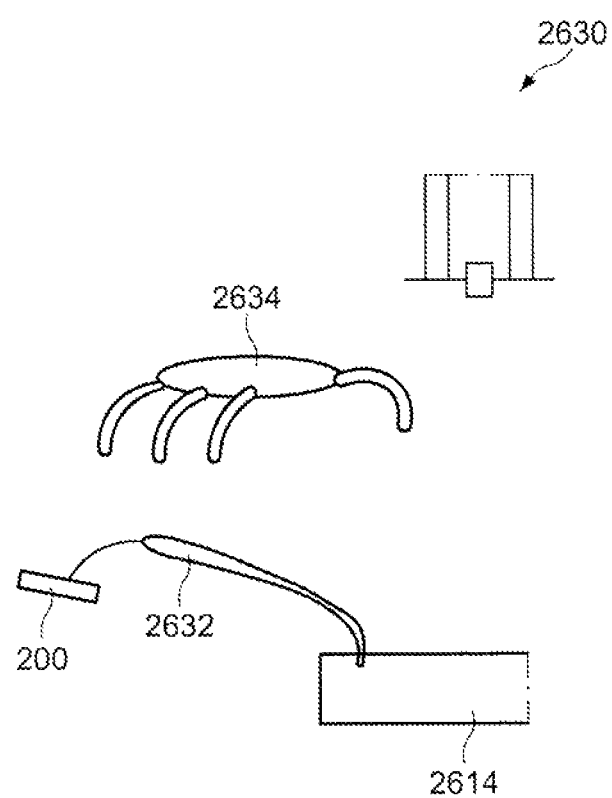
FIG. 68 illustrates one aspect of a transfer mechanism that employs a vacuum feeder.

FIG. 68 illustrates one aspect of a transfer mechanism 2630 that employs a vacuum feeder. The transfer mechanism 2630 uses a vacuum feeder wheel 2632 that holds the electronic devices 200 by a vacuum tube and the wheel spins and places the electronic device 200 in the press 2614. In one aspect, the vacuum feeder 2634 has an array of vacuum heads.

Figure 69:
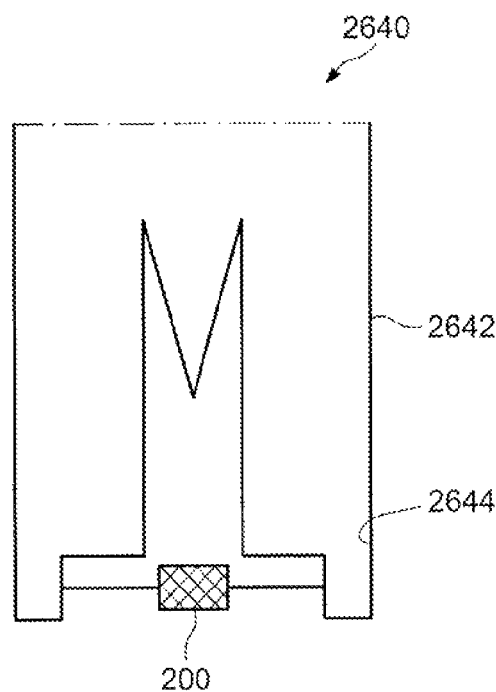
FIG. 69 illustrates one aspect of collet gripper having a body that expands during the grip process, then contracts on the electronic device forming positive pressure grip around the outside of the electronic device.

FIG. 69 illustrates one aspect of collet gripper 2640 having a body 2642 that expands during the grip process, then contracts on the electronic device 200 forming positive pressure grip around the outside of the electronic device 200. The mechanism to open and close the collet gripper head 2644 can be cam driven (pointy arrow in middle).

FIG. 70 illustrates one aspect of a transfer mechanism 2650 comprising a pre punched film/carrier tape 2652 that holds the electronic device 200 so that punching the electronic device 200 out into the press tool 2654 with a punch 2656 can be facilitated. This would also facilitate unique perimeter designs mentioned previously.

FIG. 71 illustrates one aspect of a transfer mechanism 2660 as shown in FIG. 70 except that the punch occurs into a rotating plate 2664 that may hold the electronic device 200 with a friction fit around the perimeter, or have some mechanical feature to lock in place. This rotating plate can move the electronic device 200 into the press area.

FIG. 72 illustrates a transfer mechanism 2670 comprising electrically charged pick-up head with fingers 2672, 2674 having opposite charge to grab the electronic device and hold the electronic device 200 in place by electrostatic forces.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

While certain features of the aspects have been illustrated as described herein, many modifications, substitutions, changes and equivalents will now occur to those skilled in the art. It is therefore to be understood that the appended claims are intended to cover all such modifications and changes as fall within the true scope of the disclosed aspects.

The invention claimed is:

1. A method of manufacturing a tablet comprising an electronic device, the method comprising:
   providing a powdered material into a die cavity of a tablet press;
   dispensing an electronic device from a tape-and-reel carrier tape operatively coupled to the tablet press, the carrier tape configured for holding the electronic device;
   locating the electronic device into the die cavity; and
   compressing the powdered material and the electronic device to form a tablet; and
   wherein the carrier tape comprises a cover tape and defines a cavity for holding the electronic device between the cavity and the cover tape, wherein dispensing the electronic device from the carrier tape comprises:
      removing the cover tape from the carrier tape to expose the electronic device within the cavity;
      transferring the cover tape to a pick-and-place transfer mechanism;
      picking the electronic device from the cavity with a pick-and-place element of the transfer mechanism;
      transferring the pick-and-place element to the tablet press; and
      placing the electronic device in the die cavity.

2. The method of claim 1, further comprising pre-compressing the powdered material prior to locating the electronic device into the die cavity.

3. The method of claim 1, further comprising providing additional powdered material into the die cavity after forming the tablet.

4. The method of claim 3, further comprising compressing the additional powdered material to form the tablet.

5. The method of claim 1, wherein the tablet press is a rotary tablet press.

6. The method of claim 1, wherein the powdered material is a pharmaceutical material.

7. The method of claim 1, wherein the electronic device is an ingestible event marker.

8. The method of claim 1, further comprising locating the pick-and-place element above the die cavity.

9. The method of claim 8, further comprising:
   transferring the pick-and-place element to a carrier;
   locating the pick-and-place element above the carrier;
   placing the electronic device in the carrier;
   picking the electronic device from the carrier with a second pick-and-place element of a second transfer mechanism; and
   locating the second pick-and-place element above the die cavity.

10. The method of claim 1, wherein the pick-and-place element is a vacuum tool.

11. A method of manufacturing a tablet comprising an electronic device, the method comprising:
   providing a powdered material into a die cavity of a tablet press;
   dispensing an electronic device from a tape-and-reel carrier tape operatively coupled to the tablet press, the carrier tape configured for holding the electronic device;
   locating the electronic device into the die cavity; and
   compressing the powdered material and the electronic device to form a tablet; and
   wherein dispensing the electronic device from the tape carrier comprises:
      transferring the carrier tape to a punch press;
      punching through the carrier tape comprising the electronic device with an ejector pin portion of the punch press, wherein the ejector pin perforates the carrier tape; and
   dispensing the electronic device into the die cavity through the perforations;
   dispensing the electronic device into a carrier; and
   transferring the carrier to the tablet press.

12. The method of claim 11, wherein the carrier frictionally engages the electronic device and centers the electronic device with the die cavity.

13. A method of manufacturing a tablet comprising an electronic device, the method comprising:
   providing a powdered material into a die cavity of a tablet press;
   dispensing an electronic device from a tape-and-reel carrier tape operatively coupled to the tablet press, the carrier tape configured for holding the electronic device;
   locating the electronic device into the die cavity; and
   compressing the powdered material and the electronic device to form a tablet; and
   wherein the carrier tape carrier comprises first and second adhesive tapes for holding the electronic device therebetween, wherein dispensing the electronic device from the carrier tape comprises:
      removing the first adhesive tape from the carrier tape to expose the electronic device within the cavity;
      transferring the cover tape to a punch press;
      punching through the carrier tape comprising the electronic device with an ejector pin portion of the punch press, wherein the ejector pin perforates the carrier tape; and
      dispensing the electronic device into the die cavity through the perforations.

14. The method of claim 13, further comprising:
   dispensing the electronic device into a carrier; and
   transferring the carrier to the tablet press.

15. A system for manufacturing a tablet comprising an electronic device, the system comprising:
   a tablet press comprising a die cavity for receiving a powdered material and an electronic device therein, an upper punch, and a lower punch, wherein the upper and lower punches are operative to form the powdered material and the electronic device into a tablet;
   a tape-and-reel carrier tape operatively coupled to the tablet press, the carrier tape configured for holding the electronic device; and a transfer mechanism to transfer the electronic device from the tape carrier to the die cavity; and wherein the transfer mechanism comprises a pick-and-place transfer mechanism operatively coupled to the carrier tape and the tablet press.

16. A system for manufacturing a tablet comprising an electronic device, the system comprising:
- a tablet press comprising a die cavity for receiving a powdered material and an electronic device therein, an upper punch, and a lower punch, wherein the upper and lower punches are operative to form the powdered material and the electronic device into a tablet;
- a tape-and-reel carrier tape operatively coupled to the tablet press, the carrier tape configured for holding the electronic device; and
- a transfer mechanism to transfer the electronic device from the tape carrier to the die cavity; and
- further comprising a carrier to receive the electronic device and center the electronic device relative to the die cavity, wherein the pick-and-place transfer mechanism locates the electronic device in the carrier.

17. The system of claim 16, further comprising a second pick-and-place transfer mechanism to pick the electronic device from the carrier, locate the second pick-and-place transfer mechanism above the die cavity.

18. A system for manufacturing a tablet comprising an electronic device, the system comprising:
- a tablet press comprising a die cavity for receiving a powdered material and an electronic device therein, an upper punch, and a lower punch, wherein the upper and lower punches are operative to form the powdered material and the electronic device into a tablet;
- a tape-and-reel carrier tape operatively coupled to the tablet press, the carrier tape configured for holding the electronic device; and
- a transfer mechanism to transfer the electronic device from the tape carrier to the die cavity; and
- wherein the pick-and-place transfer mechanism comprises a vacuum tool.

19. The system of claim 18, further comprising a punch press for dispensing the electronic device from the tape carrier operatively coupled to the tablet press.

20. The system of claim 19, wherein the punch press comprises a rotating punch wheel.

21. A system for manufacturing a tablet comprising an electronic device, the system comprising:
- a tablet press comprising a die cavity for receiving a powdered material and an electronic device therein, an upper punch, and a lower punch, wherein the upper and lower punches are operative to form the powdered material and the electronic device into a tablet;
- a tape-and-reel carrier tape operatively coupled to the tablet press, the carrier tape configured for holding the electronic device; and
- a transfer mechanism to transfer the electronic device from the tape carrier to the die cavity; and
- wherein the carrier tape carrier comprises first and second adhesive tapes for holding the electronic device therebetween.

* * * * *